US012629379B2

(12) United States Patent
Matsuoka et al.

(10) Patent No.: US 12,629,379 B2
(45) Date of Patent: May 19, 2026

(54) PHARMACEUTICAL COMPOSITION FOR PREVENTING, SUPPRESSING, OR TREATING SYMPTOM ASSOCIATED WITH ALLERGIC REACTION

(71) Applicants: Nippon Chemiphar Co., Ltd., Tokyo (JP); Takasaki University of Health and Welfare, Gunma (JP)

(72) Inventors: Isao Matsuoka, Takasaki (JP); Masa-Aki Ito, Takasaki (JP); Kazuki Yoshida, Takasaki (JP)

(73) Assignees: Nippon Chemiphar Co., Ltd., Tokyo (JP); Takasaki University of Health and Welfare, Gunma (JP)

( * ) Notice: Subject to any disclaimer, the term of this patent is extended or adjusted under 35 U.S.C. 154(b) by 558 days.

(21) Appl. No.: 18/007,054

(22) PCT Filed: Aug. 2, 2021

(86) PCT No.: PCT/JP2021/028553
§ 371 (c)(1),
(2) Date: Jan. 27, 2023

(87) PCT Pub. No.: WO2022/030428
PCT Pub. Date: Feb. 10, 2022

(65) Prior Publication Data

US 2023/0277552 A1 Sep. 7, 2023

(30) Foreign Application Priority Data

Aug. 3, 2020 (JP) ................................ 2020-131412

(51) Int. Cl.

| | |
|---|---|
| ***C07D 243/12*** | (2006.01) |
| ***A61K 31/551*** | (2006.01) |
| ***A61K 31/5513*** | (2006.01) |
| ***A61K 45/00*** | (2006.01) |
| ***A61P 37/08*** | (2006.01) |
| ***C07D 243/38*** | (2006.01) |

(52) U.S. Cl.
CPC .......... *A61K 31/5513* (2013.01); *A61P 37/08* (2018.01)

(58) Field of Classification Search
CPC .. C07D 243/12; C07D 243/16; C07D 243/38; A61K 31/551; A61K 31/5513; A61K 45/00; A61P 37/08
See application file for complete search history.

(56) References Cited

U.S. PATENT DOCUMENTS

2007/0060595 A1 3/2007 Yoshizawa et al.

FOREIGN PATENT DOCUMENTS

| | | | |
|---|---|---|---|
| EP | 2803662 | A1 | 11/2014 |
| EP | 3020717 | A1 | 5/2016 |
| EP | 3449942 | A1 | 3/2019 |
| WO | 2005107804 | A1 | 11/2005 |
| WO | 2008020651 | A1 | 2/2008 |
| WO | 2008023847 | A1 | 2/2008 |
| WO | 2010093061 | A1 | 8/2010 |
| WO | 2012008478 | A1 | 1/2012 |
| WO | 2012014910 | A1 | 2/2012 |
| WO | 2012017876 | A1 | 2/2012 |
| WO | 2013105608 | A1 | 7/2013 |
| WO | 2015005467 | A1 | 1/2015 |
| WO | 2015005468 | A1 | 1/2015 |
| WO | 2019177117 | A1 | 9/2019 |
| WO | 2020050253 | A1 | 3/2020 |

OTHER PUBLICATIONS

Bing Hu et al., 5-BDBD ameliorates an OVA-induced allergic asthma by the reduction of Th2 cytokines production, JBMS, 2018, vol. 21, No. 4, pp. 364-369.
Hongxia Chen et al., Effect of P2X4R on airway inflammation and airway remodeling in allergic airway challenge in mice, Molecular Medicine Reports, 2016, vol. 13, pp. 697-704.
Kazuki Yoshida et al., Co-Stimulation of Purinergic P2X4 and Prostanoid EP3 Receptors triggers synergistic degranulation in Murine Mast Cells, International Journal of Molecular Sciences, 2019, vol. 20, No. 5157.
Guidelines for Nasal Allergy Treatment(Perennial rhinitis and hay fever), Practical Guideline for the Management of Allergic Rhinitis in Japan (PG-MARJ), 2013 edition (revised 7th edition), Tokyo Life Science;2013, pp. 34-63.
Nobuo Kubo, What is required for antihistamines, Folia Pharmacol. Jpn. 125, 2005; 125: 279-284.
Masahiro Takigawa et al., What do patients with pruritic skin disease want from antihistamines (antiallergic drugs)?—Questionnaire survey results—, Prog.Med. 2006; 26: 2289-2295.
Satoshi Ogino, Patient Satisfaction with Second Generation Anti-histamines in Hay Fever Treatment—Internet-based patient survey results (1st report)—, Prog.Med. 2009; 29: 2531-2537.
Yanai K. et al., Positron emission tomography evaluation of sedative properties of antihistamines, Expert Opin Drug Saf. 2011; 10: 613-622.
Holgate ST et al., Consensus Group on New-generation Antihistamines (CONGA): present status and recommendations, Clin Exp Allergy, 2003; 33: 1305-1324.
Masutaka Furue et al., Clinical practice guidelines for atopic dermatitis, Guidelines for Management of Atopic Dermatitis, Jpn J Dermatol 2009;119:1515-1534.
Brozek JL et al., Allergic Rhinitis and its Impact on Asthma (ARIA) guidelines: 2010 revision, J Allergy Clin Immunol. 2010; 126: 466-476.

(Continued)

*Primary Examiner* — Brenda L Coleman
(74) *Attorney, Agent, or Firm* — Wood Herron & Evans LLP

(57) ABSTRACT

The present invention relates to a pharmaceutical composition for preventing, suppressing, or treating a symptom associated with an allergic reaction, the pharmaceutical composition including a compound having a P2X4 receptor antagonizing action or a pharmaceutically acceptable salt thereof as an active ingredient.

24 Claims, 6 Drawing Sheets

(56) References Cited

OTHER PUBLICATIONS

K. Yoshida et al., Extracellular ATP augments antigen-induced murine mast cell degranulation and allergic responses via P2X4 receptor activation. J. Immunol. 2019.

PCT Office, International Search Report issued in PCT/JP2021/028553 dated Sep. 21, 2021.

Chinese Patent Office, Office Action issued in CN 202180067741.X dated Apr. 10, 2025.

European Patent Office, Search Report issued in EP 21853600.1 dated Oct. 7, 2024.

Zech Andreas et al: "P2rx4 deficiency in mice alleviates allergen-induced airway inflammation", Oncotarget, vol. 7, No. 49, Dec. 6, 2016 (Dec. 6, 2016), pp. 80288-80297, XP093052756, DOI: 10.18632/oncotarget.13375, Retrieved from the Internet: URL:https://www.ncbi.nlm.nih.gov/pmc/articles/PMC5348320/pdf/oncotarget-07-80288.pdf.

Wang Li et al: "P2X4R promotes airway remodeling by acting on the phenotype switching of bronchial smooth muscle cells in rats", Purinergic Signalling, Springer Verlag, DE, vol. 14, No. 4, Nov. 1, 2018 (Nov. 1, 2018), pp. 433-442, XP036661131, ISSN: 1573-9538, DOI: 10.1007/S11302-018-9625-4 [retrieved on Nov. 1, 2018].

"Abstracts—25th International Symposia on Morphological Science (ISMS) 2017 ED-Mühlfeld Christian; Ochs Matthias", Annals of Anatomy, Jena, DE, vol. 212, Jun. 27, 2017 (Jun. 27, 2017), pp. 6-334, XP085112872, ISSN: 0940-9602, DOI: 10.1016/J.AANAT.2017.05.003.

Yoshida Kazuki et al: "Divergent regulatory roles of extracellular ATP in the degranulation response of mouse bone marrow-derived mast cells", International Immunopharmacology, Elsevier, Amsterdam, NL, vol. 43, Dec. 15, 2016 (Dec. 15, 2016), pp. 99-107, XP029881755, ISSN: 1567-5769, DOI: 10.1016/J.INTIMP.2016.12.014.

European Patent Office, Search Report issued in EP 21853600.1 dated Jun. 17, 2024.

PHARMACEUTICAL COMPOSITION FOR PREVENTING, SUPPRESSING, OR TREATING SYMPTOM ASSOCIATED WITH ALLERGIC REACTION

TECHNICAL FIELD

The present invention relates to a pharmaceutical composition including a compound having a P2X4 receptor antagonizing action or a pharmaceutically acceptable salt thereof as an active ingredient, for example, a pharmaceutical composition for preventing, suppressing, or treating a symptom associated with an allergic reaction.

The present application claims priority based on Japanese Patent Application No. 2020-131412 filed in Japan on Aug. 3, 2020, the content of which is incorporated herein.

BACKGROUND ART

Increase in the number of patients with allergic diseases such as atopic dermatitis, asthma, and pollinosis has been a great problem especially in developed countries. An allergy is considered to be caused by an abnormal immune response of the body to a substance that the body should not normally react to, and various immune cells are thought to be involved. However, since there are still many unclear points regarding the molecular mechanism of the onset and exacerbation of allergic diseases, and symptomatic treatments are the only treatment methods, interpreting pathological conditions for the radical treatment is desired.

In the Practical Guideline for the Management of Allergic Rhinitis in Japan (Non Patent Literature 1), the cases of selecting drug treatment according to the severity of allergic rhinitis are described by being divided into the cases of perennial allergic rhinitis and seasonal allergic rhinitis.

For mild cases of perennial allergic rhinitis, the first choice is any one of a second-generation antihistamine, a chemical mediator release inhibitor, or a type-2 helper T cell (Th2) cytokine inhibitor, regardless of the disease type. The guideline describes that, in moderate cases, any one of (1) a second-generation antihistamine, (2) a chemical mediator release inhibitor, or (3) a steroid nasal spray is selected for a sneezing and rhinorrhea type, and (3) is used in combination with (1) or (2) as necessary. In severe cases, a second-generation antihistamine is to be used in combination with a steroid nasal spray in a case where sneezing and rhinorrhea are particularly severe, and an antileukotriene drug is used in combination with a steroid nasal spray in patients with severe nasal congestion. In a drug treatment for pollinosis, an initial therapy is recommended for patients showing a severe pollinosis symptom every year, and a drug to be used is selected based on the expected pollen dispersion amount and the disease type and severity during the period in which the symptom is the most severe. Therefore, a second-generation antihistamine and a chemical mediator release inhibitor are to be used for the sneezing and rhinorrhea type, and an antileukotriene drug or the like is to be used for the nasal congestion type. In a case where exacerbation of the symptom occurs with the increase of the pollen dispersion amount, a steroid nasal spray is to be added early, and the treatment regimen is to be stepped up according to the disease type.

It is required that an antiallergic drug allows normal social life and productive activity to be maintained during the administration period thereof, with the importance being placed on preventing drowsiness and cognitive impairment (impaired performance) caused by the administration which limit a social activity, and it is considered that an antiallergic drug is a drug of which safety is prioritized over effectiveness (Non Patent Literature 2). On the other hand, it has been reported that what patients expect the most from an antihistamine is "effectiveness", followed by "safety" and "the number of doses" (Non Patent Literatures 3 and 4). Antihistamines are classified into the first generation and the second generation, and the first-generation antihistamines are fast-acting and have strong effectiveness. However, the effectiveness of the first-generation antihistamines is short-lived, and a central inhibitory effect such as drowsiness is great, since a great amount of the first-generation antihistamines is transferred into brain, which are problematic. Therefore, the first-generation antihistamines are administered with caution to those who drive a car or perform dangerous work.

In addition, since the first-generation antihistamines have an anticholinergic effect, they are required to be used with caution in the cases of glaucoma, prostatic hypertrophy, and an acute bronchial asthma attack (Non Patent Literature 2). On the other hand, although slightly less fast-acting compared to the first generation, the second-generation antihistamines have long effectiveness and less central inhibitory effect and anticholinergic effect. Furthermore, drugs that have shorter time taken to reach the maximum concentration, thus having excellent fast-acting properties, or have further prolonged biological half-life and are effective when administered once a day have been recently developed as late second-generation antihistamines.

Yanai et al. (Non Patent Literature 5) evaluated the histamine H1 receptor occupancy of the first-generation and second-generation antihistamines within brain by positron emission tomography (PET), and classified the antihistamines into three types (20% or less: non-sedating, 20% to 50%: mildly sedating, and 50% or more: sedating) according to the histamine H1 occupancy within the brain by studying the correlations between the histamine H1 occupancy within the brain and indexes such as drowsiness and objective reduction in work efficiency caused by the antihistamines. The classification based on the measurement of the histamine H1 occupancy within brain using PET was adopted as a sedative effect evaluation method in an international conference [Consensus Group on New-Generation Antihistamines (CONGA)] (Non Patent Literature 6), as well as in the Clinical Practice Guidelines for the Management of Atopic Dermatitis by Japanese Dermatological Association in Japan (Non Patent Literature 7). The use of a non-sedating oral antihistamine that does not affect cytochrome P450 (CYP) has been suggested in an international guideline Allergic Rhinitis and its Impact on Asthma (ARIA) (Non Patent Literature 8), and a non-sedating oral antihistamine has also been suggested as the first choice in EAACI/GA2LEN/EDF/WAO16, the guideline for urticaria. Although many non-sedating second-generation antihistamines satisfy the requirements for an ideal antihistamine described in the Practical Guideline for the Management of Allergic Rhinitis in Japan [fast-acting, long-lasting effectiveness, few side effects (drowsiness, reduction in work efficiency, and the like), the capability of being administered over a long period (safety), and good compliance with once- or twice-daily administration] (Non Patent Literature 1), it is known that there exist problems regarding the non-sedating second-generation antihistamines in terms of convenience, such as being influenced by a drug-metabolizing enzyme since an active metabolite is produced through drug metabolism, the need for the administration to patients with a reduced liver or kidney function to be performed with discretion, and the occurrence of interaction with a drug that strengthens a central inhibitory effect, such as alcohol, a sleep-inducing drug, an antianxiety drug, or the like.

As described above, different antiallergic drugs are used according to the severity of the patient, the presence of a complication, the occupation, the age, and the use of a concomitant drug, as well as the lifestyle and the preference and treatment history of the patient. Therefore, the antiallergic drugs are required to be convenient, non-sedating drugs which satisfy all the requirements for an ideal antihistamine, "fast-acting, long-lasting effectiveness, few side effects (drowsiness, reduction in work efficiency, and the like), the capability of being administered over a long period (safety), and good compliance with once- or twice-daily administration", that have not been achieved by conventional antihistamines, and of which the balance between effectiveness and safety is excellent, meeting the medical needs of patients and healthcare professionals.

Furthermore, while previous findings indicate that mast cells (MCs) recognize an antigen (Ag) through a high-affinity IgE receptor (FcεRI) and induce a type I allergic reaction, Yoshida et al. have reported that stimulation of the ion channel P2X4 receptor (P2X4R) potentiates FcεRI-mediated degranulation (Non Patent Literatures 9 and 10). Specifically, the role of the P2X4 receptor in MC degranulation induced by stimulation of an IgE-FcεRI complex by Ag was investigated using bone marrow-derived MCs (BMMCs) prepared from wild type and P2X4 receptor-deficient (P2rx4−/−) mice. As a result, ATP significantly increased Ag-induced degranulation in the BMMCs prepared from the wild-type mice, whereas the Ag-induced degranulation was reduced in the BMMCs prepared from the P2rx4−/− mice. It was also reported that the potentiating effect of ATP was restored by expressing the P2X4 receptor in the P2rx4−/− BMMCs.

However, Non Patent Literature 9 also indicates that the mechanism for the effect of ATP may involve a mechanism other than $Ca^{2+}$ influx through an ion channel activity, and reports that the effect of ATP was not impaired by pretreatment with $Cu^{2+}$, an inhibitor of the P2X4 receptor channel. Thus, how the P2X4 receptor is involved in the degranulation is unknown, and the study does not indicate that an inhibitor of the P2X4 receptor channel has an antiallergic effect.

Patent Literature 1 describes an inhibitor of the P2X4 receptor channel (hereinafter, referred to as a P2X4 receptor antagonist).

However, a compound described in an example in Patent Literature 1 is a selective serotonin reuptake inhibitor, for example, Paroxetine, Fluoxetine, or the like, and has a structure that is completely different from that of a compound of the present application, which is a benzodiazepine derivative compound. Furthermore, only a result of an experiment using a neuropathic pain pathology model in which a nerve injury (L5 spinal nerve injury model) has been performed is shown, and whether the P2X4 receptor antagonist has a treatment effect in an allergy is not determined.

In addition, Patent Literature 2 also discloses a compound exhibiting a P2X4 receptor antagonizing action, however, as in Patent Literature 1, only an effect exhibited by a neuropathic pain model is shown, and whether the compound has a treatment effect in an allergy is unclear.

Moreover, the present applicant has also filed patent applications related to the P2X4 receptor antagonist as in Patent Literatures 3 to 9, however, whether the P2X4 receptor antagonist has a treatment effect in an allergy is unclear in all of the applications.

CITATION LIST

Patent Literature

Patent Literature 1: WO 2008/020651 A
Patent Literature 2: WO 2010/093061 A
Patent Literature 3: WO 2008/023847 A
Patent Literature 4: WO 2012/008478 A
Patent Literature 5: WO 2012/014910 A
Patent Literature 6: WO 2012/017876 A
Patent Literature 7: WO 2013/105608 A
Patent Literature 8: WO 2015/005468 A
Patent Literature 9: WO 2015/005467 A Non Patent Literature Non Patent Literature 1: Committee for Creating Practical Guideline for the Management of Allergic Rhinitis in Japan. Practical Guideline for the Management of Allergic Rhinitis in Japan—Perennial Rhinitis and Pollinosis—2013 edition (revised 7$^{th}$ edition). Tokyo: Life Science; 2013. p 34-63. (Section 5.4.3)

Non Patent Literature 2: Nobuo Kubo. Requirement of the antihistamines. Folia Pharmacol. Jpn. 2005; 125: 279-284. (Section 5.4.9)

Non Patent Literature 3: Masahiro Takigawa, Keiji Iwatsuki, Shinji Shimada, Yoshiki Tokura, Fukumi Furukawa. What Do Patients with Pruritic Skin Disease Expect from Antihistamines (Antiallergic Drugs)?-Patient Questionnaire Survey Results-. Prog. Med. 2006; 26: 2289-2295. (Section 5.4.10)

Non Patent Literature 4: Satoshi Ogino. Patient Satisfaction with the Second-Generation Antihistamines in Pollinosis Treatment—Internet-Based Patient Survey Results (First Report)—. Prog. Med. 2009; 29: 2531-2537. (Section 5.4.11)

Non Patent Literature 5: Yanai K, Zhang D, Tashiro M, Yoshikawa T, Naganuma F, Harada R, et al. Positron emission tomography evaluation of sedative properties of antihistamines. Expert Opin Drug Saf. 2011; 10: 613-622. (Section 5.4.12)

Non Patent Literature 6: Holgate S T, Canonica G W, Simons F E, Taglialatela M, Tharp M, Timmerman H, et al. Consensus Group on New-Generation Antihistamines (CONGA): present status and recommendations. Clin Exp Allergy. 2003; 33: 1305-1324. (Section 5.4.13)

Non Patent Literature 7: Committee for Creating Clinical Practice Guidelines for the Management of Atopic Dermatitis of Japanese Dermatological Association. Clinical Practice Guidelines for the Management of Atopic Dermatitis. Japanese Journal of Dermatology. 2009; 119: 1515-1534. (Section 5.4.5)

Non Patent Literature 8: Brozek J L, Bousquet J, Baena-Cagnani C E, Bonini S, Canonica G W, Casale T B, et al. Allergic Rhinitis and its Impact on Asthma (ARIA) guidelines: 2010 revision. J Allergy Clin Immunol. 2010; 126: 466-476. (Section 5.4.14)

Non Patent Literature 9: Yoshida, K.; Ito, M.; Yamamoto, K.; Koizumi, S.; Tanaka, S.; Furuta, K.; Matsuoka, I. Extracellular ATP augments antigen-induced murine mast cell degranulation and allergic responses via P2X4 receptor activation. J. Immunol. 2019.

Non Patent Literature 10: Yoshida K, et al. Co-Stimulation of Purinergic P2X4 and Prostanoid EP3 Receptors Triggers Synergistic Degranulation in Murine Mast Cells. Int. J. Mol. Sci. 2019, 20, 5157.

SUMMARY OF INVENTION

Technical Problem

An object of the present invention is to provide a pharmaceutical composition useful in preventing, suppressing, or treating a symptom associated with an allergic reaction, and furthermore, to provide a pharmaceutical composition useful in preventing, suppressing, or treating an allergic disease, particularly to provide a pharmaceutical composition useful in preventing, suppressing, or treating a symptom associated with a type I allergic reaction, more particularly to provide a pharmaceutical composition useful in preventing or treating an anaphylactic shock, allergic rhinitis, bronchial asthma, or allergic dermatitis, and even more particularly to provide a pharmaceutical composition useful in suppressing an anaphylactic shock, to provide a pharmaceutical composition useful in preventing or treating pollinosis, and to provide a pharmaceutical composition useful in preventing or treating urticaria or atopic dermatitis.

Solution to Problem

As a result of conducting intensive research in order to achieve the above object, the present inventor found that compounds represented by general formulas (A) to (BII) that have a P2X4 receptor antagonizing action or a pharmaceutically acceptable salt thereof is useful in preventing, suppressing, or treating a symptom associated with an allergic reaction, and furthermore, is useful in preventing, suppressing, or treating an allergic disease, particularly useful in preventing, suppressing, or treating a symptom associated with a type I allergic reaction, more particularly useful in preventing or treating an anaphylactic shock, allergic rhinitis, bronchial asthma, or allergic dermatitis, even more particularly useful in suppressing an anaphylactic shock, and still more particularly useful in preventing or treating pollinosis, urticaria, or atopic dermatitis, thus completing the present invention.

That is, the present invention provides a pharmaceutical composition useful in preventing, suppressing, or treating a symptom associated with an allergic reaction, and furthermore, a pharmaceutical composition useful in preventing, suppressing, or treating an allergic disease, particularly a pharmaceutical composition useful in preventing, suppressing, or treating a symptom associated with a type I allergic reaction, and more particularly a pharmaceutical composition useful in preventing or treating an anaphylactic shock, allergic rhinitis, bronchial asthma, or allergic dermatitis, a pharmaceutical composition useful in suppressing an anaphylactic shock, or a pharmaceutical composition useful in preventing or treating pollinosis, urticaria, or atopic dermatitis, the pharmaceutical composition including a compound having a P2X4 receptor antagonizing action or a pharmaceutically acceptable salt thereof as an active ingredient.

As the compound having a P2X4 receptor antagonizing action, for example, compounds represented by the following general formulas (A) to (BII) can be used. More preferably, as the compound having a P2X4 receptor antagonizing action, the compound represented by the following general formula (BI) or (BII) can be used. It is also possible to use a pharmaceutically acceptable salt of the compounds.

The pharmaceutical composition of the present invention can be used for, for example, preventing, suppressing, or treating a symptom associated with an allergic reaction, and furthermore, for preventing, suppressing, or treating an allergic disease, particularly for preventing, suppressing, or treating a symptom associated with a type I allergic reaction, and more particularly for preventing or treating an anaphylactic shock, allergic rhinitis, bronchial asthma, or allergic dermatitis, for suppressing an anaphylactic shock, or for preventing or treating pollinosis, urticaria, or atopic dermatitis.

From another viewpoint, the present invention provides use of a compound having a P2X4 receptor antagonizing action or a pharmaceutically acceptable salt thereof for producing the pharmaceutical composition; and a method of preventing, suppressing, or treating a symptom associated with an allergic reaction, and furthermore, a method of preventing, suppressing, or treating an allergic disease, particularly a method of preventing, suppressing, or treating a symptom associated with a type I allergic reaction, and more particularly a method of preventing or treating an anaphylactic shock, allergic rhinitis, bronchial asthma, or allergic dermatitis, a method of suppressing an anaphylactic shock, or a method of preventing or treating pollinosis, urticaria, or atopic dermatitis, the method including a step of administering the compound having a P2X4 receptor antagonizing action or a pharmaceutically acceptable salt thereof to a mammal including human at a dose effective for the prevention, suppression, or treatment.

Advantageous Effects of Invention

The pharmaceutical composition of the present invention is useful as a pharmaceutical composition useful in preventing, suppressing, or treating a symptom associated with an allergic reaction, and furthermore, is useful as a pharmaceutical composition useful in preventing, suppressing, or treating an allergic disease, particularly useful as a pharmaceutical composition useful in preventing, suppressing, or treating a symptom associated with a type I allergic reaction, and more particularly useful as a pharmaceutical composition useful in preventing or treating an anaphylactic shock, allergic rhinitis, bronchial asthma, or allergic dermatitis, a pharmaceutical composition useful in suppressing an anaphylactic shock, or a pharmaceutical composition useful in preventing or treating pollinosis, urticaria, or atopic dermatitis, each of which is expected to be highly effective.

DESCRIPTION OF EMBODIMENTS

Figure 1:
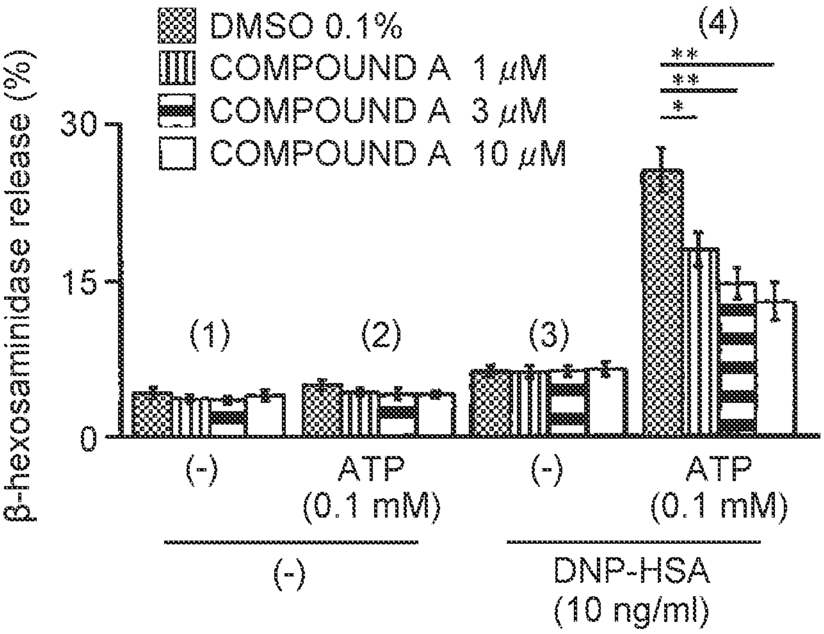
FIG. 1 is a diagram obtained by observing a suppressive effect of Compound A on a degranulation reaction caused by costimulation of IgE-sensitized BMMCs with DNP-HSA and ATP.

A pharmaceutical composition of the present invention can be used as a pharmaceutical composition useful in preventing, suppressing, or treating a symptom associated with an allergic reaction, and can also be used as a pharmaceutical composition for the following use.

The pharmaceutical composition of the present invention can be used as a pharmaceutical composition useful in preventing, suppressing, or treating an allergic disease.

The pharmaceutical composition of the present invention can be used as a pharmaceutical composition useful in preventing, suppressing, or treating a symptom associated with a type I allergic reaction.

The pharmaceutical composition of the present invention can be used as a pharmaceutical composition useful in preventing or treating an anaphylactic shock.

The pharmaceutical composition of the present invention can be used as a pharmaceutical composition useful in preventing or treating allergic rhinitis.

The pharmaceutical composition of the present invention can be used as a pharmaceutical composition useful in preventing or treating bronchial asthma.

The pharmaceutical composition of the present invention can be used as a pharmaceutical composition useful in preventing or treating allergic dermatitis.

The pharmaceutical composition of the present invention can be used as a pharmaceutical composition useful in suppressing an anaphylactic shock.

The pharmaceutical composition of the present invention can be used as a pharmaceutical composition useful in preventing or treating pollinosis.

The pharmaceutical composition of the present invention can be used as a pharmaceutical composition useful in preventing or treating urticaria.

The pharmaceutical composition of the present invention can be used as a pharmaceutical composition useful in preventing or treating atopic dermatitis.

As another aspect, the pharmaceutical composition of the present invention can be used as a pharmaceutical composition for the following use.

The pharmaceutical composition of the present invention can be used as a pharmaceutical composition for preventing, suppressing, or treating the symptom associated with an allergic reaction which is accompanied by inflammation.

The pharmaceutical composition of the present invention can be used as a pharmaceutical composition for preventing, suppressing, or treating the symptom associated with an allergic reaction which is accompanied by release of secretory granules within mast cells to the outside of the cells.

The "symptom associated with an allergic reaction" in the present specification includes an allergic disease (alternatively referred to as an allergy disease). The "allergic disease" in the present specification refers to a disease caused by an allergy.

In the present specification, the term "prevention" is a concept including preventing onset of a "diseased" or "abnormal" symptom, state, or disease before an outbreak thereof and an action or a method therefor.

In the present specification, the term "treatment" is a concept including eliminating, completely curing, healing, or remitting a "diseased" or "abnormal" symptom, state, or disease and an action or a method therefor, suppressing exacerbation of a "diseased" or "abnormal" symptom, state, or disease and an action or a method therefor, and improvement. Here, the term "improvement" is a concept including approach of a "diseased" or "abnormal" symptom, state, or disease to a "healthy" or "normal" state or an action or a method therefor, and causing a "diseased" or "abnormal" symptom, state, or disease to be in a "healthy" or "normal" state or an action or a method therefor. Therefore, the term "improvement" in one embodiment includes a concept in which a numerical value which serves as an index of a "diseased" or "abnormal" symptom or state becomes small or large so as to approach a normal value or be the normal value in accordance with the "improvement". Furthermore, the term "suppression" is a concept including stopping or slowing down exacerbation or progression of a symptom, state, or disease and an action or a method therefor, and improving the symptom, state, or disease or an action or a method therefor. Here, the term "improvement" has the meaning described above. The expression "exacerbation or progression of symptom, state, or disease" includes exacerbation or progression of a "diseased" or "abnormal" symptom, state, or disease and exacerbation or progression from a "healthy" or "normal" state to a "diseased" or "abnormal" symptom, state, or disease. The term "suppression" in one embodiment is stopping or slowing down exacerbation or progression of a symptom, state, or disease or an action or a method therefor. The term "suppression" in another embodiment means stopping or slowing down exacerbation or progression of a symptom, state, or disease.

The term "treatment" in one embodiment means eliminating, completely curing, healing, or remitting a "diseased" or "abnormal" symptom, state, or disease and an action or a method therefor. The term "treatment" in another embodiment is eliminating, completely curing, healing, or remitting a "diseased" or "abnormal" symptom, state, or disease.

In the present specification, the symptom, state, or disease, or a numerical value, a state, or a function serving as indices of these can be evaluated by comparison of the indices before and after administration of the medicament provided by the present invention or by comparison of the indices between a group to which a placebo or a control that does not contain the medicament provided by the present invention is administered and a group to which the medicament provided by the present invention is administered.

As an active ingredient of the pharmaceutical composition of the present invention, compounds represented by the following general formulas (A) to (BII) or a pharmaceutically acceptable salt thereof can be used.

Symbols used in the tables below and the like are as follows. Me: methyl group, Et: ethyl group, Pr: n-propyl group, iPr: isopropyl group, tBu: tert-butyl group, Ac: acetyl group, Ph: phenyl group In the tables below and the like, a substituent may be marked together with a position number indicating a substitution position of the substituent. In addition, in order to distinguish position numbers of positions that appear to be identical to each other in a chemical formula, one position number may be indicated with a prime symbol "'" for convenience, however, as long as a definitive structure for a compound name can be specified, position numbers may be indicated without using the prime symbol.

(A-1) A compound represented by the following general formula (A) or a pharmaceutically acceptable salt thereof:

[Formula 1]

(A)

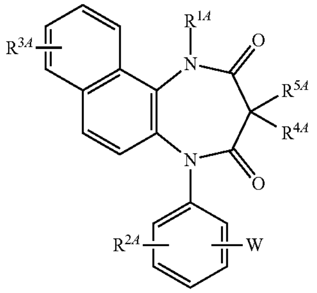

(in the formula, $R^{1A}$ represents a hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, or an alkyl group having 1 to 3 carbon atoms and substituted with a phenyl group;

$R^{2A}$ and $R^{3A}$ may be the same or different, and represent a hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, a carboxyl group, an acyl group having 2 to 8 carbon atoms, an alkoxycarbonyl group (the alkoxy moiety has 1 to 8 carbon atoms), a carbamoyl group, an alkylthio group having 1 to 8 carbon atoms, an alkylsulfinyl group having 1 to 8 carbon atoms, an alkylsulfonyl group having 1 to 8 carbon atoms, or a sulfamoyl group;

$R^{4A}$ and $R^{5A}$ may be the same or different, and represent a hydrogen atom, an alkyl group having 1 to 8 carbon atoms, an alkyl group having 1 to 8 carbon atoms and substituted with 1 to 3 halogen atoms, or an alkyl group having 1 to 3 carbon atoms and substituted with a phenyl group; and $W^{A}$ represents a five or six membered heterocyclic ring comprising 1 to 4 nitrogen atoms as the members of the ring, which may have a substituent)

In the general formula (A), examples of the alkyl group having 1 to 8 carbon atoms represented by $R^{1A}$, $R^{2A}$, $R^{3A}$, $R^{4A}$, and $R^{5A}$ can comprise a methyl group, an ethyl group, a propyl group, an isopropyl group, a butyl group, an i-butyl group, a t-butyl group, a pentyl group, a hexyl group, and the like.

Examples of the alkenyl group having 2 to 8 carbon atoms represented by $R^{1A}$ can comprise an allyl group and the like.

Examples of the alkyl group having 1 to 8 carbon atoms and substituted with 1 to 3 halogen atoms represented by $R^{1A}$, $R^{2A}$, $R^{3A}$, $R^{4A}$, and $R^{5A}$ or $R^{11A}$, $R^{12A}$, $R^{13A}$, $R^{14A}$, and $R^{15A}$ can comprise a methyl group, an ethyl group, a propyl group, an isopropyl group, a butyl group, a t-butyl group, and the like substituted with 1 to 3 halogen atoms such as a fluorine atom, a chlorine atom, and a bromine atom, and preferable examples thereof can comprise a trifluoromethyl group, a chloromethyl group, a 2-chloroethyl group, a 2-bromoethyl group, a 2-fluoroethyl group, and the like.

Examples of the alkyl group having 1 to 3 carbon atoms and substituted with a phenyl group represented by $R^{1A}$, $R^{4A}$, and $R^{5A}$ can comprise a benzyl group and the like.

Examples of the alkoxy group having 1 to 8 carbon atoms represented by $R^{2A}$ and $R^{3A}$ can comprise a methoxy group, an ethoxy group, a propoxy group, an isopropoxy group, a butoxy group, an i-butoxy group, a t-butoxy group, a pentyloxy group, a hexyloxy group, and the like.

Examples of the alkoxy group having 1 to 8 carbon atoms and substituted with 1 to 3 halogen atoms represented by $R^{2A}$ and $R^{3A}$ can comprise a methyl group, an ethyl group, a propyl group, an isopropyl group, a butyl group, a t-butyl group, and the like substituted with 1 to 3 halogen atoms such as a fluorine atom, a chlorine atom, and a bromine atom, and preferable examples thereof can comprise a trifluoromethoxy group, a 2-chloroethoxy group, a 2-bromoethoxy group, a 2-fluoroethoxy group, and the like.

Examples of the halogen atom represented by $R^{2A}$ and $R^{3A}$ can comprise a fluorine atom, a chlorine atom, a bromine atom, and the like.

Examples of the alkylamino group having 1 to 8 carbon atoms represented by $R^{2A}$ and $R^{3A}$ can comprise a methylamino group, an ethylamino group, and the like.

Examples of the dialkylamino group having 1 to 8 carbon atoms represented by $R^{2A}$ and $R^{3A}$ can comprise a dimethylamino group, a diethylamino group, and the like.

Examples of the acylamino group having 2 to 8 carbon atoms represented by $R^{2A}$ and $R^{3A}$ can comprise an acetylamino group.

Examples of the acylamino group having 2 to 8 carbon atoms and substituted with 1 to 3 halogen atoms represented by $R^{2A}$ and $R^{3A}$ can comprise a trifluoromethylcarbonylamino group.

Examples of the alkylsulfonylamino group having 1 to 8 carbon atoms represented by $R^{2A}$ and $R^{3A}$ can comprise a methylsulfonylamino group.

Examples of the acyl group having 2 to 8 carbon atoms represented by $R^{2A}$ and $R^{3A}$ can comprise an acetyl group.

Examples of the alkoxycarbonyl group (the alkoxy moiety has 1 to 8 carbon atoms) represented by $R^{2A}$ and $R^{3A}$ can comprise a methoxycarbonyl group, an ethoxycarbonyl group, and the like.

Examples of the alkylthio group having 1 to 8 carbon atoms represented by $R^{2A}$ and $R^{3A}$ can comprise a methylthio group.

Examples of the alkylsulfinyl group having 1 to 8 carbon atoms represented by $R^{2A}$ and $R^{3A}$ can comprise a methylsulfinyl group.

Examples of the alkylsulfonyl group having 1 to 8 carbon atoms represented by $R^{2A}$ and $R^{3A}$ can comprise a methylsulfonyl group.

Examples of the five or six membered heterocyclic ring comprising 1 to 4 nitrogen atoms as the members of the ring, which may have a substituent, represented by $W^A$ can comprise tetrazole, 1,2,4-triazole, 1,2,3-triazole, 1,2,4-oxadiazole, pyrazole, imidazole, oxazole, isoxazole, pyrrole, thiazole, pyridine, and pyrrolidine.

Examples of the substituent that may be comprised in the five or six membered heterocyclic ring comprising 1 to 4 nitrogen atoms as the members of the ring, which may have a substituent, represented by $W^A$ can comprise an alkyl group having 1 to 8 carbon atoms such as a methyl group and an ethyl group, an alkyl group having 1 to 8 carbon atoms and substituted with 1 to 3 halogen atoms such as a trifluoromethyl group, a halogen atom such as a fluorine atom, a cyano group, an oxo group, a thioxo group, and the like.

$R^{2A}$ and $R^{3A}$ in the general formula (A) may have 1 to 3 same or different ones in the benzene ring substituted by $R^{2A}$ and $R^{3A}$.

As the compound represented by the general formula (A), the following compounds are preferable.

(A-2) The compound according to (A-1), in which $W^A$ represents tetrazole, 1,2,4-triazole, 1,2,3-triazole, 1,2,4-oxadiazole, pyrazole, or imidazole that may have a substituent selected from an alkyl group having 1 to 8 carbon atoms, an alkyl group having 1 to 8 carbon atoms and substituted with 1 to 3 halogen atoms, a halogen atom, a cyano group, an oxo group, and a thioxo group.

(A-3) The compound according to (A-1) or (A-2), in which $W^A$ represents tetrazole, 1,2,4-triazole, or 1,2,3-triazole that may have a substituent selected from an alkyl group having 1 to 8 carbon atoms, an alkyl group having 1 to 8 carbon atoms and substituted with 1 to 3 halogen atoms, a halogen atom, and a cyano group.

(A-4) The compound according to any one of (A-1) to (A-3), in which $W^A$ represents 5-oxo-1,2,4-oxadiazole or 5-thioxo-1,2,4-oxadiazole.

(A-5) The compound according to any one of (A-1) to (A-4), in which $W^A$ represents tetrazole.

(A-6) The compound according to any one of (A-1) to (A-5), in which $R^{1A}$ represents a hydrogen atom or an alkyl group having 1 to 8 carbon atoms.

(A-7) The compound according to any one of (A-1) to (A-6), in which $R^{1A}$ represents a hydrogen atom.

(A-8) The compound according to any one of (A-1) to (A-7), in which $R^{4A}$ represents a hydrogen atom, and $R^{5A}$ represents a hydrogen atom or an alkyl group having 1 to 8 carbon atoms.

(A-9) The compound according to any one of (A-1) to (A-8), in which $R^{4A}$ and $R^{5A}$ both represent hydrogen atoms.

(A-10) The compound according to any one of (A-1) to (A-9), in which $R^{2A}$ represents a hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, a carboxyl group, an acyl group having 2 to 8 carbon atoms, or an alkoxycarbonyl group (the alkoxy moiety has 1 to 8 carbon atoms).

(A-11) The compound according to any one of (A-1) to (A-10), in which $R^{2A}$ represents a hydrogen atom.

(A-12) The compound according to any one of (A-1)(A-11), in which $R^{3A}$ represents a hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, a carboxyl group, an acyl group having 2 to 8 carbon atoms, or an alkoxycarbonyl group (the alkoxy moiety has 1 to 8 carbon atoms).

(A-13) The compound according to any one of (A-1) to (A-12), in which $R^{3A}$ represents a hydrogen atom.

Examples of the pharmaceutically acceptable salt of the compound represented by the general formula (A) can comprise hydrochloride and the like, in a case where $R^{2A}$ and $R^{3A}$ in the general formula (A) represent amino groups or the like. In addition, in a case where $R^{2A}$ and $R^{3A}$ in the general formula (A) represent carboxyl groups, examples of the pharmaceutically acceptable salt of the compound represented by the general formula (A) can comprise a salt of an alkali metal such as sodium, potassium, and lithium.

Typical compounds comprised in the compounds represented by the general formula (A) are as follows.

<Typical Compound A-100>

[Formula 2]

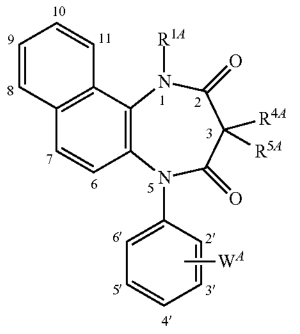

($R_{1A}$, $R^{4A}$, $R^{5A}$, and $W^A$ in the formula and a substitution position of $W^A$ are indicated in Tables 1 to 3)

In Tables 1 to 3, the substitution position of $W^A$ indicates a substitution position on a benzene ring. That is, positions 2, 3, and 4 in the tables correspond to positions 2', 3', and 4' in a formula of Typical Compound A-100, respectively.

TABLE 1

| $R^1$ | Position of W | W | $R^4/R^5$ |
|---|---|---|---|
| H | 2- | 1H-tetrazol-5-yl | H/H |
| H | 3- | 1H-tetrazol-5-yl | H/H |
| H | 3- | (1-methyl-1H-tetrazol)-5-yl | H/H |
| H | 4- | 1H-tetrazol-5-yl | H/H |
| $CH_3$ | 3- | 1H-tetrazol-5-yl | H/H |
| $CH_3$ | 3- | 1H-tetrazol-5-yl | $CH_3$/H |
| benzyl | 3- | 1H-tetrazol-5-yl | H/H |
| H | 3- | 1H-tetrazol-1-yl | H/H |
| H | 3- | 1H-tetrazol-1-yl | $CH_3/CH_3$ |
| H | 3- | (1,2,3-triazol)-5-yl | H/H |
| H | 3- | (1,2,4-triazol)-3-yl | H/H |
| H | 4- | (1,2,4-triazol)-3-yl | H/H |

TABLE 2

| $R^1$ | Position of W | W | $R^4/R^5$ |
|---|---|---|---|
| H | 2- | (1,2,4-triazol)-1-yl | H/H |
| H | 3- | (1,2,4-triazol)-1-yl | H/H |
| H | 3- | [5-(trifluoromethyl)-1,2,4-triazol]-3-yl | H/H |
| H | 3- | [5-(trifluoromethyl)-1,2,4-triazol]-3-yl | ethyl/H |
| H | 3- | [5-fluoro-1,2,3-triazol]-4-yl | H/H |
| H | 3- | [5-fluoro-1,2,3-triazol]-4-yl | $CH_3/CH_3$ |
| H | 3- | [5-cyano-1,2,3-triazol]-4-yl | H/H |
| H | 4- | 1H-imidazol-1-yl | H/H |
| H | 4- | 1H-imidazol-1-yl | Pr/H |
| H | 3- | 1H-imidazol-2-yl | H/H |
| H | 3- | 1H-imidazol-4-yl | H/H |
| H | 3- | imidazolin-2-yl | H/H |

TABLE 3

| $R^1$ | Position of W | W | $R^4/R^5$ |
|---|---|---|---|
| H | 2- | pyrazol-3-yl | H/H |
| H | 3- | pyrazol-4-yl | H/H |
| H | 3- | pyrazol-5-yl | $CH_3/H$ |
| H | 3- | (1,2,4-oxadiazol)-3-yl | H/H |
| H | 3- | (1,3,4-oxadiazol)-2-yl | H/H |
| H | 3- | (5-oxo-1,2,4-oxadiazol)-3-yl | H/H |
| H | 3- | pyrrol-1-yl | H/H |
| H | 4- | pyrrolidin-2-yl | H/H |
| $CH_3$ | 4- | pyrrolidin-2-yl | $CH_3/H$ |
| H | 4- | (1,3-oxazol)-5-yl | H/H |
| H | 3- | (1,3-oxazol)-5-yl | H/H |
| H | 2- | (1,3-thiazol)-5-yl | H/H |

<Typical Compound A-200>

[Formula 3]

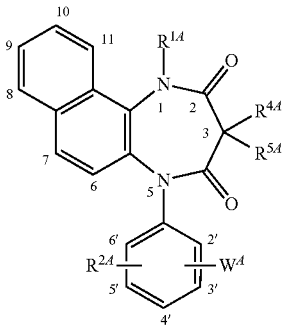

($R^{1A}$, $R^{2A}$, $R^{4A}$, $R^{5A}$, and $W^A$ in the formula and a substitution position of $W^A$ are indicated in Tables 4 and 5)

In Tables 4 and 5, the substitution position of $W^A$ indicates a substitution position on a benzene ring. That is, positions 2, 3, and 4 in the tables correspond to positions 2', 3', and 4' in a formula of Typical Compound A-200, respectively.

TABLE 4

| $R^1$ | $R^2$ | Position of W | W | $R^4/R^5$ |
|---|---|---|---|---|
| H | 4-OH | 3- | 1H-tetrazol-5-yl | H/H |
| H | 4-$OCH_3$ | 3- | 1H-tetrazol-5-yl | H/H |
| $CH_3$ | 2-Cl | 3- | 1H-tetrazol-5-yl | H/H |
| H | 2,6-Cl | 3- | 1H-tetrazol-5-yl | H/H |

TABLE 4-continued

| $R^1$ | $R^2$ | Position of W | W | $R^4/R^5$ |
|---|---|---|---|---|
| H | 4-F | 3- | 1H-tetrazol-5-yl | H/H |
| H | 4-Br | 3- | 1H-tetrazol-5-yl | ethyl/H |
| H | 3-$OCH_3$ | 4- | (1-methyl-1H-tetrazol)-5-yl | H/H |
| H | 4-$CH_3$ | 3- | 1H-tetrazol-5-yl | H/H |

TABLE 5

| $R^1$ | $R^2$ | Position of W | W | $R^4/R^5$ |
|---|---|---|---|---|
| H | 4-Cl | 3- | (1,2,3-triazol)-5-yl | $CH_3/H$ |
| H | 4-$CF_3$ | 3- | (1,2,3-triazol)-5-yl | H/H |
| H | 3-$SCH_3$ | 4- | (1,2,4-triazol)-1-yl | H/H |
| H | 3-$SO_2CH_3$ | 4- | 1H-imidazol-1-yl | H/H |
| H | 3-$NHSO_2CH_3$ | 4- | 1H-imidazol-1-yl | H/H |
| H | 4-$OCH_3$ | 3- | 1H-imidazol-4-yl | H/H |
| H | 4-F | 2- | pyrazol-3-yl | H/H |

<Typical Compound A-300>

[Formula 4]

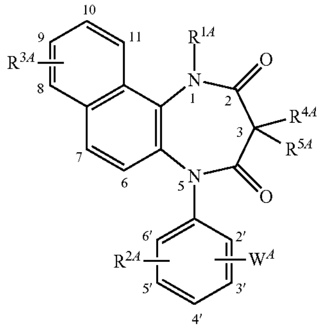

($R^{1A}$, $R^{2A}$, $R^{3A}$, $R^{4A}$, $R^{5A}$ and $W^A$ in the formula and a substitution position of $W^A$ are indicated in Tables 6 and 7)

In Tables 6 and 7, the substitution position of $W^A$ indicates a substitution position on a benzene ring. That is, positions 3 and 4 in the tables correspond to positions 3' and 4' in a formula of Typical Compound A-300, respectively.

TABLE 6

| $R^1$ | $R^2$ | Position of W | W | $R^3$ | $R^4/R^5$ |
|---|---|---|---|---|---|
| H | H | 3- | 1H-tetrazol-5-yl | 9-Br | H/H |
| H | 4-$OCH_3$ | 3- | 1H-tetrazol-5-yl | 9-Cl | H/H |
| H | 4-OH | 3- | 1H-tetrazol-5-yl | 10-$OCH_3$ | H/H |
| H | 2-Cl | 3- | 1H-tetrazol-5-yl | 9-Br | H/H |
| H | 2,6-Cl | 3- | 1H-tetrazol-5-yl | 9-$CH_3$ | H/H |
| H | H | 3- | 1H-tetrazol-5-yl | 10-Cl | $CH_3/H$ |
| H | 3-$OCH_3$ | 4- | (1-methyl-1H-tetrazol)-5-yl | 9-$CF_3$ | H/H |

TABLE 7

| $R^1$ | $R^2$ | Po-si--tion of W | W | $R^3$ | $R^4/R^5$ |
|---|---|---|---|---|---|
| H | 4-$CH_3$ | 3- | 1H-tetrazol-1-yl | 9-CN | Pr/H |
| $CH_3$ | H | 3- | (1,2,3-triazol)-5-yl | 9-OH | H/H |
| ethyl | H | 3- | (1,2,3-triazol)-5-yl | 10-F | H/H |
| H | 3-Br | 4- | (1,2,4-triazol)-1-yl | 9-$SCH_3$ | H/H |

TABLE 7-continued

| $R^1$ | $R^2$ | Po-si--tion of W | W | $R^3$ | $R^4/R^5$ |
|---|---|---|---|---|---|
| allyl | H | 4- | 1H-imidazol-1-yl | 8-$OCH_3$ | H/H |
| H | H | 3- | 1H-imidazol-1-yl | 10-$OCH_3$ | $CH_3/CH_3$ |

(B-1) A compound represented by the following general formula (BI) or a pharmaceutically acceptable salt thereof:

[Formula 5]

(BI)

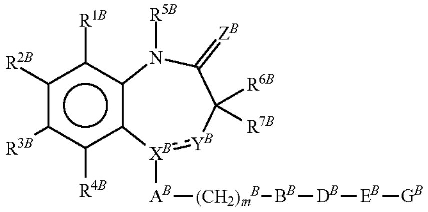

(in the formula, $R^{1B}$ and $R^{2B}$ may be the same or different, and represent a hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (the alkoxy moiety has 1 to 8 carbon atoms), a phenyl group which may be substituted, a pyridyl group which may be substituted, or an aralkyl group (the aryl moiety has 6 to 10 carbon atoms, and the alkylene moiety has 1 to 8 carbon atoms), or $R^{1B}$ and $R^{2B}$ may bind together to form a condensed ring selected from a naphthalene ring, a quinoline ring, an isoquinoline ring, a tetrahydronaphthalene ring, an indane ring, a tetrahydroquinoline ring, and a tetrahydroisoquinoline ring together with the benzene ring to which they bind, and the ring constituted by $R^{1B}$ and $R^{2B}$ bound to each other, together with the carbon atoms to which $R^{1B}$ and $R^{2B}$ bind may be substituted with 1 to 4 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (the alkoxy moiety has 1 to 8 carbon atoms), and an aralkyl group (the aryl moiety has 6 to 10 carbon atoms, and the alkylene moiety has 1 to 8 carbon atoms), $R^{3B}$ and $R^{4B}$ may be the same or different, and represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (the alkoxy moiety has 1 to 8 carbon atoms), or an aralkyl group (the aryl moiety has 6 to 10 carbon atoms, and the alkylene moiety has 1 to 8 carbon atoms), $R^{5B}$ represents a hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with a hydroxyl group, or an aralkyl group (the aryl moiety has 6 to 10 carbon atoms, and the alkylene moiety has 1 to 8 carbon atoms), $R^{6B}$ and $R^{7B}$ may be the same or different, and represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, or an amino group, $X^B$ represents C, CH, or N, $Y^B$ represents N, NH, or C(=O), provided that when $X^B$ is N, $Y^B$ is not N or NH, and when $X^B$ is C or CH, $Y^B$ is not C(=O), the double line consisting of the solid line and the broken line represents a single bond or a double bond, $Z^B$ represents an oxygen atom or a sulfur atom, $A^B$ represents a benzene ring, a pyridine ring, a thiophene ring, a pyrimidine ring, a naphthalene ring, a quinoline ring, or an indole ring, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an aralkyl group (the aryl moiety has 6 to 10 carbon atoms, and the alkylene moiety has 1 to 8 carbon atoms), a phenyl group, and a pyridyl group, as a substituent, or represents an atomic bond, $B^B$ represents $N(R^{8B})C(=O)$, NHCONH, $CON(R^{9B})$, NHC(=S)NH, $N(R^{10B})SO_2$, $SO_2N(R^{11B})$, or $OSO_2$, wherein $R^{8B}$, $R^{9B}$, $R^{10B}$, and $R^{11B}$ represent a hydrogen atom, an alkyl group having 1 to 8 carbon atoms, an alkyl group having 1 to 8 carbon atoms and substituted with 1 to 3 halogen atoms, an alkyl group having 1 to 8 carbon atoms and substituted with a hydroxyl group, or an aralkyl group (the aryl moiety has 6 to 10 carbon atoms, and the alkylene moiety has 1 to 8 carbon atoms), $D^B$ represents an alkylene chain having 1 to 6 carbon atoms, which may have 1 to 4 of the same or different substituents selected from an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with a hydroxyl group, and an aralkyl group (the aryl moiety has 6 to 10 carbon atoms, and the alkylene moiety has 1 to 8 carbon atoms), as a substituent, and may further have a double bond, or represents an atomic bond, $E^B$ represents O, S, $NR^{12B}$, or an atomic bond, wherein $R^{12B}$ represents a hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with a hydroxyl group, or an aralkyl group (the aryl moiety has 6 to 10 carbon atoms, and the alkylene moiety has 1 to 8 carbon atoms), $G^B$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, an alkylsulfonyl group having 1 to 6 carbon atoms, an aralkyl group (the aryl moiety has 6 to 10 carbon atoms, and the alkylene moiety has 1 to 8 carbon atoms), a phenyl group which may be substituted, a pyridyl group which may be substituted, an imidazolyl group which may be substituted, an oxazolyl group which may be substituted, and a thiazolyl group which may be substituted, as a substituent, and $m^B$ represents an integer of 0 to 5, provided that when $R^{1B}$ and $R^{2B}$ do not bind together to form a ring, those compounds are excluded wherein, $X^B$ is C, $Y^B$ is N, the double line consisting of the solid line and the broken line is a double bond, $Z^B$ is an oxygen atom, $A^B$ is a benzene ring, $m^B$ is 0, $B^B$ is C(=O)NH, $E^B$ is an atomic bond, and $G^B$ is a phenyl group).

(B-2) A compound represented by the following general formula (BII) or a pharmaceutically acceptable salt thereof:

[Formula 6]

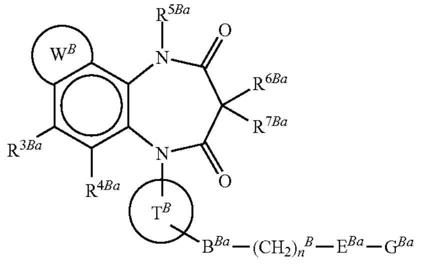

(BII)

(In the formula,

[Formula 7]

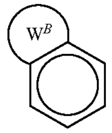

represents a naphthalene ring, a quinoline ring, an isoquinoline ring, a tetrahydronaphthalene ring, an indane ring, a tetrahydroquinoline ring, or a tetrahydroisoquinoline ring, and these rings may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (the alkoxy moiety has 1 to 8 carbon atoms), and an aralkyl group (the aryl moiety has 6 to 10 carbon atoms, and the alkylene moiety has 1 to 8 carbon atoms), $R^{3Ba}$ and $R^{4Ba}$ may be the same or different, and represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (the alkoxy moiety has 1 to 8 carbon atoms), or an aralkyl group (the aryl moiety has 6 to 10 carbon atoms, and the alkylene moiety has 1 to 8 carbon atoms), $R^{5Ba}$ represents a hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with a hydroxyl group, or an aralkyl group (the aryl moiety has 6 to 10 carbon atoms, and the alkylene moiety has 1 to 8 carbon atoms), $R^{6Ba}$ and $R^{7Ba}$ may be the same or different, and represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, or an amino group,

[Formula 8]

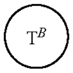

represents a benzene ring, a pyridine ring, a thiophene ring, a pyrimidine ring, a naphthalene ring, a quinoline ring, or an indole ring, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an aralkyl group (the aryl moiety has 6 to 10 carbon atoms, and the alkylene moiety has 1 to 8 carbon atoms), a phenyl group, and a pyridyl group, as a substituent, $B^{Ba}$ represents $N(R^{8Ba})C(=O)$, NHCONH, $CON(R^{9Ba})$, NHC(=S) NH, $N(R^{10Ba})SO_2$, $SO_2N(R^{11Ba})$, or $OSO_2$, wherein $R^{8Ba}$, $R^{9Ba}$, $R^{10Ba}$, and $R^{11Ba}$ represent a hydrogen atom, an alkyl group having 1 to 8 carbon atoms, an alkyl group having 1 to 8 carbon atoms and substituted with 1 to 3 halogen atoms, an alkyl group having 1 to 8 carbon atoms and substituted with a hydroxyl group, or an aralkyl group (the aryl moiety has 6 to 10 carbon atoms, and the alkylene moiety has 1 to 8 carbon atoms), $E^{Ba}$ represents O, S, $NR^{12Ba}$, or an atomic bond, wherein $R^{12Ba}$ represents a hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with a hydroxyl group, or an aralkyl group (the aryl moiety has 6 to 10 carbon atoms, and the alkylene moiety has 1 to 8 carbon atoms), $G^{Ba}$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine, which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, an alkylsulfonyl group having 1 to 6 carbon atoms, an aralkyl group (the aryl moiety has 6 to 10 carbon atoms, and the alkylene moiety has 1 to 8 carbon atoms), a phenyl group which may be substituted, a pyridyl group which may be substituted, an imidazolyl group which may be substituted, an oxazolyl group which may be substituted, and a thiazolyl group which may be substituted, as a substituent, and $n^B$ represents an integer of 0 to 5).

Next, the substituents in the general formulas (BI) and (BII) of the present specification is described.

Examples of the alkyl group having 1 to 8 carbon atoms can comprise a methyl group, an ethyl group, a propyl group, an isopropyl group, a butyl group, an i-butyl group, a t-butyl group, a pentyl group, a hexyl group, and the like.

Examples of the cycloalkyl group having carbon atoms 3 to 8 can comprise a cyclopropyl group, a cyclohexyl group, and the like.

Examples of the alkenyl group having 2 to 8 carbon atoms can comprise an allyl group, and the like.

Examples of the alkoxy group having 1 to 8 carbon atoms can comprise a methoxy group, an ethoxy group, a propoxy group, an isopropoxy group, a butoxy group, an i-butoxy group, a t-butoxy group, a pentyloxy group, a hexyloxy group, and the like.

Examples of the alkyl group having 1 to 8 carbon atoms and substituted with 1 to 3 halogen atoms can comprise a methyl group, an ethyl group, a propyl group, an isopropyl group, a butyl group, a t-butyl group, and the like substituted with 1 to 3 halogen atoms such as a fluorine atom, a chlorine atom, and a bromine atom, and preferable examples thereof can comprise a trifluoromethyl group, a chloromethyl group, a 2-chloroethyl group, a 2-bromoethyl group, a 2-fluoroethyl group, and the like.

Examples of the alkoxy group having 1 to 8 carbon atoms substituted with 1 to 3 halogen atoms can comprise a methoxy group, an ethoxy group, a propoxy group, an isopropoxy group, a butoxy group, a t-butoxy group, and the like substituted with 1 to 3 halogen atoms such as a fluorine atom, a chlorine atom, and a bromine atom, and preferable examples thereof can comprise a trifluoromethoxy group, a chloromethoxy group, a 2-chloroethoxy group, a 2-bromoethoxy group, a 2-fluoroethoxy group, and the like.

Examples of the halogen atom can comprise a fluorine atom, a chlorine atom, a bromine atom, and the like.

Examples of the alkylamino group having 1 to 8 carbon atoms can comprise a methylamino group, an ethylamino group, and the like.

Examples of the dialkylamino group having 2 to 8 carbon atoms can comprise a dimethylamino group, a diethylamino group, and the like.

Examples of the acylamino group having 2 to 8 carbon atoms can comprise an acetylamino group and the like.

Examples of the acyl group having 2 to 8 carbon atoms can comprise an acetyl group and the like.

Examples of the alkoxycarbonyl group (the alkoxy moiety has 1 to 8 carbon atoms) can comprise a methoxycarbonyl group and the like.

Examples of the aralkyl group (the aryl moiety has 6 to 10 carbon atoms, and the alkylene moiety has 1 to 8 carbon atoms) can comprise a benzyl group and the like.

Examples of the alkyl group having 1 to 8 carbon atoms and substituted with a hydroxyl group can comprise a 2-hydroxyethyl group and the like.

Examples of the alkylsulfinyl group having 1 to 6 carbon atoms can comprise a methanesulfinyl group and the like.

Examples of the alkylthio group having 1 to 6 carbon atoms can comprise a methylthio group and the like.

Examples of the alkylsulfonyl group having 1 to 6 carbon atoms can comprise a methanesulfonyl group and the like.

Examples of the substituent that may be comprised in the phenyl group which may be substituted, the pyridyl group which may be substituted, the imidazolyl group which may be substituted, the oxazolyl group which may be substituted, and the thiazolyl group which may be substituted can comprise a halogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, and the like.

As the compound represented by the general formula (BI), the following compounds are preferable.

(B-1-1)

The compound according to (B-1), in which $R^{1B}$ and $R^{2B}$ may be the same or different, and represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, a phenyl group which may be substituted, a pyridyl group which may be substituted, or an aralkyl group (the aryl moiety has 6 to 10 carbon atoms, and the alkylene moiety has 1 to 8 carbon atoms).

(B-1-2)

The compound according to (B-1) or (B-1-1), in which $R^{1B}$ and $R^{2B}$ bind together to form a naphthalene ring or a tetrahydronaphthalene ring together with the benzene ring to which they bind, and the benzene ring or the cyclohexene ring constituted by $R^{1B}$ and $R^{2B}$, bound to each other, together with the carbon atoms to which $R^{1B}$ and $R^{2B}$ bind may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (the alkoxy moiety has 1 to 8 carbon atoms), and an aralkyl group (the aryl moiety has 6 to 10 carbon atoms, and the alkylene moiety has 1 to 8 carbon atoms), (B-1-3)

The compound according to (B-1) or (B-1-1), in which $R^{1B}$ and $R^{2B}$ bind together to form a naphthalene ring together with the benzene ring to which they bind, and the benzene ring constituted by $R^{1B}$ and $R^{2B}$, bound to each other, together with the carbon atoms to which $R^{1B}$ and $R^{2B}$ bind may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, and an amino group.

(B-1-4)

The compound according to (B-1) or (B-1-1), in which $R^{1B}$ and $R^{2B}$ bind together to form a naphthalene ring or a tetrahydronaphthalene ring together with the benzene ring to which they bind.

(B-1-5)

The compound according to any one of (B-1) and (B-1-1) to (B-1-4), in which $R^{3B}$ and $R^{4B}$ may be the same or different, and represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, or an aralkyl group (the aryl moiety has 6 to 10 carbon atoms, and the alkylene moiety has 1 to 8 carbon atoms).

(B-1-6)

The compound according to any one of (B-1) and (B-1-1) to (B-1-5), in which $R^{5B}$ represents a hydrogen atom, an alkyl group having 1 to 8 carbon atoms, or an aralkyl group (the aryl moiety has 6 to 10 carbon atoms, and the alkylene moiety has 1 to 8 carbon atoms).

(B-1-7)

The compound according to any one of (B-1) and (B-1-1) to (B-1-6), in which $R^{5B}$ represents a hydrogen atom.

(B-1-8)

The compound according to any one of (B-1) and (B-1-1) to (B-1-7), in which $R^{6B}$ and $R^{7B}$ may be the same or different, and represent a hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms, or a pharmaceutically acceptable salt thereof.

(B-1-9)

The compound according to any one of (B-1) and (B-1-1) to (B-1-8), in which $R^{6B}$ and $R^{7B}$ both represent hydrogen atoms.

(B-1-10)

The compound according to any one of (B-1) and (B-1-1) to (B-1-9), in which $R^{3B}$, $R^{4B}$, $R^{5B}$, $R^{6B}$, and $R^{7B}$ are hydrogen atoms.

(B-1-11)

The compound according to any one of (B-1) and (B-1-1) to (B-1-10), in which $X^B$ represents N, $Y^B$ represents C(═O), and the double line consisting of the solid line and the broken line represents a single bond.

(B-1-12)

The compound according to any one of (B-1) and (B-1-1) to (B-1-11), in which $X^B$ represents C, $Y^B$ represents N, and the double line consisting of the solid line and the broken line represents a double bond.

(B-1-13)

The compound according to any one of (B-1) and (B-1-1) to (B-1-12), in which $Z^B$ represents an oxygen atom.

(B-1-14)

The compound according to any one of (B-1) and (B-1-1) to (B-1-13), in which $A^B$ represents a phenyl group or a pyridyl group that may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an aralkyl group (the aryl moiety has 6 to 10 carbon atoms, and the alkylene moiety has 1 to 8 carbon atoms), a phenyl group, and a pyridyl group as a substituent.

(B-1-15)

The compound according to any one of (B-1) and (B-1-1) to (B-1-14), in which $A^B$ represents a phenyl group that may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, and an amino group as a substituent.

(B-1-16)

The compound according to any one of (B-1) and (B-1-1) to (B-1-15), in which $A^B$ represents a phenyl group or a pyridyl group.

(B-1-17)

The compound according to any one of (B-1) and (B-1-1) to (B-1-16), in which $A^B$ represents an atomic bond.

(B-1-18)

The compound according to any one of (B-1) and (B-1-1) to (B-1-17), in which $B^B$ represents NHC(=O), NHCONH, CONH, NHC(=S)NH, $NHSO_2$, $SO_2NH$, or $OSO_2$.

(B-1-19)

The compound according to any one of (B-1) and (B-1-1) to (B-1-18), in which $B^B$ represents NHC(=O), NHCONH, or $NHSO_2$.

(B-1-20)

The compound according to any one of (B-1) and (B-1-1) to (B-1-19), in which $B^B$ represents NHC(=O) or $NHSO_2$.

(B-1-21)

The compound according to any one of (B-1) and (B-1-1) to (B-1-20), in which $B^B$ represents NHC(=O).

(B-1-22)

The compound according to any one of (B-1) and (B-1-1) to (B-1-21), in which $D^B$ represents an alkylene chain having 1 to 6 carbon atoms that may have 1 to 4 of the same or different substituents selected from an alkyl group having 1 to 8 carbon atoms and an alkyl group having 1 to 8 carbon atoms and substituted with 1 to 3 halogen atoms as a substituent, and may further have a double bond.

(B-1-23)

The compound according to any one of (B-1) and (B-1-1) to (B-1-22), in which $D^B$ represents an atomic bond.

(B-1-24)

The compound according to any one of (B-1) and (B-1-1) to (B-1-23), in which $D^B$ has 1 to 4 of the same or different substituents selected from an alkyl group having 1 to 8 carbon atoms and an alkenyl group having 2 to 8 carbon atoms as a substituent.

(B-1-25)

The compound according to any one of (B-1) and (B-1-1) to (B-1-24), in which $D^B$ has 1 to 4 of the same or different substituents selected from an alkyl group having 1 to 3 carbon atoms and an alkenyl group having 2 or 3 carbon atoms as a substituent.

(B-1-26)

The compound according to any one of (B-1) and (B-1-1) to (B-1-25), in which $E^B$ represents an atomic bond.

(B-1-27)

The compound according to any one of (B-1) and (B-1-1) to (B-1-26), in which $G^B$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine that may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, and an alkylsulfonyl group having 1 to 6 carbon atoms as a substituent.

(B-1-28)

The compound according to any one of (B-1) and (B-1-1) to (B-1-27), in which $G^B$ represents benzene that may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, and an alkylsulfonyl group having 1 to 6 carbon atoms as a substituent.

(B-1-29)

The compound according to any one of (B-1) and (B-1-1) to (B-1-28), in which $G^B$ represents benzene or pyridine that may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, a halogen atom, a hydroxyl group, a nitro group, an amino group, a dialkylamino group having 2 to 8 carbon atoms, a carboxyl group, an alkylsulfinyl group having 1 to 6 carbon atoms, an alkylthio group having 1 to 6 carbon atoms, and an alkylsulfonyl group having 1 to 6 carbon atoms as a substituent.

(B-1-30)

The compound according to any one of (B-1) and (B-1-1) to (B-1-29), in which $G^B$ represents benzene that may have 1 to 4 of the same or different substituents selected from an alkyl group having 1 to 8 carbon atoms and substituted with 1 to 3 halogen atoms, a halogen atom, and a hydroxyl group as a substituent.

(B-1-31)

The compound according to any one of (B-1) and (B-1-1) to (B-1-30), in which $m^B$ represents 0.

(B-1-32)

The compound according to any one of (B-1) and (B-1-1) to (B-1-31), in which $A^B$ represents a benzene ring, $m^B$ represents 0, $B^B$ represents NHC(═O) or $NHSO_2$, $D^B$ represents an alkyl group having 1 to 3 carbon atoms or an atomic bond, $E^B$ represents an atomic bond, and $G^B$ represents benzene that may have 1 to 4 of the same or different substituents selected from an alkyl group having 1 to 8 carbon atoms, an alkyl group having 1 to 8 carbon atoms and substituted with 1 to 3 halogen atoms, a halogen atom, and a hydroxyl group as a substituent.

(B-1-33)

The compound according to any one of (B-1) and (B-1-1) to (B-1-32), in which $A^B$ represents a benzene ring, $m^B$ represents 0, $B^B$ represents NHC(═O), $D^B$ represents an atomic bond, $E^B$ represents an atomic bond, and $G^B$ represents benzene that may have 1 to 4 of the same or different substituents selected from an alkyl group having 1 to 8 carbon atoms and substituted with 1 to 3 halogen atoms, a halogen atom, and a hydroxyl group as a substituent.

(B-1-34)

The compound according to any one of (B-1) and (B-1-1) to (B-1-33), in which $R^{1B}$ and $R^{2B}$ bind together to form a naphthalene ring together with the benzene ring to which they bind, $R^{3B}$, $R^{4B}$, $R^{5B}$, $R^{6B}$, and $R^{7B}$ represent hydrogen atoms, $X^B$ represents N, $Y^B$ represents C(═O), the double line consisting of the solid line and the broken line represents a single bond, $Z^B$ represents an oxygen atom, $A^B$ represents a benzene ring, $m^B$ represents 0, $B^B$ represents NHC(═O) or $NHSO_2$, $D^B$ represents an alkyl group having 1 to 3 carbon atoms or an atomic bond, $E^B$ represents an atomic bond, and $G^B$ represents benzene that may have 1 to 4 of the same or different substituents selected from an alkyl group having 1 to 8 carbon atoms, an alkyl group having 1 to 8 carbon atoms and substituted with 1 to 3 halogen atoms, a halogen atom, and a hydroxyl group as a substituent.

(B-1-35)

The compound according to any one of (B-1) and (B-1-1) to (B-1-34), in which, in the general formula (BI), $R^{1B}$ and $R^{2B}$ bind together to form a naphthalene ring together with the benzene ring to which they bind, $R^{3B}$, $R^{4B}$, $R^{5B}$, $R^{6B}$, and $R^{7B}$ represent hydrogen atoms, $X^B$ represents N, $Y^B$ represents C(═O), the double line consisting of the solid line and the broken line represents a single bond, $Z^B$ represents an oxygen atom, $A^B$ represents a benzene ring, $m^B$ represents 0, $B^B$ represents NHC(═O), $D^B$ represents an atomic bond, $E^B$ represents an atomic bond, and $G^B$ represents benzene that may have 1 to 4 of the same or different substituents selected from an alkyl group having 1 to 8 carbon atoms and substituted with 1 to 3 halogen atoms, a halogen atom, and a hydroxyl group as a substituent.

As the compound represented the general formula (BII), the following compounds are preferable.

(B-2-1)

[Formula 9]

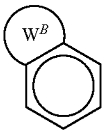

The compound according to (B-2) in which the above moiety represents a naphthalene ring or a tetrahydronaphthalene ring that may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (the alkoxy moiety has 1 to 8 carbon atoms), and an aralkyl group (the aryl moiety has 6 to 10 carbon atoms, and the alkylene moiety has 1 to 8 carbon atoms) as a substituent.

(B-2-2)

[Formula 10]

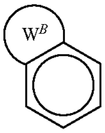

The compound according to (B-2) or (B-2-1) in which the above moiety represents a naphthalene ring that may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, and an amino group as a substituent.

(B-2-3)

The compound according to any one of (B-2), (B-2-1), and (B-2-2) in which $R^{3Ba}$ and $R^{4Ba}$ may be the same or different, and represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, or an aralkyl group (the aryl moiety has 6 to 10 carbon atoms, and the alkylene moiety has 1 to 8 carbon atoms).

(B-2-4)

The compound according to any one of (B-2) and (B-2-1) to (B-2-3), in which $R^{5Ba}$ represents a hydrogen atom, an alkyl group having 1 to 8 carbon atoms, or an aralkyl group (the aryl moiety has 6 to 10 carbon atoms, and the alkylene moiety has 1 to 8 carbon atoms).

(B-2-5)

The compound according to any one of (B-2) and (B-2-1) to (B-2-4), in which $R^{5Ba}$ represents a hydrogen atom.

(B-2-6)

The compound according to any one of (B-2) and (B-2-1) to (B-2-5), in which $R^{6Ba}$ and $R^{7Ba}$ may be the same or different, and represent a hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms.

(B-2-7)

The compound according to any one of (B-2) and (B-2-1) to (B-2-6), in which $R^{6Ba}$ and $R^{7Ba}$ both represent hydrogen atoms.

(B-2-8)

[Formula 11]

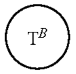

The compound according to any one of (B-2) and (B-2-1) to (B-2-7), in which the above moiety represents a phenyl group or a pyridyl group that may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an aralkyl group (the aryl moiety has 6 to 10 carbon atoms, and the alkylene moiety has 1 to 8 carbon atoms), a phenyl group, and a pyridyl group as a substituent.

(B-2-9)

[Formula 12]

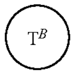

The compound according to any one of (B-2) and (B-2-1) to (B-2-8), in which the above moiety represents a phenyl group that may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, and an amino group as a substituent.

(B-2-10)

[Formula 13]

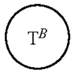

The compound according to any one of (B-2) and (B-2-1) to (B-2-9), in which the above moiety represents an atomic bond.

(B-2-11)

The compound according to any one of (B-2) and (B-2-1) to (B-2-10), in which $B^{Ba}$ represents NHC(=O), NHCONH, CONH, NHC(=S)NH, $NHSO_2$, $SO_2NH$, or $OSO_2$.

(B-2-12)

The compound according to any one of (B-2) and (B-2-1) to (B-2-11), in which $B^{Ba}$ represents NHC(=O), NHCONH, or $NHSO_2$.

(B-2-13)

The compound according to any one of (B-2) and (B-2-1) to (B-2-12), in which $E^{Ba}$ represents an atomic bond.

(B-2-14)

The compound according to any one of (B-2) and (B-2-1) to (B-2-13), in which $G^{Ba}$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine that may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, and an alkylsulfonyl group having 1 to 6 carbon atoms as a substituent.

(B-2-15)

The compound according to any one of (B-2) and (B-2-1) to (B-2-14), in which $G^{Ba}$ represents benzene that may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, and an alkylsulfonyl group having 1 to 6 carbon atoms as a substituent.

(B-2-16)

The compound according to any one of (B-2) and (B-2-1) to (B-2-15), in which $n^B$ represents 0.

In the general formula (BI), it is preferable that $R^{B1}$ and $R^{B2}$ bind together to form a condensed ring selected from a naphthalene ring or a tetrahydronaphthalene ring together with the benzene ring to which they bind, and it is particularly preferable that $R^{B1}$ and $R^{B2}$ bind together to form a naphthalene ring together with the benzene ring to which they bind.

In the general formula (BI), it is preferable that $R^{B3}$, $R^{B4}$, $R^{B5}$, $R^{B6}$, and $R^{B7}$ represent hydrogen atoms.

In the general formula (BI), it is preferable that $X^B$ represents N, $Y^B$ represents C(=O), and the double line consisting of the solid line and the broken line represents a single bond.

In the general formula (BI), it is preferable that $Z^B$ represents an oxygen atom.

In the general formula (BI), it is preferable that $A^B$ represents a benzene ring or a pyridine ring, and it is particularly preferable that $A^B$ represents a benzene ring.

In the general formula (BI), it is preferable that $m^B$ represents 0 to 4, and it is particularly preferable that $m^B$ represents 0.

In the general formula (BI), it is preferable that $B^B$ represents $N(R^{8B})C(=O)$ or $N(R^{10B})SO_2$, and in this case, it is more preferable that $R^{8B}$ and $R^{10B}$ represent hydrogen atoms. Furthermore, in the general formula (BI), it is particularly preferable that $B^B$ represents NHC(=O).

In the general formula (BI), it is preferable that $D^B$ represents an alkylene chain having 1 to 6 carbon atoms which has 1 to 4 of the same or different substituents selected from an alkyl group having 1 to 8 carbon atoms and an alkenyl group having 2 to 8 carbon atoms as a substituent, or represents an atomic bond, it is more preferable that $D^B$ represents an alkylene chain having 1 to 8 carbon atoms which has 1 to 4 of the same or different substituents selected from an alkyl group having 1 to 3 carbon atoms and an alkenyl group having 2 or 3 carbon atoms as a substituent, or represents an atomic bond, and it is particularly preferable that $D^B$ represents an atomic bond.

In the general formula (BI), it is preferable that $E^B$ represents O or an atomic bond, and it is particularly preferable that $E^B$ represents an atomic bond.

In the general formula (BI), it is preferable that $G^B$ represents benzene or pyridine which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, a halogen atom, a hydroxyl group, a nitro group, an amino group, a dialkylamino group having 2 to 8 carbon atoms, a carboxyl group, an alkylsulfinyl group having 1 to 6 carbon atoms, an alkylthio group having 1 to 6 carbon atoms, and an alkylsulfonyl group having 1 to 6 carbon atoms as a substituent, and it is particularly preferable that $G^B$ represents benzene which may have 1 to 4 of the same or different substituents selected from an alkyl group having 1 to 8 carbon atoms and substituted with 1 to 3 halogen atoms, a halogen atom, and a hydroxyl group as a substituent.

In the general formula (BI), it is particularly preferable that $A^B$ represents a benzene ring, $m^B$ represents O, $B^B$ represents NHC(=O) or $NHSO_2$, $D^B$ represents an alkyl group having 1 to 3 carbon atoms or an atomic bond, $E^B$ represents an atomic bond, and $G^B$ represents benzene which may have 1 to 4 of the same or different substituents selected from an alkyl group having 1 to 8 carbon atoms, an alkyl group having 1 to 8 carbon atoms and substituted with 1 to 3 halogen atoms, a halogen atom, and a hydroxyl group as a substituent.

In the general formula (BI), it is particularly preferable that $A^B$ represents a benzene ring, $m^B$ represents O, $B^B$ represents NHC(=O), $D^B$ represents an atomic bond, $E^B$ represents an atomic bond, and $G^B$ represents benzene which may have 1 to 4 of the same or different substituents selected from an alkyl group having 1 to 8 carbon atoms and substituted with 1 to 3 halogen atoms, a halogen atom, and a hydroxyl group as a substituent.

In the general formula (BI), it is more preferable that $R^{B1}$ and $R^{B2}$ bind together to form a naphthalene ring together with the benzene ring to which they bind, $R^{B3}$, $R^{B4}$, $R^{B5}$, $R^{B6}$, and $R^{B7}$ represent hydrogen atoms, $X^B$ represents N, $Y^B$ represents C(=O), the double line consisting of the solid line and the broken line represents a single bond, $Z^B$ represents an oxygen atom, $A^B$ represents a benzene ring, $m^B$ represents 0, $B^B$ represents NHC(=O) or $NHSO_2$, $D^B$ represents an alkyl group having 1 to 3 carbon atoms or an atomic bond, $E^B$ represents an atomic bond, and $G^B$ represents benzene which may have 1 to 4 of the same or different substituents selected from an alkyl group having 1 to 8 carbon atoms, an alkyl group having 1 to 8 carbon atoms and substituted with 1 to 3 halogen atoms, a halogen atom, and a hydroxyl group as a substituent.

In the general formula (BI), it is particularly preferable that $R^{B1}$ and $R^{B2}$ bind together to form a naphthalene ring together with the benzene ring to which they bind, $R^{B3}$, $R^{B4}$, $R^{B5}$, $R^{B6}$, and $R^{B7}$ represent hydrogen atoms, $X^B$ represents N, $Y^B$ represents C(=O), the double line consisting of the solid line and the broken line represents a single bond, $Z^B$ represents an oxygen atom, $A^B$ represents a benzene ring, $m^B$ represents O, $B^B$ represents NHC(=O), $D^B$ represents an atomic bond, $E^B$ represents an atomic bond, and $G^B$ represents benzene which may have 1 to 4 of the same or different substituents selected from an alkyl group having 1 to 8 carbon atoms and substituted with 1 to 3 halogen atoms, a halogen atom, and a hydroxyl group as a substituent.

Typical compounds comprised in the compounds represented by the general formulas (BI) and/or (BII) are as follows.

Typical Compound Example B-100

[Formula 14]

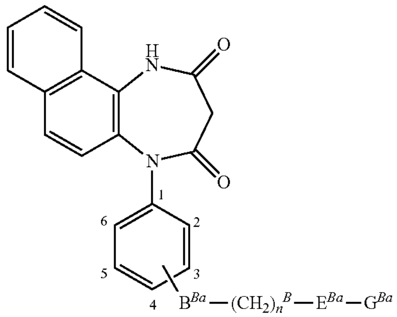

($B^{Ba}$ (substitution position), $n^B$, $E^{Ba}$, and $G^{Ba}$ in the formula are indicated in Tables 8 to 17)

TABLE 8

| $B^{Ba}$ (substitution position) | $n^B$ | $E^{Ba}$ | $G^{Ba}$ |
|---|---|---|---|
| NHCO(4) | 0 | Atomic bond | Phenyl |
| NHCO(4) | 0 | Atomic bond | (2-$CF_3$)Phenyl |
| NHCO(4) | 0 | Atomic bond | (3-Br)Phenyl |
| NHCO(4) | 0 | Atomic bond | (4-$CF_3$)Phenyl |
| NHCO(4) | 0 | Atomic bond | (2-Me)Phenyl |
| NHCO(4) | 0 | Atomic bond | (2,6-Me)Phenyl |
| NHCO(4) | 0 | Atomic bond | (2,6-Cl)Phenyl |
| NHCO(4) | 0 | Atomic bond | (3-Cl)Phenyl |
| NHCO(4) | 1 | Atomic bond | Phenyl |
| NHC(=S)NH(4) | 0 | Atomic bond | Phenyl |
| NHCO(4) | 0 | Atomic bond | (2,3-OMe)Phenyl |
| NHCO(4) | 0 | Atomic bond | (2-OMe)Phenyl |
| NHCO(4) | 1 | Atomic bond | (2-Cl)Phenyl |
| NHCO(4) | 0 | Atomic bond | (2,3-Me)Phenyl |
| NHCO(4) | 0 | Atomic bond | (2,5-Me)Phenyl |
| NHCO(4) | 0 | Atomic bond | (2-Cl,5-Br)Phenyl |

TABLE 9

| $B^{Ba}$ (substitution position) | $n^B$ | $E^{Ba}$ | $G^{Ba}$ |
|---|---|---|---|
| NHCO(4) | 0 | Atomic bond | (2,4-Cl)Phenyl |
| NHCO(4) | 0 | Atomic bond | (2-OH)Phenyl |
| NHCO(4) | 0 | Atomic bond | (2,3-OH)Phenyl |
| NHC(=O)NH(4) | 0 | Atomic bond | Phenyl |
| NHCO(4) | 1 | Atomic bond | (2,6-Cl)Phenyl |
| NHCO(4) | 1 | Atomic bond | (2-OMe)Phenyl |
| NHCO(4) | 1 | Atomic bond | (2-OH)Phenyl |
| NHC(=S)NH(4) | 0 | Atomic bond | (2-Cl)Phenyl |
| NHCO(4) | 0 | Atomic bond | ($3-CF_3$)Phenyl |
| NHCO(4) | 1 | Atomic bond | ($2-CF_3$)Phenyl |
| NHC(=O)NH(4) | 0 | Atomic bond | (2-Cl)Phenyl |
| NHCO(4) | 0 | Atomic bond | (2-Cl,3-OMe)Phenyl |
| NHCO(4) | 2 | Atomic bond | Phenyl |
| NHCO(4) | 0 | Atomic bond | 3-indolyl |
| NHCO(4) | 0 | Atomic bond | (2-Cl,3-OH)Phenyl |
| NHCO(4) | 1 | O | Phenyl |

TABLE 10

| $B^{Ba}$ (substitution position) | $n^B$ | $E^{Ba}$ | $G^{Ba}$ |
|---|---|---|---|
| NHCO(4) | 1 | Atomic bond | (2-Cl,4-OMe)Phenyl |
| NHCO(4) | 0 | Atomic bond | (1-Me)imidazol 2-yl |
| NHCO(4) | 1 | Atomic bond | (2,4-Cl)Phenyl |
| NHCO(4) | 1 | Atomic bond | (2-Cl,4-OH)Phenyl |
| NHCO(4) | 1 | Atomic bond | pyridin 3-yl |
| NHCO(4) | 0 | Atomic bond | Benzimidazol 2-yl |
| NHCO(4) | 0 | Atomic bond | (2-Cl)Phenyl |
| NHCO(4) | 0 | Atomic bond | (2-Br)Phenyl |
| NHCO(4) | 0 | Atomic bond | (2-I)Phenyl |
| NHCO(4) | 1 | Atomic bond | (2-Me)Phenyl |
| NHCO(4) | 0 | Atomic bond | quinoxalin 2-yl |
| NHCO(4) | 0 | Atomic bond | (5-Me) thiophen 2-yl |
| NHCO(3) | 1 | Atomic bond | (2-Cl)Phenyl |
| NHCO(4) | 0 | Atomic bond | (2,4,6-Me)Phenyl |
| NHCO(4) | 0 | Atomic bond | (2-Et)Phenyl |
| NHC(=S)NH(4) | 0 | Atomic bond | (2-Me)Phenyl |

TABLE 11

| $B^{Ba}$ (substitution position) | $n^B$ | $E^{Ba}$ | $G^{Ba}$ |
|---|---|---|---|
| NHCO(4) | 0 | Atomic bond | ($4-NMe_2$)Phenyl |
| NHCO(4) | 1 | O | (2,4-Cl)Phenyl |
| NHCO(4) | 1 | O | (2-Me)Phenyl |
| NHCO(4) | 0 | Atomic bond | (2-Ac)Phenyl |
| NHCO(4) | 0 | Atomic bond | (2-tBu)Phenyl |
| NHCO(3) | 0 | Atomic bond | (2-I)Phenyl |
| NHCO(4) | 0 | Atomic bond | (1-Me) piperidin 4-yl |
| NHCO(4) | 0 | Atomic bond | benzofuran 2-yl |
| NHCO(4) | 0 | Atomic bond | (1-Me) indol 3-yl |
| NHCO(4) | 0 | Atomic bond | (2-allyl)Phenyl |
| NHCO(4) | 0 | Atomic bond | (2-nPr)Phenyl |
| NHCO(4) | 0 | Atomic bond | (2-iPrO)Phenyl |
| NHCO(4) | 0 | Atomic bond | 3-Me thiophen 2-yl |
| NHCO(4) | 1 | O | (2-Me,3-Cl)Phenyl |
| NHCO(4) | 0 | Atomic bond | ($2-CF_3$,4-F)Phenyl |
| NHCO(4) | 0 | Atomic bond | (2-OMe,4-F)Phenyl |

TABLE 12

| $B^{Ba}$ (substitution position) | $n^B$ | $E^{Ba}$ | $G^{Ba}$ |
|---|---|---|---|
| NHCO(4) | 0 | Atomic bond | (2-OH,4-F)Phenyl |
| NHCO(3) | 1 | Atomic bond | (2-I)Phenyl |
| NHCO(4) | 0 | Atomic bond | ($3-NMe_2$)Phenyl |
| NHCO(4) | 0 | Atomic bond | (2-OMe,4-I)Phenyl |

TABLE 12-continued

| $B^{Ba}$ (substitution position) | $n^B$ | $E^{Ba}$ | $G^{Ba}$ |
|---|---|---|---|
| NHCO(4) | 0 | Atomic bond | (2-OMe,6-F)Phenyl |
| NHCO(4) | 0 | Atomic bond | (2-OH,4-I)Phenyl |
| NHCO(4) | 0 | Atomic bond | (2-OH,6-F)Phenyl |
| NHCO(4) | 0 | Atomic bond | (2-F)Phenyl |
| NHCO(4) | 0 | Atomic bond | ($2-NMe_2$)Phenyl |
| NHCO(4) | 0 | Atomic bond | (2-OMe,6-Me)Phenyl |
| NHCO(4) | 0 | Atomic bond | (2-OH,6-Me)Phenyl |
| NHCO(4) | 2 | Atomic bond | (2-Me)Phenyl |
| CONH(4) | 0 | Atomic bond | Phenyl |
| CONH(4) | 1 | Atomic bond | Phenyl |
| NHCO(4) | 2 | Atomic bond | (2-Cl)Phenyl |
| CONH(4) | 1 | Atomic bond | (2-Cl)Phenyl |

TABLE 13

| $B^{Ba}$ (substitution position) | $n^B$ | $E^{Ba}$ | $G^{Ba}$ |
|---|---|---|---|
| CONH(4) | 0 | Atomic bond | (2-Cl)Phenyl |
| NHCO(4) | 0 | Atomic bond | (5-Br,2,3-methylenedioxy)Phenyl |
| NHCO(4) | 0 | Atomic bond | (2-OMe,6-Br)Phenyl |
| NHCO(4) | 0 | Atomic bond | (2-OH,6-Br)Phenyl |
| NHCO(4) | 0 | Atomic bond | (2-OMe,6-Cl)Phenyl |
| NHCO(4) | 0 | Atomic bond | (2-OH,6-Cl)Phenyl |
| NHCO(4) | 0 | Atomic bond | (2-OH,6-OMe)Phenyl |
| NHCO(4) | 0 | Atomic bond | (2-OMe,$6-CF_3$)Phenyl |
| NHCO(4) | 0 | Atomic bond | (2-OH,$6-CF_3$)Phenyl |
| NHCO(4) | 0 | Atomic bond | (2-Cl,5-SMe)Phenyl |
| NHCO(4) | 0 | Atomic bond | (2-SMe)Phenyl |
| NHCO(4) | 0 | Atomic bond | (3-SMe)Phenyl |
| NHCO(4) | 0 | Atomic bond | (2-OMe,6-Et)Phenyl |
| NHCO(4) | 0 | Atomic bond | ($3-SO_2Me$)Phenyl |
| NHCO(4) | 0 | Atomic bond | (2-OH,6-Et)Phenyl |
| NHCO(4) | 0 | Atomic bond | (3-S(=O)Me)Phenyl |

TABLE 14

| $B^{Ba}$ (substitution position) | $n^B$ | $E^{Ba}$ | $G^{Ba}$ |
|---|---|---|---|
| NHCO(4) | 0 | Atomic bond | (2-Cl,5-S(=O)Me)Phenyl |
| NHCO(4) | 0 | Atomic bond | (2-S(=O)Me)Phenyl |
| NHCO(4) | 0 | Atomic bond | (3-Cl) pyridin 2-yl |
| NHCO(4) | 0 | Atomic bond | (2-OMe,3-Cl)Phenyl |
| NHCO(4) | 0 | Atomic bond | (3-Me) pyridin 2-yl |
| NHCO(4) | 0 | Atomic bond | (2-OH,3-Cl)Phenyl |
| NHCO(4) | 0 | Atomic bond | (3-OH) pyridin 2-yl |
| NHCO(4) | 0 | Atomic bond | (3-Vinyl) pyridin 2-yl |
| NHCO(4) | 0 | Atomic bond | (2-Et) pyridin 2-yl |
| $NHSO_2(4)$ | 0 | Atomic bond | ($2-NO_2$)Phenyl |
| $NHSO_2(4)$ | 0 | Atomic bond | Phenyl |
| $NHSO_2(4)$ | 0 | Atomic bond | (3-Br)Phenyl |
| $NHSO_2(4)$ | 0 | Atomic bond | (3-OMe)Phenyl |
| $NHSO_2(3)$ | 0 | Atomic bond | ($2-NO_2$)Phenyl |
| $NMeSO_2(3)$ | 0 | Atomic bond | ($2-NO_2$)Phenyl |
| $NHSO_2(3)$ | 0 | Atomic bond | naphthalen 2-yl |

TABLE 15

| $B^{Ba}$(substitution position) | $n^B$ | $E^{Ba}$ | $G^{Ba}$ |
|---|---|---|---|
| $NHSO_2(3)$ | 0 | Atomic bond | naphthalen 1-yl |
| $NHSO_2(4)$ | 0 | Atomic bond | Cyclohexyl |
| $NHSO_2(4)$ | 0 | Atomic bond | pyridin 3-yl |
| $NHSO_2(4)$ | 0 | Atomic bond | (4-iPr)Phenyl |
| $NHSO_2(4)$ | 1 | Atomic bond | Phenyl |
| $NHSO_2(4)$ | 0 | Atomic bond | thiophen 2-yl |
| $NHSO_2(4)$ | 0 | Atomic bond | naphthalen 2-yl |
| $NBnSO_2(4)$ | 0 | Atomic bond | ($2-NO_2$)Phenyl |

TABLE 15-continued

| $B^{Ba}$(substitution position) | $n^B$ | $E^{Ba}$ | $G^{Ba}$ |
|---|---|---|---|
| $NMeSO_2(4)$ | 0 | Atomic bond | (3-Br)Phenyl |
| $NMeSO_2(4)$ | 0 | Atomic bond | (2-$NO_2$)Phenyl |
| $N(CH_2CH_2OH)SO_2(4)$ | 0 | Atomic bond | (2-$NO_2$)Phenyl |
| $NHSO_2(4)$ | 1 | Atomic bond | (2-Cl)Phenyl |
| $NHSO_2(4)$ | 1 | Atomic bond | (3-Br)Phenyl |
| $NHSO_2(4)$ | 0 | Atomic bond | (2-$CF_3$)Phenyl |
| $NHSO_2(4)$ | 1 | Atomic bond | (2-Br)Phenyl |
| $NHSO_2(4)$ | 1 | Atomic bond | (2-Me)Phenyl |

TABLE 16

| $B^{Ba}$(substitution position) | $n^B$ | $E^{Ba}$ | $G^{Ba}$ |
|---|---|---|---|
| $NHSO_2(4)$ | 1 | Atomic bond | (2-$NO_2$)Phenyl |
| $NHSO_2(4)$ | 2 | Atomic bond | Phenyl |
| $NHSO_2(4)$ | 1 | Atomic bond | (4-Cl)Phenyl |
| $NMeSO_2(4)$ | 1 | Atomic bond | (2-$CF_3$)Phenyl |
| $NMeSO_2(4)$ | 1 | Atomic bond | (2-Et)Phenyl |
| $NMeSO_2(4)$ | 1 | Atomic bond | (2,3-Me)Phenyl |
| $NMeSO_2(4)$ | 2 | Atomic bond | (2-Cl)Phenyl |
| $NMeSO_2(4)$ | 1 | Atomic bond | (2-$NO_2$)Phenyl |
| $NMeSO_2(4)$ | 1 | Atomic bond | (2-$NH_2$)Phenyl |
| $NMeSO_2(4)$ | 1 | Atomic bond | (2-$NMe_2$)Phenyl |

TABLE 17

| $B^{Ba}$(substitution position) | $n^B$ | $E^{Ba}$ | $G^{Ba}$ |
|---|---|---|---|
| NHCO(4) | 0 | Atomicbond | Pyridin 4-yl |
| NHCO(4) | 1 | O | Pyridin 3-yl |
| NHCO(4) | 0 | Atomic bond | Pyridin 3-yl |
| NHCO(4) | 0 | Atomic bond | (2-Me)Pyridin 3-yl |
| NHCO(4) | 0 | Atomic bond | (2-Cl)Pyridin 3-yl |
| NHCO(4) | 1 | O | Pyridin 2-yl |
| NHCO(4) | 0 | Atomic bond | (4-$CF_3$)Pyridin 3-yl |
| NHCO(4) | 0 | Atomic bond | (2-iPr)Phenyl |

Typical Compound Example B-200

[Formula 15]

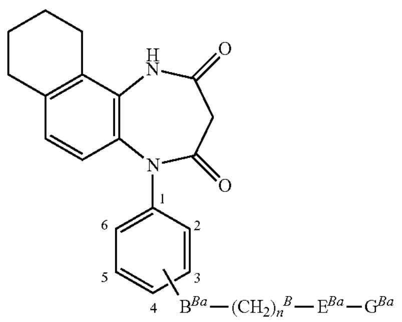

($B^{Ba}$ (substitution position), $n^B$, $E^{Ba}$, and $G^{Ba}$ in the formula are indicated in Tables 18 and 19)

TABLE 18

| $B^{Ba}$(substitution position) | $n^B$ | $E^{Ba}$ | $G^{Ba}$ |
|---|---|---|---|
| NHCO(4) | 0 | Atomic bond | Cyclohexyl |
| NHCO(4) | 0 | Atomic bond | (6-Me) pyridin-2-yl |
| NHCO(4) | 0 | Atomic bond | (2-Me) pyridin-3-yl |
| NHCO(4) | 0 | Atomic bond | (2-OMe,3-Me)Phenyl |
| NHCO(4) | 0 | Atomic bond | (2,3-Cl)Phenyl |
| NHCO(4) | 0 | Atomic bond | (2-OH,3-Me)Phenyl |
| NHCO(4) | 0 | Atomic bond | (2-I)Phenyl |
| NHCO(4) | 1 | Atomic bond | (1-Me) pyrrol 2-yl |
| NHCO(4) | 1 | Atomic bond | (2-tBu)Phenyl |
| NHCO(4) | 0 | Atomic bond | (2-Isopropenyl) phenyl |
| NHCO(4) | 0 | Atomic bond | (2-iPr)Phenyl |
| NHCO(4) | 1 | Atomic bond | morpholin 2-yl |
| NHCO(4) | 0 | Atomic bond | (2-Cl) pyridin 2-yl |

TABLE 19

| $B^{Ba}$(substitution position) | $n^B$ | $E^{Ba}$ | $G^{Ba}$ |
|---|---|---|---|
| $NHSO_2(4)$ | 0 | Atomic bond | (2-$NO_2$)Phenyl |
| $NMeSO_2(4)$ | 0 | Atomic bond | (2-$NO_2$)Phenyl |
| $SO_2NH(4)$ | 0 | Atomic bond | Phenyl |
| $OSO_2(4)$ | 0 | Atomic bond | (3-Br)Phenyl |
| $NHSO_2(4)$ | 1 | Atomic bond | (2-Cl)Phenyl |
| $NHSO_2(4)$ | 0 | Atomic bond | (3-Br)Phenyl |
| $NHSO_2(4)$ | 0 | Atomic bond | (3-OMe)Phenyl |
| $NHSO_2(4)$ | 1 | Atomic bond | (2,3-Cl)Phenyl |
| $NHSO_2(4)$ | 1 | Atomic bond | (2,6-Cl)Phenyl |
| $NHSO_2(4)$ | 1 | Atomic bond | (2-I)Phenyl |
| $NMeSO_2(4)$ | 1 | Atomic bond | (2-Cl)Phenyl |

Typical Compound Example B-300

[Formula 16]

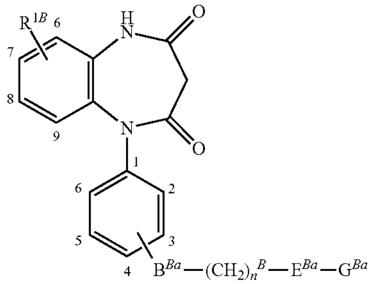

($R^{1B}$, $B^{Ba}$ (substitution position), $n^B$, $E^{Ba}$, and $G^{Ba}$ in the formula are indicated in Table 20)

TABLE 20

| $R^{1B}$ | $B^{Ba}$(substitution position) | $n^B$ | $E^{Ba}$ | $G^{Ba}$ |
|---|---|---|---|---|
| 7-OMe | NHCO(4) | 0 | Atomic bond | (2,3-Me)Phenyl |
| 7-OH | NHCO(4) | 0 | Atomic bond | (2,3-Me)Phenyl |
| 6-Me | NHCO(4) | 0 | Atomic bond | (2,3-Me)Phenyl |
| 6,7-Me | NHCO(4) | 0 | Atomic bond | (2-I)Phenyl |
| 6-Et | NHCO(4) | 0 | Atomic bond | (2-I)Phenyl |

TABLE 20-continued

| $R^{1B}$ | $B^{Ba}$(substitution position) | $n^B$ | $E^{Ba}$ | $G^{Ba}$ |
|---|---|---|---|---|
| 7-Ph | NHCO(4) | 0 | Atomic bond | (2-Isopropyl))Phenyl |
| 7-(Pyridin-3yl) | NHCO(4) | 0 | Atomic bond | (2-Isopropyl))Phenyl |
| 7-(Pyridin-2yl) | NHCO(4) | 0 | Atomic bond | (2-Isopropyl)Phenyl |
| 7-Cl | $NHSO_2(4)$ | 0 | Atomic bond | (2-Isopropyl)Phenyl |
| 7-Br | $NHSO_2(4)$ | 0 | Atomic bond | (2-Isopropyl)Phenyl |
| $7\text{-}CF_3$ | $NHSO_2(4)$ | 0 | Atomic bond | (2-Isopropyl)Phenyl |
| H | $NHSO_2(4)$ | 0 | Atomic bond | (2-Isopropyl)Phenyl |
| 6-Me,7-Br | $NHSO_2(4)$ | 0 | Atomic bond | (2-Isopropyl)Phenyl |
| 7-OMe | $NHSO_2(4)$ | 1 | Atomic bond | (2-Cl)Phenyl |
| 7-OH | $NHSO_2(4)$ | 1 | Atomic bond | (2-Cl)Phenyl |
| 6-Me | $NHSO_2(4)$ | 1 | Atomic bond | (2-Cl)Phenyl |

Typical Compound Example B-400

[Formula 17]

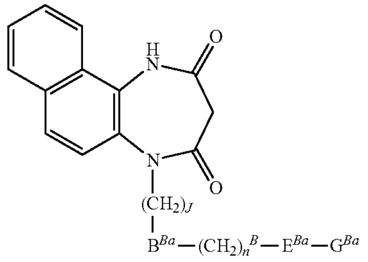

($B^{Ba}$ (substitution position), $n^B$, $E^{Ba}$, and $G^{Ba}$ in the formula are indicated in Table 21)

TABLE 21

| $B^{Ba}$(substitution position) | $n^B$ | $E^{Ba}$ | $G^{Ba}$ |
|---|---|---|---|
| NHCO | 0 | Atomic bond | (2-Cl,3-OMe)Phenyl |
| NHCO | 0 | Atomic bond | (2-I)Phenyl |
| $NHSO_2$ | 1 | Atomic bond | (2-Cl)Phenyl |
| $NHSO_2$ | 1 | Atomic bond | (2-Cl)Phenyl |

Typical Compound Example B-500

[Formula 18]

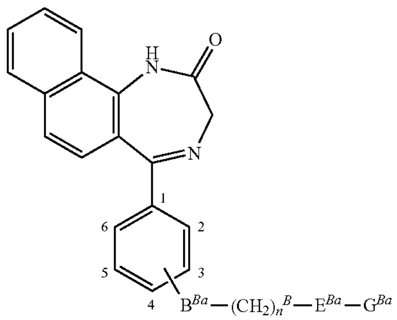

($B^{Ba}$ (substitution position), $n^B$, $E^{Ba}$, and $G^{Ba}$ in the formula are indicated in Table 22)

TABLE 22

| $B^{Ba}$(substitution position) | $n^B$ | $E^{Ba}$ | $G^{Ba}$ |
|---|---|---|---|
| NHCO(4) | 0 | Atomic bond | (2-Cl,3-OMe)Phenyl |
| NHCO(4) | 0 | Atomic bond | (2-Cl,3-OH)Phenyl |
| NHCO(4) | 0 | Atomic bond | (2-tBu)Phenyl |
| NHCO(4) | 0 | Atomic bond | (2-Cl,6-OMe)Phenyl |
| NHCO(4) | 0 | Atomic bond | (2-Cl,6-OH)Phenyl |
| $NHSO_2(3)$ | 0 | Atomic bond | Phenyl |
| $NHSO_2(4)$ | 0 | Atomic bond | (2-Cl)Phenyl |

Typical Compound Example B-600

[Formula 19]

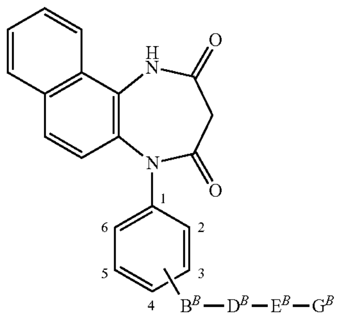

($B^B$ (substitution position), $D^B$, $E^B$, and $G^B$ in the formula are indicated in Table 23)

TABLE 23

| $B^B$(substitution position) | $D^B$ | $E^B$ | $G^B$ |
|---|---|---|---|
| NHCO(4) | C(Me)H | Atomic bond | Phenyl |
| NHCO(4) | $C(Me)_2$ | Atomic bond | Phenyl |
| NHCO(4) | CH═CH | Atomic bond | Phenyl |
| NHCO(4) | C(Me)H | O | Phenyl |
| NHCO(4) | $C(Me)_2$ | O | Phenyl |
| NHCO(4) | CH═CH | Atomic bond | (2-Me)Phenyl |
| NHCO(4) | CH═CH | Atomic bond | (2-Cl)Phenyl |

Typical Compound Example B-700

[Formula 20]

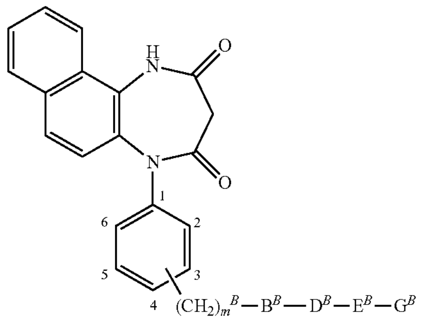

($m^B$ (substitution position), $B^B$, $D^B$, $E^B$, and $G^B$ in the formula are indicated in Table 24)

TABLE 24

| $m^B$(substitution position) | $B^B$ | $D^B$ | $E^B$ | $G^B$ |
|---|---|---|---|---|
| 1(4) | NHCO | Atomic bond | Atomic bond | Phenyl |
| 1(4) | NHCO | Atomic bond | Atomic bond | (2-Cl)Phenyl |
| 1(4) | $NHSO_2$ | $CH_2$ | Atomic bond | (2-Cl)Phenyl |

Typical Compound Example B-800

[Formula 21]

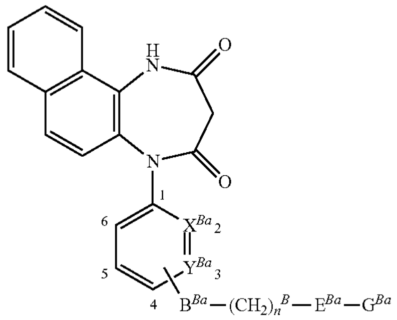

($X^{Ba}$, $Y^{Ba}$, $B^{Ba}$ (substitution position), $n^B$, $E^{Ba}$, and $G^{Ba}$ in the formula are indicated in Table 25)

TABLE 25

| $X^{Ba}$ | $Y^{Ba}$ | $B^{Ba}$(substitution position) | $n^B$ | $E^{Ba}$ | $G^{Ba}$ |
|---|---|---|---|---|---|
| CH | C—F | NHCO(4) | 0 | Atomic bond | (2,3-Me)Phenyl |
| CH | C—OH | NHCO(4) | 0 | Atomic bond | (2,3-Me)Phenyl |
| CH | C—F | NHCO(4) | 0 | Atomic bond | (2-I)Phenyl |
| CH | N | NHCO(4) | 0 | Atomic bond | (2-I)Phenyl |
| CH | N | NHCO(4) | 0 | Atomic bond | Phenyl |
| N | CH | NHCO(4) | 0 | Atomic bond | (2-I)Phenyl |
| CH | N | NHCO(4) | 0 | Atomic bond | (2-Cl)Phenyl |
| CH | N | NHCO(4) | 0 | Atomic bond | (2-OH)Phenyl |
| CH | N | NHC(═O)NH(4) | 0 | Atomic bond | (2-OH)Phenyl |
| CH | N | NHCO(4) | 0 | Atomic bond | (2-OH,6-Me)Phenyl |

TABLE 25-continued

| $X^{Ba}$ | $Y^{Ba}$ | $B^{Ba}$(substitution position) | $n^B$ | $E^{Ba}$ | $G^{Ba}$ |
|---|---|---|---|---|---|
| CH | N | NHCO(4) | 0 | Atomic bond | (2-OH,6-Cl)Phenyl |
| CH | N | NHCO(3) | 0 | Atomic bond | (2-OH,6-Cl)Phenyl |
| CH | N | NHCO(4) | 0 | Atomic bond | (2-Cl) pyridin 2-yl |
| CH | N | NHCO(4) | 1 | Atomic bond | (2-Cl) pyridin 2-yl |
| CH | N | NHCO(4) | 0 | Atomic bond | (2-Me) pyridin 2-yl |
| CH | C—OMe | NHSO2(4) | 1 | Atomic bond | (2-Cl)Phenyl |
| CH | C—OH | NHSO2(4) | 1 | Atomic bond | (2-Cl)Phenyl |

Typical Compound Example B-900

[Formula 22]

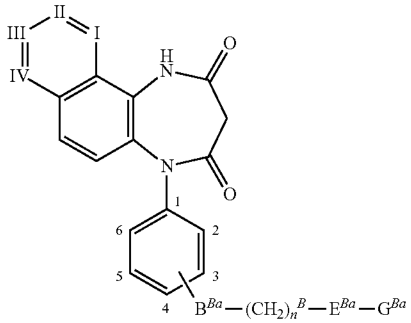

(I=II-III=IV, $B^{Ba}$ (substitution position), $n^B$, $E^{Ba}$, and $G^{Ba}$ in the formula are indicated in Table 26)

TABLE 26

| I═II—III═IV | $B^{Ba}$(substitution position) | $n^B$ | $E^{Ba}$ | $G^{Ba}$ |
|---|---|---|---|---|
| N═CH—CH═CH | NHCO(4) | 0 | Atomic bond | (2-I)Phenyl |
| CH═N—CH═CH | NHCO(4) | 0 | Atomic bond | (2-I)Phenyl |
| CH═CH—N═CH | NHCO(4) | 0 | Atomic bond | (2-I)Phenyl |
| CH═CH—CH═N | NHCO(4) | 0 | Atomic bond | (2-I)Phenyl |
| N═CH—CH═CH | NHCO(4) | 1 | O | Phenyl |
| N═CH—CH═CH | NHCO(3) | 0 | Atomic bond | (2-1)Phenyl |
| N═CH—CH═CH | NHCO(4) | 0 | Atomic bond | (2-Cl)Phenyl |
| N═CH—CH═CH | NHCO(4) | 0 | Atomic bond | (2-OH)Phenyl |
| N═CH—CH═CH | NHC(═O)NH(4) | 0 | Atomic bond | (2-OH)Phenyl |

TABLE 26-continued

| I═II—III═IV | $B^{Ba}$(substitution position) | $n^B$ | $E^{Ba}$ | $G^{Ba}$ |
|---|---|---|---|---|
| N═CH—CH═CH | NHCO(4) | 1 | O | (2-OH,6-Me)Phenyl |
| N═CH—CH═CH | NHCO(4) | 0 | Atomic bond | (2-OH,6-Cl)Phenyl |
| N═CH—CH═CH | NHCO(3) | 0 | Atomic bond | (2-OH,6-Cl)Phenyl |
| N═CH—CH═CH | NHCO(4) | 0 | Atomic bond | (2-Cl) pyridin 2-yl |
| N═CH—CH═CH | NHCO(4) | 1 | Atomic bond | (2-Cl) pyridin 2-yl |
| N═CH—CH═CH | NHCO(4) | 0 | Atomic bond | (2-Me) pyridin 2-yl |
| CH═CH—N═CH | NHCO(4) | 0 | Atomic bond | (2-Cl) pyridin 3-yl |

Typical Compound Example B-1000

[Formula 23]

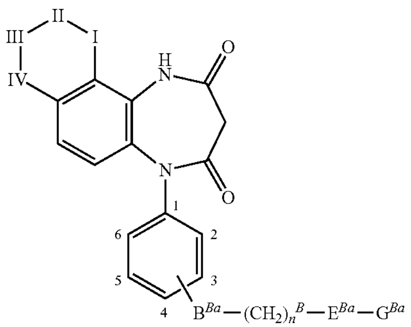

(I-II-III-IV, $B^{Ba}$ (substitution position), $n^B$, $E^{Ba}$, and $G^{Ba}$ in the formula are indicated in Table 27)

TABLE 27

| I—II—III—IV | $B^{Ba}$(substitution position) | $n^B$ | $E^{Ba}$ | $G^{Ba}$ |
|---|---|---|---|---|
| $NH—CH_2—CH_2—CH_2$ | NHCO(4) | 0 | Atomic bond | (2-I)Phenyl |
| $CH_2—NH—CH_2—CH_2$ | NHCO(4) | 0 | Atomic bond | (2-I)Phenyl |
| $CH_2—CH_2—NH—CH_2$ | NHCO(4) | 0 | Atomic bond | (2-I)Phenyl |
| $CH_2—CH_2—CH_2—NH$ | NHCO(4) | 0 | Atomic bond | (2-I)Phenyl |
| $CH_2—CH_2—NH—CH_2$ | NHCO(4) | 1 | O | Phenyl |
| $CH_2—CH_2—NH—CH_2$ | NHCO(3) | 0 | Atomic bond | (2-I)Phenyl |
| $CH_2—CH_2—NH—CH_2$ | NHCO(4) | 0 | Atomic bond | (2-Cl)Phenyl |
| $CH_2—CH_2—NH—CH_2$ | NHCO(4) | 0 | Atomic bond | (2-Cl) pyridin 3-yl |
| $CH_2—CH_2—NH—CH_2$ | NHCO(4) | 0 | Atomic bond | (2-OH)Phenyl |
| $CH_2—CH_2—NH—CH_2$ | NHC(═O)NH(4) | 0 | Atomic bond | (2-OH)Phenyl |
| $CH_2—CH_2—NH—CH_2$ | NHCO(4) | 1 | O | (2-OH,6-Me)Phenyl |
| $CH_2—CH_2—NH—CH_2$ | NHCO(4) | 0 | Atomic bond | (2-OH,6-Cl)Phenyl |
| $CH_2—CH_2—NH—CH_2$ | NHCO(3) | 0 | Atomic bond | (2-OH,6-Cl)Phenyl |
| $CH_2—CH_2—NH—CH_2$ | NHCO(4) | 0 | Atomic bond | (2-Cl) pyridin 2-yl |
| $CH_2—CH_2—NH—CH_2$ | NHCO(4) | 1 | Atomic bond | (2-Cl) pyridin 2-yl |
| $CH_2—CH_2—NH—CH_2$ | NHCO(4) | 0 | Atomic bond | (2-Me) pyridin 2-yl |
| $CH_2—CH_2—NH—CH_2$ | NHCO(4) | 0 | Atomic bond | (2-Cl) pyridin 3-yl |

Typical Compound Example B-1100

[Formula 24]

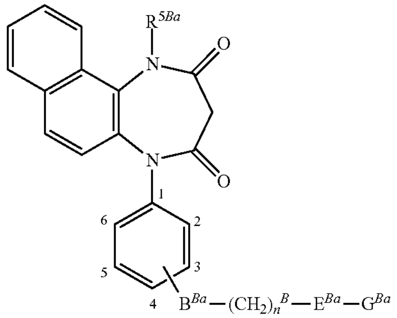

($R^{5Ba}$, $B^{Ba}$ (substitution position), $n^B$, $E^{Ba}$, and $G^{Ba}$ in the formula are indicated in Table 28)

TABLE 28

| $R^{5Ba}$ | $B^{Ba}$(substitution position) | $n^B$ | $E^{Ba}$ | $G^{Ba}$ |
|---|---|---|---|---|
| Bn | $NBnSO_2(4)$ | 0 | Atomic bond | $(2\text{-}NO_2)$Phenyl |
| Me | $NBnSO_2(4)$ | 0 | Atomic bond | $(2\text{-}NO_2)$Phenyl |
| Et | $NBnSO_2(4)$ | 0 | Atomic bond | $(2\text{-}NO_2)$Phenyl |

Since the compounds represented by the general formula (A) are disclosed in WO 2010/093061 A, all of the compounds can be easily obtained by referring to this international publication. The disclosure of this international publication is incorporated herein by reference in its entirety.

Since the compounds represented by the general formulas (BI) and (BII) are disclosed in WO 2013/105608 A, all of the compounds can be easily obtained by referring to this international publication. The disclosure of this international publication is incorporated herein by reference in its entirety.

Furthermore, WO 2010/093061 A, WO 2013/105608 A and WO 2015/005467 A disclose that the compounds represented by the general formulas (A) to (BII) have a P2X4 receptor antagonistic action.

Specific examples of a preferable compound comprised in the compounds represented by the general formulas (A) to (BII) or a pharmaceutically acceptable salt thereof are shown below, however, the compound or a pharmaceutically acceptable salt thereof that can be used as the active ingredient of the pharmaceutical composition of the present invention is not limited thereto.

(Compound A1) 5-[3-(1H-tetrazol-5-yl)phenyl]-1H-naphtho[1,2-b][1,4]diazepine-2,4(3H,5H)-dione;

(Compound A2) 5-[3-(1H-tetrazol-5-yl)phenyl]-1H-naphtho[1,2-b][1,4]diazepine-2,4(3H,5H)-dione sodium salt;

(Compound A3) 5-[3-(1H-tetrazol-5-yl)phenyl]-1H-naphtho[1,2-b][1,4]diazepine-2,4(3H,5H)-dione potassium salt;

(Compound A4) 5-[4-(1H-tetrazol-5-yl)phenyl]-1H-naphtho[1,2-b][1,4]diazepine-2,4(3H,5H)-dione;

(Compound A5) 5-[4-(1H-tetrazol-5-yl)phenyl]-1H-naphtho[1,2-b][1,4]diazepine-2,4(3H,5H)-dione sodium salt;

(Compound A6) 1-methyl-5-[3-(1H-tetrazol-5-yl)phenyl]-1H-naphtho[1,2-b][1,4]diazepine-2,4(3H,5H)-dione;

(Compound A7) 1,3-dimethyl-5-[3-(1H-tetrazol-5-yl)phenyl]-1H-naphtho[1,2-b][1,4]diazepine-2,4(3H,5H)-dione;

(Compound A8) 5-[2-chloro-5-(1H-tetrazol-5-yl)phenyl]-1H-naphtho[1,2-b][1,4]diazepine-2,4(3H,5H)-dione;

(Compound A9) 5-[2-chloro-5-(1H-tetrazol-5-yl)phenyl]-1H-naphtho[1,2-b][1,4]diazepine-2,4(3H,5H)-dione sodium salt;

(Compound A10) 5-[2-methyl-5-(1H-tetrazol-5-yl)phenyl]-1H-naphtho[1,2-b][1,4]diazepine-2,4(3H,5H)-dione;

(Compound A11) 5-[2-methyl-5-(1H-tetrazol-5-yl)phenyl]-1H-naphtho[1,2-b][1,4]diazepine-2,4(3H,5H)-dione sodium salt;

(Compound A12) 5-[2-bromo-5-(1H-tetrazol-5-yl)phenyl]-1H-naphtho[1,2-b][1,4]diazepine-2,4(3H,5H)-dione;

(Compound A13) 5-[3-(2-methyl-2H-tetrazol-5-yl)phenyl]-1H-naphtho[1,2-b][1,4]diazepine-2,4(3H,5H)-dione;

(Compound A14) 5-[3-(1-methyl-1H-tetrazol-5-yl)phenyl]-1H-naphtho[1,2-b][1,4]diazepine-2,4(3H,5H)-dione;

(Compound A15) 5-[3-(5-oxo-4H-[1,2,4]oxadiazol-3-yl)phenyl]-1H-naphtho[1,2-b][1,4]diazepine-2,4(3H,5H)-dione;

(Compound A16) 5-[3-(5-thioxo-4H-[1,2,4]oxadiazol-3-yl)phenyl]-1H-naphtho[1,2-b][1,4]diazepine-2,4(3H,5H)-dione;

(Compound A17) 5-[3-(5-thioxo-4H-[1,2,4]oxadiazol-3-yl)phenyl]-1H-naphtho[1,2-b][1,4]diazepine-2,4(3H,5H)-dione sodium salt;

(Compound A18) 5-[3-(oxazol-2-yl)phenyl]-1H-naphtho[1,2-b][1,4]diazepine-2,4(3H,5H)-dione;

(Compound A19) 5-[3-(1H-pyrazol-4-yl)phenyl]-1H-naphtho[1,2-b][1,4]diazepine-2,4(3H,5H)-dione;

(Compound A20) 5-[4-fluoro-3-(1H-tetrazol-5-yl)phenyl]-1H-naphtho[1,2-b][1,4]diazepine-2,4(3H,5H)-dione;

(Compound A21) 5-[4-fluoro-3-(1H-tetrazol-5-yl)phenyl]-1H-naphtho[1,2-b][1,4]diazepine-2,4(3H,5H)-dione sodium salt;

(Compound B1) 5-(4-benzoylaminophenyl)-1H-naphtho[1,2-b][1,4]diazepine-2,4(3H,5H)-dione;

(Compound B2) 5-[4-[2-(trifluoromethyl)benzoyl]aminophenyl]-1H-naphtho[1,2-b][1,4]diazepine-2,4(3H,5H)-dione;

(Compound B3) 5-[4-(3-bromobenzoyl)aminophenyl]-1H-naphtho[1,2-b][1,4]diazepine-2,4(3H,5H)-dione;

(Compound B4) 5-[4-[4-(trifluoromethyl)benzoyl]aminophenyl]-1H-naphtho[1,2-b][1,4]diazepine-2,4(3H,5H)-dione;

(Compound B5) 5-[4-(2-methylbenzoyl)aminophenyl]-1H-naphtho[1,2-b][1,4]diazepine-2,4(3H,5H)-dione;

(Compound B6) 5-[4-(2,6-dimethylbenzoylamino)phenyl]-1H-naphtho[1,2-b][1,4]diazepine-2,4(3H,5H)-dione;

(Compound B7) 5-[4-(2,6-dichlorobenzoyl)aminophenyl]-1H-naphtho[1,2-b][1,4]diazepine-2,4(3H,5H)-dione;

(Compound B8) 5-[4-(3-chlorobenzoyl)aminophenyl]-1H-naphtho[1,2-b][1,4]diazepine-2,4(3H,5H)-dione;

(Compound B9) 5[4-(2-phenylacetylamino)phenyl]-1H-naphtho[1,2-b][1,4]diazepine-2,4(3H,5H)-dione;

(Compound B10) 1-[4-(2,4-dioxo-1,2,3,4-tetrahydronaphtho[1,2-b][1,4]diazepin-5-yl)phenyl]-3-phenylthiourea;

(Compound B11) 5-[4-(2,3-dimethoxybenzoylamino)phenyl]-1H-naphtho[1,2-b][1,4]diazepine-2,4(3H,5H)-dione;

(Compound B12) 5-[4-(2-methoxybenzoylamino)phenyl]-1H-naphtho[1,2-b][1,4]diazepine-2,4(3H,5H)-dione;

(Compound B13) 5-[4-[(2-chlorophenylacetyl)amino]phenyl]-1H-naphtho[1,2-b][1,4]diazepine-2,4(3H,5H)-dione;

(Compound B14) 5-[4-(2,3-dimethylbenzoylamino)phenyl]-1H-naphtho[1,2-b][1,4]diazepine-2,4(3H,5H)-dione;

(Compound B15) 5-[4-(2,5-dimethylbenzoylamino)phenyl]-1H-naphtho[1,2-b][1,4]diazepine-2,4(3H,5H)-dione;

(Compound B16) 5-[4-(5-bromo-2-chlorobenzoylamino)phenyl]-1H-naphtho[1,2-b][1,4]diazepine-2,4(3H,5H)-dione;

(Compound B17) 5-[4-(2,4-dichlorobenzoylamino)phenyl]-1H-naphtho[1,2-b][1,4]diazepine-2,4(3H,5H)-dione;

(Compound B18) 5-[4-(2-hydroxybenzoylamino)phenyl]-1H-naphtho[1,2-b][1,4]diazepine-2,4(3H,5H)-dione;

(Compound B19) 5-[4-(2,3-dihydroxybenzoylamino)phenyl]-1H-naphtho[1,2-b][1,4]diazepine-2,4(3H,5H)-dione;

(Compound B20) 1-[4-(2,4-dioxo-1,2,3,4-tetrahydronaphtho[1,2-b][1,4]diazepin-5-yl)phenyl]-3-phenylurea;

(Compound B21) 5-[4-[(2,6-dichlorophenylacetyl)amino]phenyl]-1H-naphtho[1,2-b][1,4]diazepine-2,4(3H,5H)-dione;

(Compound B22) 5-[4-[(2-methoxyphenylacetyl)amino]phenyl]-1H-naphtho[1,2-b][1,4]diazepine-2,4(3H,5H)-dione;

(Compound B23) 5-[4-[(2-hydroxyphenylacetyl)amino]phenyl]-1H-naphtho[1,2-b][1,4]diazepine-2,4(3H,5H)-dione;

(Compound B24) 1-(2-chlorophenyl)-3-[4-(2,4-dioxo-1,2,3,4-tetrahydronaphtho[1,2-b][1,4]diazepin-5-yl)phenyl]thiourea;

(Compound B25) 5-[4-[3-(trifluoromethyl)benzoylamino]phenyl]-1H-naphtho[1,2-b][1,4]diazepine-2,4(3H,5H)-dione;

(Compound B26) 5-[4-[2-[2-(trifluoromethyl)phenyl]acetylamino]phenyl]-1H-naphtho[1,2-b][1,4]diazepine-2,4(3H,5H)-dione;

(Compound B27) 1-(2-chlorophenyl)-3-[4-(2,4-dioxo-1,2,3,4-tetrahydronaphtho[1,2-b][1,4]diazepin-5-yl)phenyl]urea;

(Compound B28) 5-[4-[(2-phenylpropionyl)amino]phenyl]-1H-naphtho[1,2-b][1,4]diazepine-2,4(3H,5H)-dione;

(Compound B29) 5-[4-(2-chloro-3-methoxybenzoylamino)phenyl]-1H-naphtho[1,2-b][1,4]diazepine-2,4(3H,5H)-dione;

(Compound B30) 5-[4-(3-phenylpropionylamino)phenyl]-1H-naphtho[1,2-b][1,4]diazepine-2,4(3H,5H)-dione;

(Compound B31) 5-[4-[(1H-indole-3-carbonyl)amino]phenyl]-1H-naphtho[1,2-b][1,4]diazepine-2,4(3H,5H)-dione;

(Compound B32) 5-[4-(2-chloro-3-hydroxybenzoylamino)phenyl]-1H-naphtho[1,2-b][1,4]diazepine-2,4(3H,5H)-dione;

(Compound B33) 5-[4-[(2-methyl-2-phenylpropionyl)amino]phenyl]-1H-naphtho[1,2-b][1,4]diazepine-2,4(3H,5H)-dione;

(Compound B34) 5-[4-(2-phenoxyacetylamino)phenyl]-1H-naphtho[1,2-b][1,4]diazepine-2,4(3H,5H)-dione;

(Compound B35) 5-[4-[2-(2-chloro-4-methoxyphenyl)acetylamino]phenyl]-1H-naphtho[1,2-b][1,4]diazepine-2,4(3H,5H)-dione;

(Compound B36) 5-[4-[(1-methyl-1H-imidazole-2-carbonyl)amino]phenyl]-1H-naphtho[1,2-b][1,4]diazepine-2,4(3H,5H)-dione;

(Compound B37) 5-[4-[2-(2,4-dichlorophenyl)acetylamino]phenyl]-1H-naphtho[1,2-b][1,4]diazepine-2,4(3H,5H)-dione;

(Compound B38) 5-[4-[2-(2-chloro-4-hydroxyphenyl)acetylamino]phenyl]-1H-naphtho[1,2-b][1,4]diazepine-2,4(3H,5H)-dione;

(Compound B39) 5-[4-(3-phenylpropenylamino)phenyl]-1H-naphtho[1,2-b][1,4]diazepine-2,4(3H,5H)-dione;

(Compound B40) 5-[4-[(3-pyridylacetyl)amino]phenyl]-1H-naphtho[1,2-b][1,4]diazepine-2,4(3H,5H)-dione hydrochloride;

(Compound B41) 5-[4-(1H-benzimidazole-2-carbonylamino)phenyl]-1H-naphtho[1,2-b][1,4]diazepine-2,4(3H,5H)-dione;

(Compound B42) 1-[4-(2,3-dimethylbenzoylamino)phenyl]-7-methoxy-1H-1,5-benzodiazepine-2,4(3H,5H)-dione;

(Compound B43) 5-[4-[(benzoylamino)methyl]phenyl]-1H-naphtho[1,2-b][1,4]diazepine-2,4(3H,5H)-dione;

(Compound B44) 5-[4-[(2-chlorobenzoylamino)methyl]phenyl]-1H-naphtho[1,2-b][1,4]diazepine-2,4(3H,5H)-dione;

(Compound B45) 1-[4-(2,3-dimethylbenzoylamino)phenyl]-7-hydroxy-1H-1,5-benzodiazepine-2,4(3H,5H)-dione;

(Compound B46) 5-[4-(2-chlorobenzoylamino)phenyl]-1H-naphtho[1,2-b][1,4]diazepine-2,4(3H,5H)-dione;

(Compound B47) 5-[4-(2-bromobenzoylamino)phenyl]-1H-naphtho[1,2-b][1,4]diazepine-2,4(3H,5H)-dione;

(Compound B48) 5-[4-(2-iodobenzoylamino)phenyl]-1H-naphtho[1,2-b][1,4]diazepine-2,4(3H,5H)-dione;

(Compound B49) 5-[4-(2,3-dimethylbenzoylamino)-3-fluorophenyl]-1H-naphtho[1,2-b][1,4]diazepine-2,4(3H,5H)-dione;

(Compound B50) 5-[4-[2-(2-methylphenyl)acetylamino]phenyl]-1H-naphtho[1,2-b][1,4]diazepine-2,4(3H,5H)-dione;

(Compound B51) 5-[4-[(quinoxalin-2-yl)carbonylamino]phenyl]-1H-naphtho[1,2-b][1,4]diazepine-2,4(3H,5H)-dione;

(Compound B52) 5-[4-[(5-methylthiophen-2-yl)carbonylamino]phenyl]-1H-naphtho[1,2-b][1,4]diazepine-2,4(3H,5H)-dione;

(Compound B53) 5-[3-[(2-chlorophenylacetyl)amino]phenyl]-1H-naphtho[1,2-b][1,4]diazepine-2,4(3H,5H)-dione;

(Compound B54) 5-[4-[(2,4,6-trimethylbenzoyl)amino]phenyl]-1H-naphtho[1,2-b][1,4]diazepine-2,4(3H,5H)-dione;

(Compound B55) 5-[4-(cyclohexylcarbonylamino)phenyl]-1,2,3,4,8,9,10,11-octahydronaphtho[1,2-b][1,4]diazepine-2,4(3H,5H)-dione;

(Compound B56) 1-[4-(2,3-dimethylbenzoyl)aminophenyl]-6-methyl-1H-1,5-benzodiazepine-2,4(3H,5H)-dione;

(Compound B57) 5-[4-[(2-ethylbenzoyl)amino]phenyl]-1H-naphtho[1,2-b][1,4]diazepine-2,4(3H,5H)-dione;

(Compound B58) 5-[4-[(6-methylpyridin-2-yl)carbonylamino]phenyl]-1,2,3,4,8,9,10,11-octahydronaphtho[1,2-b][1,4]diazepine-2,4(3H,5H)-dione;

(Compound B59) 5-[4-[(2-methylpyridin-3-yl)carbonylamino]phenyl]-1,2,3,4,8,9,10,11-octahydronaphtho[1,2-b][1,4]diazepine-2,4(3H,5H)-dione;

(Compound B60) 1-[4-(2,4-dioxo-1,2,3,4-tetrahydronaphtho[1,2-b][1,4]diazepin-5-yl)phenyl]-3-(2-methylphenyl)thiourea;

(Compound B61) 5-[4-(2-methoxy-3-methylbenzoyl)aminophenyl]-1,2,3,4,8,9,10,11-octahydronaphtho[1,2-b][1,4]diazepine-2,4(3H,5H)-dione;

(Compound B62) 5-[4-(2,3-dichlorobenzoyl)aminophenyl]-1,2,3,4,8,9,10,11-octahydronaphtho[1,2-b][1,4]diazepine-2,4(3H,5H)-dione;

(Compound B63) 5-[4-(2,3-dimethylbenzoylamino)-3-hydroxyphenyl]-1H-naphtho[1,2-b][1,4]diazepine-2,4(3H,5H)-dione;

(Compound B64) 5-[4-(2-chloro-3-methoxybenzoylamino)phenyl]-1,3-dihydronaphtho[1,2-e]-1,4-diazepin-2-one;

(Compound B65) 5-[4-[(4-dimethylaminobenzoyl)amino]phenyl]-1H-naphtho[1,2-b][1,4]diazepine-2,4(3H,5H)-dione;

(Compound B66) 5-[4-[2-(2,4-dichlorophenoxy)acetylamino]phenyl]-1H-naphtho[1,2-b][1,4]diazepine-2,4(3H,5H)-dione;

(Compound B67) 5-[4-[2-(2-methylphenoxy)acetylamino]phenyl]-1H-naphtho[1,2-b][1,4]diazepine-2,4(3H,5H)-dione;

(Compound B68)N-[4-(2,4-dioxo-1,2,3,4-tetrahydronaphtho[1,2-b][1,4]diazepin-5-yl)butyl]-2-chloro-3-methoxybenzamide;

(Compound B69) 5-[4-(2-chloro-3-hydroxybenzoylamino)phenyl]-1,3-dihydronaphtho[1,2-e]-1,4-diazepin-2-one;

(Compound B70) 5-[4-(2-acetylbenzoylamino)phenyl]-1H-naphtho[1,2-b][1,4]diazepine-2,4(3H,5H)-dione;

(Compound B71) 5-[4-(2-tert-butylbenzoylamino)phenyl]-1H-naphtho[1,2-b][1,4]diazepine-2,4(3H,5H)-dione;

(Compound B72) 5-[2-(2-iodobenzoyl)aminoethyl]-1H-naphtho[1,2-b][1,4]diazepine-2,4(3H,5H)-dione;

(Compound B73) 5-[3-[(2-iodobenzoyl)amino]phenyl]-1H-naphtho[1,2-b][1,4]diazepine-2,4(3H,5H)-dione;

(Compound B74) 6,7-dimethyl-1-[4-(2-iodobenzoyflaminophenyl]-1H-1,5-benzodiazepine-2,4(3H,5H)-dione;

(Compound B75) 5-[4-[(1-methylpiperidin-4-yl)carbonylamino]phenyl]-1H-naphtho[1,2-b][1,4]diazepine-2,4(3H,5H)-dione hydrochloride;

(Compound B76) 5[4-[(benzofuran-2-yl)carbonylamino]phenyl]-1H-naphtho[1,2-b][1,4]diazepine-2,4(3H,5H)-dione;

(Compound B77) 5-[4-[(1-methyl-1H-indol-3-yl)carbonylamino]phenyl]-1H-naphtho[1,2-b][1,4]diazepine-2,4(3H,5H)-dione;

(Compound B78) 5-[4-(2-propenylbenzoylamino)phenyl]-1H-naphtho[1,2-b][1,4]diazepine-2,4(3H,5H)-dione;

(Compound B79) 5-[4-(2-propylbenzoylamino)phenyl]-1H-naphtho[1,2-b][1,4]diazepine-2,4(3H,5H)-dione;

(Compound B80) 5-[3-fluoro-4-(2-iodobenzoylamino)phenyl]-1H-naphtho[1,2-b][1,4]diazepine-2,4(3H,5H)-dione;

(Compound B81) 5-[4-(2-hydroxy-3-methylbenzoyl)aminophenyl]-1,2,3,4,8,9,10,11-octahydronaphtho[1,2-b][1,4]diazepine-2,4(3H,5H)-dione;

(Compound B82) 5-[4-[(2-isopropoxybenzoyl)amino]phenyl]-1H-naphtho[1,2-b][1,4]diazepine-2,4(3H,5H)-dione;

(Compound B83) 5-[4-[(3-methylthiophen-2-yl)carbonylamino]phenyl]-1H-naphtho[1,2-b][1,4]diazepine-2,4(3H,5H)-dione;

(Compound B84) 5-[4-(2-phenoxypropionylamino)phenyl]-1H-naphtho[1,2-b][1,4]diazepine-2,4(3H,5H)-dione;

(Compound B85) 5-[4-[2-(4-chloro-2-methylphenoxy)acetylamino]phenyl]-1H-naphtho[1,2-b][1,4]diazepine-2,4(3H,5H)-dione;

(Compound B86) 5-[4-[(4-fluoro-2-trifluoromethyl)benzoyl]aminophenyl]-1H-naphtho[1,2-b][1,4]diazepine-2,4(3H,5H)-dione;

(Compound B87) 5-[4-(4-fluoro-2-methoxybenzoyl)aminophenyl]-1H-naphtho[1,2-b][1,4]diazepine-2,4(3H,5H)-dione;

(Compound B88) 5-[4-(4-fluoro-2-hydroxybenzoyl)aminophenyl]-1H-naphtho[1,2-b][1,4]diazepine-2,4(3H,5H)-dione;

(Compound B89) 5-[3-[(2-iodophenylacetyl)amino]phenyl]-1H-naphtho[1,2-b][1,4]diazepine-2,4(3H,5H)-dione;

(Compound B90) 5-[4-(2-methyl-2-phenoxypropionylamino)phenyl]-1H-naphtho[1,2-b][1,4]diazepine-2,4(3H,5H)-dione;

(Compound B91) 5-[4-(2-tert-butylbenzoylamino)phenyl]-1,3-dihydronaphtho[1,2-e]-1,4-diazepin-2-one;

(Compound B92) 5-[4-[(3-dimethylaminobenzoyl)amino]phenyl]-1H-naphtho[1,2-b][1,4]diazepine-2,4(3H,5H)-dione;

(Compound B93) 5-[4-(4-iodo-2-methoxybenzoylamino)phenyl]-1H-naphtho[1,2-b][1,4]diazepine-2,4(3H,5H)-dione;

(Compound B94) 5-[4-(6-fluoro-2-methoxybenzoylamino)phenyl]-1H-naphtho[1,2-b][1,4]diazepine-2,4(3H,5H)-dione;

(Compound B95) 5-[4-(2-hydroxy-4-iodobenzoylamino)phenyl]-1H-naphtho[1,2-b][1,4]diazepine-2,4(3H,5H)-dione;

(Compound B96) 5-[4-(6-fluoro-2-hydroxybenzoylamino)phenyl]-1H-naphtho[1,2-b][1,4]diazepine-2,4(3H,5H)-dione;

(Compound B97) 5-[4-(2-fluorobenzoyl)aminophenyl]-1H-naphtho[1,2-b][1,4]diazepine-2,4(3H,5H)-dione;

(Compound B98) 5-[4-[(2-dimethylaminobenzoyl)amino]phenyl]-1H-naphtho[1,2-b][1,4]diazepine-2,4(3H,5H)-dione;

(Compound B99) 5-[4-(2-methoxy-6-methylbenzoylamino)phenyl]-1H-naphtho[1,2-b][1,4]diazepine-2,4(3H,5H)-dione;

(Compound B100) 5-[4-(2-hydroxy-6-methylbenzoylamino)phenyl]-1H-naphtho[1,2-b][1,4]diazepine-2,4(3H,5H)-dione;

(Compound B101) 5-[4-[3-(2-methylphenyl)propionylamino]phenyl]-1H-naphtho[1,2-b][1,4]diazepine-2,4(3H,5H)-dione;

(Compound B102) 5-(4-phenylcarbamoylphenyl)-1H-naphtho[1,2-b][1,4]diazepine-2,4(3H,5H)-dione;

(Compound B103) 5-(4-benzylcarbamoylphenyl)-1H-naphtho[1,2-b][1,4]diazepine-2,4(3H,5H)-dione;

(Compound B104) 5-[4-[3-(2-methylphenyl)propenoylamino]phenyl]-1H-naphtho[1,2-b][1,4]diazepine-2,4(3H,5H)-dione;

(Compound B105) 5-[4-[3-(2-chlorophenyl)propionylamino]phenyl]-1H-naphtho[1,2-b][1,4]diazepine-2,4(3H,5H)-dione;

(Compound B106) 5-[4-(2-iodobenzoyl)aminophenyl]-1,2,3,4,8,9,10,11-octahydronaphtho[1,2-b][1,4]diazepine-2,4(3H,5H)-dione;

(Compound B107) 5-[4-[(1-methyl-1H-pyrrol-2-ylacetyl)amino]phenyl]-1,2,3,4,8,9,10,11-octahydronaphtho[1,2-b][1,4]diazepine-2,4(3H,5H)-dione;

(Compound B108) 5-[4-(2-chlorobenzyl)carbamoylphenyl]-1H-naphtho[1,2-b][1,4]diazepine-2,4(3H,5H)-dione;

(Compound B109) 5-[4-[3-(2-chlorophenyl)propenoylamino]phenyl]-1H-naphtho[1,2-b][1,4]diazepine-2,4(3H,5H)-dione;

(Compound B110) 5-[4-(2-chlorophenyl)carbamoylphenyl]-1H-naphtho[1,2-b][1,4]diazepine-2,4(3H,5H)-dione;

(Compound B111) 5-[4-(6-bromo-2,3-methylenedioxybenzoylamino)phenyl]-1H-naphtho[1,2-b][1,4]diazepine-2,4(3H,5H)-dione;

(Compound B112) 5-[4-(6-bromo-2-methoxybenzoylamino)phenyl]-1H-naphtho[1,2-b][1,4]diazepine-2,4(3H,5H)-dione;

(Compound B113) 5-[4-[(2-tert-butylbenzoyl)amino]phenyl]-1,2,3,4,8,9,10,11-octahydronaphtho[1,2-b][1,4]diazepine-2,4(3H,5H)-dione;

(Compound B114) 5-[2-(2-iodobenzoyl)aminopyridin-5-yl]-1H-naphtho[1,2-b][1,4]diazepine-2,4(3H,5H)-dione;

(Compound B115) 5-[4-(6-bromo-2-hydroxybenzoylamino)phenyl]-1H-naphtho[1,2-b][1,4]diazepine-2,4(3H,5H)-dione;

(Compound B116) 5-[4-(6-chloro-2-methoxybenzoylamino)phenyl]-1H-naphtho[1,2-b][1,4]diazepine-2,4(3H,5H)-dione;

(Compound B117) 5-[4-(2-iodobenzoylamino)phenyl]-1H-[1,4]diazepino[2,3-h]quinoline-2,4(3H,5H)-dione;

(Compound B118) 5-[4-(6-chloro-2-hydroxybenzoylamino)phenyl]-1H-naphtho[1,2-b][1,4]diazepine-2,4(3H,5H)-dione;

(Compound B119) 5-[4-(2-hydroxy-6-methoxybenzoylamino)phenyl]-1H-naphtho[1,2-b][1,4]diazepine-2,4(3H,5H)-dione;

(Compound B120) 5-[4-[2-methoxy-6-(trifluoromethyl)benzoylamino]phenyl]-1H-naphtho[1,2-b][1,4]diazepine-2,4(3H,5H)-dione;

(Compound B121) 5-[4-[2-hydroxy-6-(trifluoromethyl)benzoylamino]phenyl]-1H-naphtho[1,2-b][1,4]diazepine-2,4(3H,5H)-dione;

(Compound B122) 5-[4-[(2-isopropenylbenzoyl)amino]phenyl]-1,2,3,4,8,9,10,11-octahydronaphtho[1,2-b][1,4]diazepine-2,4(3H,5H)-dione;

(Compound B123) 5-[4-[(2-isopropylbenzoyl)amino]phenyl]-1,2,3,4,8,9,10,11-octahydronaphtho[1,2-b][1,4]diazepine-2,4(3H,5H)-dione;

(Compound B124) 5-[4-[2-chloro-5-(methylthio)benzoylamino]phenyl]-1H-naphtho[1,2-b][1,4]diazepine-2,4(3H,5H)-dione;

(Compound B125) 5-[4-[2-(methylthio)benzoylamino]phenyl]-1H-naphtho[1,2-b][1,4]diazepine-2,4(3H,5H)-dione;

(Compound B126) 5-[4-[3-(methylthio)benzoylamino]phenyl]-1H-naphtho[1,2-b][1,4]diazepine-2,4(3H,5H)-dione;

(Compound B127) 5-[4-[2-ethyl-6-methoxybenzoylamino]phenyl]-1H-naphtho[1,2-b][1,4]diazepine-2,4(3H,5H)-dione;

(Compound B128) 5-[4-(3-methanesulfonylbenzoylamino)phenyl]-1H-naphtho[1,2-b][1,4]diazepine-2,4(3H,5H)-dione;

(Compound B129) 6-ethyl-1-[4-(2-iodobenzoyl)aminophenyl]-1H-1,5-benzodiazepine-2,4(3H,5H)-dione;

(Compound B130) 5-[4-[2-ethyl-6-hydroxybenzoylamino]phenyl]-1H-naphtho[1,2-b][1,4]diazepine-2,4(3H,5H)-dione;

(Compound B131) 5-[4-(3-methanesulfinylbenzoylamino)phenyl]-1H-naphtho[1,2-b][1,4]diazepine-2,4(3H,5H)-dione;

(Compound B132) 5-[4-(2-chloro-5-methanesulfinylbenzoylamino)phenyl]-1H-naphtho[1,2-b][1,4]diazepine-2,4(3H,5H)-dione;

(Compound B133) 5-[4-(2-methanesulfinylbenzoylamino)phenyl]-1H-naphtho[1,2-b][1,4]diazepine-2,4(3H,5H)-dione;

(Compound B134) 5-[4-[[2-(4-morpholinyl)acetyl]amino]phenyl]-1,2,3,4,8,9,10,11-octahydronaphtho[1,2-b][1,4]diazepine-2,4(3H,5H)-dione hydrochloride;

(Compound B135) 5-[4-(2-chloro-6-methoxybenzoylamino)phenyl]-1,3-dihydronaphtho[1,2-e]-1,4-diazepin-2-one;

(Compound B136) 5-[4-[[(3-chloropyridin-2-yl)carbonyl]amino]phenyl]-1H-naphtho[1,2-b][1,4]diazepine-2,4(3H,5H)-dione;

(Compound B137) 5-[4-(2-chloro-6-hydroxybenzoylamino)phenyl]-1,3-dihydronaphtho[1,2-e]-1,4-diazepin-2-one;

(Compound B138) 5-[4-(3-chloro-2-methoxybenzoylamino)phenyl]-1H-naphtho[1,2-b][1,4]diazepine-2,4(3H,5H)-dione;

(Compound B139) 5-[4-[(3-methylpyridin-2-yl)carbonylamino]phenyl]-1H-naphtho[1,2-b][1,4]diazepine-2,4(3H,5H)-dione;

(Compound B140) 5-[4-[[(3-chloropyridin-2-yl)carbonyl]amino]phenyl]-1,2,3,4,8,9,10,11-octahydronaphtho[1,2-b][1,4]diazepine-2,4(3H,5H)-dione;

(Compound B141) 5-[4-(3-chloro-2-hydroxybenzoylamino)phenyl]-1H-naphtho[1,2-b][1,4]diazepine-2,4(3H,5H)-dione;

(Compound B142) 5-[4-[[(3-hydroxypyridin-2-yl)carbonyl]amino]phenyl]-1H-naphtho[1,2-b][1,4]diazepine-2,4(3H,5H)-dione;

(Compound B143) 5-[4-[(3-vinylpyridin-2-yl)carbonylamino]phenyl]-1H-naphtho[1,2-b][1,4]diazepine-2,4(3H,5H)-dione;

(Compound B144) 5-[4-[(3-ethylpyridin-2-yl)carbonylamino]phenyl]-1H-naphtho[1,2-b][1,4]diazepine-2,4(3H,5H)-dione;

(Compound B145)N-[4-(2,4-dioxo-1,2,3,4-tetrahydronaphtho-[1,2-b][1,4]-diazepin-5-yl)phenyl]-2-nitrobenzenesulfonamide;

(Compound B146)N-[4-(2,4-dioxo-1,2,3,4-tetrahydronaphtho[1,2-b][1,4]diazepin-5-yl)phenyl]benzenesulfonamide;

(Compound B147) 3-bromo-N-[4-(2,4-dioxo-1,2,3,4-tetrahydronaphtho[1,2-b][1,4]diazepin-5-yl)phenyl]benzenesulfonamide;

(Compound B148)N-[4-(2,4-dioxo-1,2,3,4-tetrahydronaphtho[1,2-b][1,4]diazepin-5-yl)phenyl]-3-methoxybenzenesulfonamide;

(Compound B149)N-[3-(2-oxo-2,3-dihydro-1H-naphtho[1,2-e][1,4]diazepin-5-yl)phenyl]benzenesulfonamide;

(Compound B150)N-[3-(2,4-dioxo-1,2,3,4-tetrahydronaphtho-[1,2-b][1,4]-diazepin-5-yl)phenyl]-2-nitrobenzenesulfonamide;

(Compound B151)N-[4-(2,4-dioxo-1,2,3,4,8,9,10,11-octahydro-naphtho[1,2-b][1,4]-diazepin-5-yl)phenyl]-2-nitrobenzenesulfonamide;

(Compound B152)N-[4-(2,4-dioxo-1,2,3,4,8,9,10,11-octahydro-naphtho[1,2-b][1,4]-diazepin-5-yl)phenyl]-N-methyl-2-nitrobenzenesulfonamide;

(Compound B153)N-[3-(2,4-dioxo-1,2,3,4-tetrahydronaphtho-[1,2-b][1,4]-diazepin-5-yl)phenyl]-N-methyl-2-nitrobenzenesulfonamide;

(Compound B154) 4-(2,4-dioxo-1,2,3,4,8,9,10,11-octahydronaphtho[1,2-b][1,4]diazepin-5-yl)-N-phenylbenzenesulfonamide;

(Compound B155)N-[3-(2,4-dioxo-1,2,3,4-tetrahydronaphtho[1,2-b]-[1,4]diazepin-5-yl)phenyl]-2-naphthalenesulfonamide;

(Compound B156)N-[3-(2,4-dioxo-1,2,3,4-tetrahydronaphtho[1,2-b]-[1,4]diazepin-5-yl)phenyl]-1-naphthalenesulfonamide;

(Compound B157)N-[4-(2,4-dioxo-1,2,3,4-tetrahydronaphtho[1,2-b][1,4]diazepin-5-yl)phenyl]cyclohexanesulfonamide;

(Compound B158)N-[4-(2,4-dioxo-1,2,3,4-tetrahydronaphtho[1,2-b][1,4]diazepin-5-yl)phenyl]-3-pyridinesulfonamide hydrochloride;

(Compound B159)N-[4-(2,4-dioxo-1,2,3,4-tetrahydronaphtho[1,2-b][1,4]diazepin-5-yl)phenyl]-4-isopropylbenzenesulfonamide;

(Compound B160)N-[4-(2,4-dioxo-1,2,3,4-tetrahydronaphtho[1,2-b][1,4]diazepin-5-yl)phenyl]phenylmethanesulfonamide;

(Compound B161)N-[4-(2,4-dioxo-1,2,3,4-tetrahydronaphtho[1,2-b][1,4]diazepin-5-yl)phenyl]-2-thiophene-sulfonamide;

(Compound B162)N-[4-(2,4-dioxo-1,2,3,4-tetrahydronaphtho[1,2-b][1,4]diazepin-5-yl)phenyl]-2-naphthalenesulfonamide;

(Compound B163) 4-(2,4-dioxo-1,2,3,4,8,9,10,11-octahydronaphtho-[1,2-b][1,4]diazepin-5-yl)phenyl 3-bromobenzene-sulfonate;

(Compound B164)N-benzyl-N-[4-(1-benzyl-2,4-dioxo-1,2,3,4-tetrahydronaphtho[1,2-b][1,4]diazepin-5-yl)phenyl]-2-nitrobenzenesulfonamide;

(Compound B165)N-benzyl-N-[4-(2,4-dioxo-1,2,3,4-tetrahydronaphtho[1,2-b][1,4]diazepin-5-yl)phenyl]-2-nitrobenzenesulfonamide;

(Compound B166) 3-bromo-N-[4-(2,4-dioxo-1,2,3,4-tetrahydronaphtho[1,2-b][1,4]diazepin-5-yl)phenyl]-N-methylbenzenesulfonamide;

(Compound B167)N-[4-(2,4-dioxo-1,2,3,4-tetrahydronaphtho-[1,2-b][1,4]-diazepin-5-yl)phenyl]-N-methyl-2-nitrobenzenesulfonamide;

(Compound B168)N-[4-(2,4-dioxo-1,2,3,4-tetrahydronaphtho-[1,2-b][1,4]-diazepin-5-yl)phenyl]-N-(2-hydroxyethyl)-2-nitrobenzenesulfonamide;

(Compound B169)N-[4-(7-chloro-2,4-dioxo-2,3,4,5-tetrahydro-1H-benzo[b][1,4]diazepin-1-yl)phenyl]benzenesulfonamide;

(Compound B170)N-[4-(7-bromo-2,4-dioxo-2,3,4,5-tetrahydro-1H-benzo[b][1,4]diazepin-1-yl)phenyl]benzenesulfonamide;

(Compound B171)N-[4-[(2,4-dioxo-7-(trifluoromethyl)-2,3,4,5-tetrahydro-1H-benzo[b][1,4]diazepin-1-yl)]phenyl]benzenesulfonamide;

(Compound B172)N-[4-(2,4-dioxo-2,3,4,5-tetrahydro-1H-benzo[b][1,4]diazepin-1-yl)phenyl]benzenesulfonamide;

(Compound B173) 1-(2-chlorophenyl)-N-[4-(2,4-dioxo-1,2,3,4-tetrahydronaphtho[1,2-b][1,4]diazepin-5-yl)phenyl]methanesulfonamide;

(Compound B174) 1-(3-bromophenyl)-N-[4-(2,4-dioxo-1,2,3,4-tetrahydronaphtho[1,2-b][1,4]diazepin-5-yl)phenyl]methanesulfonamide;

(Compound B175)N-[4-(2,4-dioxo-1,2,3,4-tetrahydronaphtho-[1,2-b][1,4]-diazepin-5-yl)phenyl]-2-trifluoromethylbenzenesulfonamide;

(Compound B176)N-[4-(7-bromo-6-methyl-2,4-dioxo-2,3,4,5-tetrahydro-1H-benzo[b][1,4]diazepin-1-yl)phenyl]benzenesulfonamide;

(Compound B177) 1-(2-chlorophenyl)-N-[4-(2,4-dioxo-1,2,3,4,8,9,10,11-octahydronaphtho[1,2-b][1,4]diazepin-5-yl)phenyl]methanesulfonamide;

(Compound B178) 3-bromo-N-[4-(2,4-dioxo-1,2,3,4,8,9,10,11-octahydronaphtho[1,2-b][1,4]diazepin-5-yl)phenyl]benzenesulfonamide;

(Compound B179)N-[4-(2,4-dioxo-1,2,3,4,8,9,10,11-octahydronaphtho[1,2-b][1,4]diazepin-5-yl)phenyl]-3-methoxybenzenesulfonamide;

(Compound B180) 1-(2-bromophenyl)-N-[4-(2,4-dioxo-1,2,3,4-tetrahydronaphtho[1,2-b][1,4]diazepin-5-yl)phenyl]methanesulfonamide;

(Compound B181)N-[4-(2,4-dioxo-1,2,3,4-tetrahydronaphtho[1,2-b][1,4]diazepin-5-yl)phenyl]-1-(2-methylphenyl)methanesulfonamide;

(Compound B182)N-[4-(2,4-dioxo-1,2,3,4-tetrahydronaphtho[1,2-b][1,4]diazepin-5-yl)phenyl]-1-(2-nitrophenyl)methanesulfonamide;

(Compound B183)N-[4-(2,4-dioxo-1,2,3,4-tetrahydronaphtho[1,2-b][1,4]diazepin-5-yl)phenyl]-2-phenylethanesulfonamide;

(Compound B184) 1-(2,3-dichlorophenyl)-N-[4-(2,4-dioxo-1,2,3,4,8,9,10,11-octahydronaphtho[1,2-b][1,4]diazepin-5-yl)phenyl]methanesulfonamide;

(Compound B185) 1-(2-chlorophenyl)-N-[4-(2,4-dioxo-7-methoxy-1H-benzo[1,2-b][1,4]diazepin-1-yl)phenyl]methanesulfonamide;

(Compound B186) 1-(2-chlorophenyl)-N-[4-(2,4-dioxo-7-hydroxy-1H-benzo[1,2-b][1,4]diazepin-1-yl)phenyl]methanesulfonamide;

(Compound B187) 1-(4-chlorophenyl)-N-[4-(2,4-dioxo-1,2,3,4-tetrahydronaphtho[1,2-b][1,4]diazepin-5-yl)phenyl]methanesulfonamide;

(Compound B188) 1-(2-chlorophenyl)-N-[4-(2,4-dioxo-1,2,3,4-tetrahydronaphtho[1,2-b][1,4]diazepin-5-yl)benzyl]methanesulfonamide;

(Compound B189) 1-(2-chlorophenyl)-N-[4-(2,4-dioxo-1,2,3,4-tetrahydronaphtho[1,2-b][1,4]diazepin-5-yl)-2-methoxyphenyl]methanesulfonamide;

(Compound B190) 1-(2-chlorophenyl)-N-[4-(2,4-dioxo-1,2,3,4-tetrahydronaphtho[1,2-b][1,4]diazepin-5-yl)-2-hydroxyphenyl]methanesulfonamide;

(Compound B191) 1-(2,6-dichlorophenyl)-N-[4-(2,4-dioxo-1,2,3,4,8,9,10,11-octahydronaphtho[1,2-b][1,4]diazepin-5-yl)phenyl]methanesulfonamide;

(Compound B192) 1-(2-chlorophenyl)-N-[4-(2,4-dioxo-6-methyl-1H-benzo[1,2-b][1,4]diazepin-1-yl)phenyl]methanesulfonamide;

(Compound B193) 1-(2-chlorophenyl)-N-[3-(2,4-dioxy-1,2,3,4-tetrahydronaphtho[1,2-b][1,4]diazepin-5-yl)propyl]methanesulfonamide;

(Compound B194) 1-(2-chlorophenyl)-N-[2-(2,4-dioxo-1,2,3,4-tetrahydronaphtho[1,2-b][1,4]diazepin-5-yl)ethyl]methanesulfonamide;

(Compound B195)N-[4-(2,4-dioxo-1,2,3,4,8,9,10,11-octahydronaphtho[1,2-b][1,4]diazepin-5-yl)phenyl]-1-(2-iodophenyl)methanesulfonamide;

(Compound B196) 1-(2-chlorophenyl)-N-[4-(2,4-dioxo-1,2,3,4,8,9,10,11-octahydronaphtho[1,2-b][1,4]diazepin-5-yl)phenyl]-N-methylmethanesulfonamide;

(Compound B197) 1-(2-chlorophenyl)-N-[4-(2-oxo-2,3-dihydro-1H-naphtho[1,2-e][1,4]diazepin-5-yl)phenyl]methanesulfonamide;

(Compound B198) 1-[2-(trifluoromethyl)phenyl]-N-[4-(2,4-dioxo-1,2,3,4-tetrahydronaphtho[1,2-b][1,4]diazepin-5-yl)phenyl]phenyl-N-methylmethanesulfonamide;

(Compound B199) 1-(2-ethylphenyl)-N-[4-(2,4-dioxo-1,2,3,4-tetrahydronaphtho[1,2-b][1,4]diazepin-5-yl)phenyl]phenyl-N-methylmethanesulfonamide;

(Compound B200) 1-(2,3-dimethylphenyl)-N-[4-(2,4-dioxo-1,2,3,4-tetrahydronaphtho[1,2-b][1,4]diazepin-5-yl)phenyl]phenyl-N-methylmethanesulfonamide;

(Compound B201) 2-(2-chlorophenyl)-N-[4-(2,4-dioxo-1,2,3,4-tetrahydronaphtho[1,2-b][1,4]diazepin-5-yl)phenyl]phenyl-N-methylethanesulfonamide;

(Compound B202) 1-(2-nitrophenyl)-N-[4-(2,4-dioxo-1,2,3,4-tetrahydronaphtho[1,2-b][1,4]diazepin-5-yl)phenyl]phenyl-N-methylmethanesulfonamide;

(Compound B203) 1-(2-aminophenyl)-N-[4-(2,4-dioxo-1,2,3,4-tetrahydronaphtho[1,2-b][1,4]diazepin-5-yl)phenyl]phenyl-N-methylmethanesulfonamide;

(Compound B204) 1-(2-dimethylaminophenyl)-N-[4-(2,4-dioxo-1,2,3,4-tetrahydronaphtho[1,2-b][1,4]diazepin-5-yl)phenyl]phenyl-N-methylmethanesulfonamide;

(Compound B205) 5-[4-[(pyridin-4-yl)carbonylamino]phenyl]-1H-naphtho[1,2-b][1,4]diazepine-2,4(3H,5H)-dione hydrochloride;

(Compound B206) 5-[4-[2-[(pyridin-3-yl)oxy]acetylamino]phenyl]-1H-naphtho[1,2-b][1,4]diazepine-2,4(3H,5H)-dione hydrochloride;

(Compound B207) 5-[4-[(pyridin-3-yl)carbonylamino]phenyl]-1H-naphtho[1,2-b][1,4]diazepine-2,4(3H,5H)-dione hydrochloride;

(Compound B208) 5-[4-[(2-methylpyridin-3-yl)carbonylamino]phenyl]-1H-naphtho[1,2-b][1,4]diazepine-2,4(3H,5H)-dione hydrochloride;

(Compound B209) 5-[4-[(2-chloropyridin-3-yl)carbonylamino]phenyl]-1H-naphtho[1,2-b][1,4]diazepine-2,4(3H,5H)-dione;

(Compound B210) 5-[4-[2-[(pyridin-2-yl)oxy]acetylamino]phenyl]-1H-naphtho[1,2-b][1,4]diazepine-2,4(3H,5H)-dione;

(Compound B211) 5-[4-[[4-(trifluoromethyl)pyridin-3-yl]carbonylamino]phenyl]-1H-naphtho[1,2-b][1,4]diazepine-2,4(3H,5H)-dione;

(Compound B212) 5-[4-[(2-chloropyridin-3-yl)carbonylamino]phenyl]-1H-[1,4]diazepino[2,3-f]isoquinoline-2,4(3H,5H)-dione;

(Compound B213) 5-[4-[(2-chloropyridin-3-yl)carbonylamino]phenyl]-8,9,10,11-tetrahydro-1H-[1,4]diazepino[2,3-f]isoquinoline-2,4(3H,5H)-dione; and (Compound B214) 5-[4-[(2-isopropylbenzoyl)amino]phenyl]-1H-naphtho[1,2-b][1,4]diazepine-2,4(3H,5H)-dione A more preferable compound or a pharmaceutically acceptable salt thereof as the active ingredient of the pharmaceutical composition of the present invention is comprised in the compounds represented by the general formulas (A) to (BII) or a pharmaceutically acceptable salt thereof. Specific examples of the more preferable compound or a pharmaceutically acceptable salt thereof can comprise 5-[3-(1H-tetrazol-5-yl)phenyl]-1H-naphtho[1,2-b][1,4]diazepine-2,4(3H,5H)-dione; a 5-[3-(1H-tetrazol-5-yl)phenyl]-1H-naphtho[1,2-b][1,4]diazepine-2,4(3H,5H)-dione sodium salt; a 5-[3-(1H-tetrazol-5-yl)phenyl]-1H-naphtho[1,2-b][1,4]diazepine-2,4(3H,5H)-dione potassium salt; 5-[3-(5-thioxo-4H-[1,2,4]oxadiazol-3-yl)phenyl]-1H-naphtho[1,2-b][1,4]diazepine-2,4(3H,5H)-dione; a 5-[3-(5-thioxo-4H-[1,2,4]oxadiazol-3-yl)phenyl]-1H-naphtho[1,2-b][1,4]diazepine-2,4(3H,5H)-dione sodium salt; 5-[4-fluoro-3-(1H-tetrazol-5-yl)phenyl]-1H-naphtho[1,2-b][1,4]diazepine-2,4(3H,5H)-dione; a 5-[4-fluoro-3-(1H-tetrazol-5-yl)phenyl]-1H-naphtho[1,2-b][1,4]diazepine-2,4(3H,5H)-dione sodium salt; 5-[4-[2-(trifluoromethyl)benzoyl]aminophenyl]-1H-naphtho[1,2-b][1,4]diazepine-2,4(3H,5H)-dione; 5-[4-[(2-chlorophenylacetyl)amino]phenyl]-1H-naphtho[1,2-b][1,4]diazepine-2,4(3H,5H)-dione; 1-[4-(2,4-dioxo-1,2,3,4-tetrahydronaphtho[1,2-b][1,4]diazepin-5-yl)phenyl]-3-phenylurea; 5-[4-(2-iodobenzoylamino)phenyl]-1H-naphtho[1,2-b][1,4]diazepine-2,4(3H,5H)-dione; 5-[4-

[(2-ethylbenzoyl)amino]phenyl]-1H-naphtho[1,2-b][1,4]diazepine-2,4(3H,5H)-dione; 5-[4-(2-tert-butylbenzoylamino)phenyl]-1H-naphtho[1,2-b][1,4]diazepine-2,4(3H,5H)-dione; 5-[4-(2-iodobenzoyl)aminophenyl]-1,2,3,4,8,9,10,11-octahydronaphtho[1,2-b][1,4]diazepine-2,4(3H,5H)-dione; 5-[4-(6-chloro-2-hydroxybenzoylamino)phenyl]-1H-naphtho[1,2-b][1,4]diazepine-2,4(3H,5H)-dione; N-[4-(2,4-dioxo-1,2,3,4-tetrahydronaphtho[1,2-b][1,4]diazepin-5-yl)phenyl]benzenesulfonamide; 1-(2-chlorophenyl)-N-[4-(2,4-dioxo-1,2,3,4-tetrahydronaphtho[1,2-b][1,4]diazepin-5-yl)phenyl]methanesulfonamide; 1-(2-chlorophenyl)-N-[4-(2,4-dioxo-1,2,3,4,8,9,10,11-octahydronaphtho[1,2-b][1,4]diazepin-5-yl)phenyl]methanesulfonamide; 1-(2-bromophenyl)-N-[4-(2,4-dioxo-1,2,3,4-tetrahydronaphtho[1,2-b][1,4]diazepin-5-yl)phenyl]methanesulfonamide; N-[4-(2,4-dioxo-1,2,3,4-tetrahydronaphtho[1,2-b][1,4]diazepin-5-yl)phenyl]-1-(2-methylphenyl)methanesulfonamide; N-[4-(2,4-dioxo-1,2,3,4-tetrahydronaphtho[1,2-b][1,4]diazepin-5-yl)phenyl]-2-phenylethanesulfonamide; 1-(2-chlorophenyl)-N-[4-(2,4-dioxo-1,2,3,4,8,9,10,11-octahydronaphtho[1,2-b][1,4]diazepin-5-yl)phenyl]-N-methylmethanesulfonamide; 1-(2-chlorophenyl)-N-[4-(2-oxo-2,3-dihydro-1H-naphtho[1,2-e][1,4]diazepin-5-yl)phenyl]methanesulfonamide; 5-[4-[(2-methylpyridin-3-yl)carbonylamino]phenyl]-1H-naphtho[1,2-b][1,4]diazepine-2,4(3H,5H)-dione hydrochloride; 5-[4-[(2-chloropyridin-3-yl)carbonylamino]phenyl]-1H-naphtho[1,2-b][1,4]diazepine-2,4(3H,5H)-dione; 5-[4-[2-[(pyridin-2-yl)oxy]acetylamino]phenyl]-1H-naphtho[1,2-b][1,4]diazepine-2,4(3H,5H)-dione; and 5-[4-[(2-isopropylbenzoyl)amino]phenyl]-1H-naphtho[1,2-b][1,4]diazepine-2,4(3H,5H)-dione. Note that the active ingredient of the pharmaceutical composition of the present invention is not limited to the above specific compounds or a pharmaceutically acceptable salt thereof.

An even more preferable compound or a pharmaceutically acceptable salt thereof as the active ingredient of the pharmaceutical composition of the present invention is comprised in the compounds represented by the general formulas (A) to (BII) or a pharmaceutically acceptable salt thereof. Specific examples of the even more preferable compound or a pharmaceutically acceptable salt thereof can comprise 5-[3-(1H-tetrazol-5-yl)phenyl]-1H-naphtho[1,2-b][1,4]diazepine-2,4(3H,5H)-dione; a 5-[3-(1H-tetrazol-5-yl)phenyl]-1H-naphtho[1,2-b][1,4]diazepine-2,4(3H,5H)-dione sodium salt; 5-[3-(5-thioxo-4H-[1,2,4]oxadiazol-3-yl)phenyl]-1H-naphtho[1,2-b][1,4]diazepine-2,4(3H,5H)-dione; a 5-[3-(5-thioxo-4H-[1,2,4]oxadiazol-3-yl)phenyl]-1H-naphtho[1,2-b][1,4]diazepine-2,4(3H,5H)-dione sodium salt; 5-[4-[2-(trifluoromethyl)benzoyl]aminophenyl]-1H-naphtho[1,2-b][1,4]diazepine-2,4(3H,5H)-dione; 5-[4-(2-iodobenzoylamino)phenyl]-1H-naphtho[1,2-b][1,4]diazepine-2,4(3H,5H)-dione; and 5-[4-(6-chloro-2-hydroxybenzoylamino)phenyl]-1H-naphtho[1,2-b][1,4]diazepine-2,4(3H,5H)-dione. Note that the active ingredient of the pharmaceutical composition of the present invention is not limited to the above specific compounds or a pharmaceutically acceptable salt thereof.

Stereoisomers of the compounds represented by the general formulas (A) to (BII), such as a cis-trans isomer, an optically active form, or a racemic form thereof, may exist as well, all of which are comprised in the present invention.

Tautomers of the compounds represented by the general formulas (A) to (BII) may exist as well, and the tautomers show the same activities as those of the compounds and are comprised in the present invention.

Furthermore, the compounds represented by the general formulas (A) to (BII) may have one or two or more asymmetric carbons depending on the type of substituent, and any optical isomer or any mixture or a racemic form of optical isomers, which is based on the asymmetric carbon, or a diastereoisomer or any mixture of diastereoisomers, which is based on two or more asymmetric carbons, may also be used as the active ingredient of the pharmaceutical composition of the present invention. In a case where the compounds represented by the general formulas (AI) to (BII) have a double bond or a cyclic structure, a geometric isomer may exist, and, in addition to a pure form of the geometric isomer, a mixture of geometric isomers, which are contained in the mixture at any ratio, may also be used as the active ingredient of the pharmaceutical composition of the present invention.

In addition to the compounds represented by the general formulas (A) to (BII), any solvate of a free form of the compound or a salt form of the compound may also be used as active ingredient of the pharmaceutical composition of the present invention. The solvate also comprises a hydrate.

In the present specification, unless otherwise specified, the compounds represented by general formulas (A) to (BII) can comprise the stereoisomer of the compound, such as the cis-trans isomer, the optically active form, or the racemic form thereof; the tautomer of the compound; any optical isomer or racemic form of the compound, which is based on an asymmetric carbon; and the diastereoisomer of the compound and a mixture thereof, which is based on two or more asymmetric carbons.

In addition to the compounds represented by the general formulas (A) to (BII), acid addition salts or base addition salts of these compounds may also be used as the active ingredient of the medicament of the present invention. As the acid addition salt, for example, a mineral acid salt such as hydrochloride, sulfate, and nitrate; an organic acid salt such as methanesulfonate, p-toluenesulfonate, oxalate, and malate; and the like can be used, however, the acid addition salt is not limited thereto. Examples of the base addition salt can comprise a metal salt such as a lithium salt, a sodium salt, a potassium salt, a magnesium salt, and a calcium salt; an ammonium salt; an organic amine salt such as a triethylamine salt and an ethanolamine salt; and the like, however, the base addition salt is not limited thereto. Among these salts, a pharmaceutically acceptable salt is preferably used as the active ingredient of the pharmaceutical composition of the present invention.

The pharmaceutical composition of the present invention can be used in preventing, suppressing, or treating a symptom associated with an allergic reaction. Furthermore, the pharmaceutical composition of the present invention can be used in preventing, suppressing, or treating an allergic disease. Preferably, the pharmaceutical composition of the present invention can be used in preventing, suppressing, or treating a symptom associated with a type I allergic reaction. More preferably, the pharmaceutical composition of the present invention can be used in preventing or treating an anaphylactic shock, allergic rhinitis, bronchial asthma, or allergic dermatitis, and can be used in suppressing an anaphylactic shock or preventing or treating pollinosis, urticaria, or atopic dermatitis.

Furthermore, the pharmaceutical composition of the present invention can be used for preventing, suppressing, or reducing inflammation in a symptom associated with an allergic reaction. Moreover, the pharmaceutical composition of the present invention can be used for suppressing release of secretory granules within mast cells to the outside of the cells in a symptom associated with an allergic reaction.

As another aspect, the pharmaceutical composition of the present invention can be used for the following use.

The pharmaceutical composition of the present invention can be used for preventing, suppressing, or treating the symptom associated with an allergic reaction which is accompanied by inflammation.

The pharmaceutical composition of the present invention can be used in preventing, suppressing, or treating the symptom associated with an allergic reaction which is accompanied by release of secretory granules within mast cells to the outside of the cells.

Any of the symptoms associated with an allergic reaction is a target for the application of the pharmaceutical composition of the present invention. The target for the application of the pharmaceutical composition of the present invention is not limited thereto.

The pharmaceutical composition of the present invention can be administered orally or parenterally. The pharmaceutical composition of the present invention can be produced in a suitable dosage form such as a tablet, granules, a powder, a capsule, a suspension, an inhalation, a dry powder inhaler, an inhalation liquid, an aerosol inhaler, an ointment, a gel, a cream, a poultice, a patch, a liniment, a tape, a plaster, an injection, and a suppository, according to a general method in the technical field of preparations. In one embodiment, the "pharmaceutical composition" contains the active ingredient and a pharmaceutically acceptable additive.

These pharmaceutical preparations can be manufactured using a general technique. For example, in a case of the tablet, a general pharmaceutically acceptable additive such as a diluent, a disintegrant, a binder, a lubricant, and a coloring agent can be used. Examples of the diluent can comprise lactose, D-mannitol, microcrystalline cellulose, glucose, and the like. Examples of the disintegrant can comprise starch, carboxymethylcellulose calcium (CMC-Ca), and the like. Examples of the lubricant can comprise magnesium stearate, talc, and the like. Examples of the binder can comprise hydroxypropyl cellulose (HPC), gelatin, polyvinyl pyrrolidone (PVP), and the like.

A pharmaceutically acceptable additive such as a solvent, a stabilizer, a solubilizing agent, a suspension, an emulsifier, an analgesic agent, a buffer, and a preservative is used in preparation of the injection. The pharmaceutically acceptable additive and a method of preparing a pharmaceutical preparation can be suitably selected by those skilled in the art.

In other words, the pharmaceutical composition of the present invention can be provided as a pharmaceutical composition comprising the active ingredient and the pharmaceutically acceptable additive.

Types of the inhalation for the parenteral administration comprise an aerosol, a dry powder for inhalation, a liquid for inhalation (for example, a solution for inhalation, a suspension for inhalation, and the like), and a capsule inhalation, and the liquid for inhalation may be in a form that is used by being dissolved or suspended in water or another suitable medium at the time of use. The inhalation can be applied using a suitable inhalation container. For example, when administering the liquid for inhalation, a sprayer (an atomizer or a nebulizer) or the like can be used, and when administering the dry powder for inhalation, an inhaler for a dry powder drug or the like can be used.

The inhalation can be manufactured according to a known method. For example, the inhalation is manufactured by obtaining a dry powder or a liquid of the compounds represented by the general formulas (A) to (BII), blending the dry powder or the liquid of the compounds into an inhalation propellant or a carrier, and filling a suitable inhalation container with the blended product. In a case of powderizing the compounds represented by the general formulas (A) to (BII), the powderization is performed according to a general method. For example, a dry powder is prepared by obtaining a fine powder of the compounds and lactose, starch, magnesium stearate, or the like, thereby obtaining a homogeneous mixture, or by granulating the compounds. In addition, in a case where the compounds represented by the general formulas (A) to (BII) are liquefied, for example, the compounds may be dissolved in a liquid carrier such as water, physiological saline, and an organic solvent. As the propellant, a conventionally known propellant, for example, alternative chlorofluorocarbon, a liquefied gas propellant (for example, fluorohydrocarbon, liquefied petroleum, diethyl ether, dimethyl ether, and the like), a compressed gas (for example, a soluble gas (for example, carbon dioxide gas, nitrous oxide gas, and the like), an insoluble gas (for example, nitrogen gas and the like), and the like are used.

A pharmaceutically acceptable additive may be suitably blended into the inhalation as necessary. The additive may be any additive that is generally used. For example, a solid diluent (for example, sucrose, lactose, glucose, mannitol, sorbitol, maltose, cellulose, and the like), a liquid diluent (for example, propylene glycol and the like), a binder (starch, dextrin, methylcellulose, hydroxypropylcellulose, polyvinylpyrrolidone, polyethylene glycol, sucrose, and the like), a lubricant (for example, magnesium stearate, light anhydrous silicic acid, talc, sodium lauryl sulfate, and the like), a corrigent (for example, citric acid, menthol, glycyrrhizin ammonium salt, glycine, an orange powder, and the like), a preservative (for example, sodium benzoate, sodium bisulfite, methylparaben, propylparaben, and the like), a stabilizer (for example, citric acid, sodium citrate, and the like), a suspending agent or an emulsifier (for example, methyl cellulose, polyvinyl pyrrolidone, polyvinyl alcohol, lecithin, sorbitan trioleate, and the like), a dispersing agent (for example, a surfactant and the like), a solvent (for example, water and the like), a tonicity agent (for example, sodium chloride, concentrated glycerin, and the like), a pH regulator (for example, hydrochloric acid, sulfuric acid, and the like), a solubilizer (for example, ethanol and the like), an antiseptic agent (benzalkonium chloride, paraben, and the like), a colorant, a buffer agent (sodium phosphate, sodium acetate, and the like), a thickening agent (carboxyvinyl polymer and the like), an absorption promoter, and the like are used. The liquid for inhalation is prepared by, for example, suitably selecting the antiseptic agent, the colorant, the buffer agent, the tonicity agent, the thickening agent, the absorption promoter, or the like as necessary. Furthermore, the dry powder for inhalation is prepared by, for example, suitably selecting the lubricant, the binder, the diluent, the colorant, the antiseptic agent, the absorption promoter (bile salt, chitosan, and the like), or the like as necessary.

Furthermore, in order to prepare the compounds represented by the general formulas (A) to (BII) in a sustained release form, the inhalation may contain a biodegradable polymer. Examples of the biodegradable polymer can comprise a fatty acid ester polymer or a copolymer thereof, polyacrylic acid esters, polyhydroxybutyric acids, polyalkylene oxalates, polyorthoester, polycarbonate, and polyamino acids, and one polymer can be used alone, or two or more thereof can be used in combination. Furthermore, a phospholipid such as egg yolk lecithin, chitosan, or the like may also be used. Examples of the fatty acid ester polymer or a copolymer thereof can comprise polylactic acid, polyglycolic acid, polycitric acid, polymalic acid, and a lactic acid-glycolic acid copolymer, and one polymer or copolymer can be used alone, or two or more thereof can be used in combination. In addition, one of poly-α-cyanoacrylic acid ester, poly-β-hydroxybutyric acid, polytrimethylene oxide, polyorthoester, polyorthocarbonate, polyethylenecarbonate, poly-γ-benzyl-L-glutamic acid, and poly-L-alanine can be used alone, or two or more thereof can be used in combination. The fatty acid ester polymer or a copolymer thereof is preferably polylactic acid, polyglycolic acid, or a lactic acid-glycolic acid copolymer, and is more preferably a lactic acid-glycolic acid copolymer. Furthermore, a microsphere or a nanosphere may be prepared by encapsulating a drug using the biodegradable polymer such as a lactic acid-glycolic acid copolymer.

An ointment is produced by known or generally used formulation. For example, the ointment is produced and prepared by triturating or melting one or more active substances in a base. The ointment base is selected from known or generally used bases. For example, a single base or a mixture of two or more bases selected from a higher fatty acid or a higher fatty acid ester (adipic acid, myristic acid, palmitic acid, stearic acid, oleic acid, adipic acid ester, myristic acid ester, palmitic acid ester, stearic acid ester, oleic acid ester, or the like), waxes (beeswax, spermaceti, ceresin, or the like), a surfactant (polyoxyethylene alkyl ether phosphoric acid ester or the like), a higher alcohol (cetanol, stearyl alcohol, cetostearyl alcohol, or the like), silicone oil (dimethylpolysiloxane or the like), hydrocarbons (hydrophilic petrolatum, white petrolatum, purified lanolin, liquid paraffin, or the like), glycols (ethylene glycol, diethylene glycol, propylene glycol, polyethylene glycol, macrogol, or the like), plant oil (castor oil, olive oil, sesame oil, turpentine oil, or the like), animal oil (mink oil, egg-yolk oil, squalane, squalene, or the like), water, an absorption promoter, and an irritation preventing agent is used. The ointment may further contain a moisturizing agent, a preservative, a stabilizing agent, an antioxidant, a fragrance, or the like.

A gel is produced by known or generally used formulation. For example, the gel is produced and prepared by melting one or more active substances in a base. The gel base is selected from known or generally used bases. For example, a single base or a mixture of two or more bases selected from a lower alcohol (ethanol, isopropyl alcohol, or the like), a gelling agent (carboxymethyl cellulose, hydroxyethyl cellulose, hydroxypropyl cellulose, ethyl cellulose, or the like), a neutralizing agent (triethanolamine, diisopropanolamine, or the like), a surfactant (polyethylene glycol monostearate or the like), gums, water, an absorption promoter, and an irritation preventing agent is used. The liniment may further contain a preservative, an antioxidant, a fragrance, or the like.

A cream is produced by known or generally used formulation. For example, the cream is produced and prepared by melting or emulsifying one or more active substances in a base. The cream base is selected from known or generally used bases. For example, a single base or a mixture of two or more bases selected from a higher fatty acid ester, a lower alcohol, hydrocarbons, polyhydric alcohol (propylene glycol, 1,3-butylene glycol, or the like), a higher alcohol (2-hexyldecanol, cetanol, or the like), an emulsifying agent (polyoxyethylene alkyl ethers, fatty acid esters, or the like), water, an absorption promoter, and an irritation preventing agent is used. The liniment may further contain a preservative, an antioxidant, a fragrance, or the like.

A poultice is produced by known or generally used formulation. For example, the poultice is produced by melting one or more active substances in a base, forming a kneaded product, and spreading and coating the kneaded product onto a support. The poultice base is selected from known or generally used bases. For example, a single base or a mixture of two or more bases selected from a thickening agent (polyacrylic acid, polyvinylpyrrolidone, gum arabic, starch, gelatin, methylcellulose, or the like), a wetting agent (urea, glycerin, propylene glycol, or the like), a filler (kaolin, zinc oxide, talc, calcium, magnesium, or the like), water, a solubilizing agent, a tackifier, and an irritation preventing agent is used. The liniment may further contain a preservative, an antioxidant, a fragrance, or the like.

A patch is produced by known or generally used formulation. For example, the patch is produced by melting one or more active substances in a base and spreading and coating the base containing the active substances onto a support. The base for the patch is selected from known or generally used bases. For example, a single base or a mixture of two or more bases selected from a polymer base, a fat, a higher fatty acid, a tackifier, and an irritation preventing agent is used. The liniment may further contain a preservative, an antioxidant, a fragrance, or the like.

A liniment is produced by known or generally used formulation. For example, the liniment is produced and prepared by dissolving, suspending, or emulsifying one or more active substances in one or two or more selected from water, an alcohol (ethanol, polyethylene glycol, or the like), a higher fatty acid, glycerin, a soap, an emulsifying agent, a suspending agent, and the like. The liniment may further contain a preservative, an antioxidant, a fragrance, or the like.

The dose of the pharmaceutical composition of the present invention is not particularly limited, and generally, to an adult, approximately 0.01 μg to 100 mg and preferably 0.3 μg to 10 mg can be administered per day as an active ingredient amount in a case of administration by an inhalation, a dry powder inhaler, an inhalation liquid, or an aerosol inhaler, approximately 0.01 mg to 1,000 mg can be administered per day as an active ingredient amount in a case of administration by an ointment, a gel, a cream, a poultice, a patch, a liniment, a tape, or a plaster, approximately 0.01 mg to 100 mg can be administered per day as an active ingredient amount in a case of administration by an injection, and approximately 0.01 mg to 2,000 mg can be administered per day in a case of oral administration. Note that the dose is not limited to the above doses and is suitably determined in accordance with the administration method, the age, body weight, sex, and symptom of the administration subject, and sensitivity to a drug. The dose may be adjusted according to the improvement of the symptom and can be increased or decreased according to the age, the symptom, and the like.

The pharmaceutical composition of the present invention can be used in combination with another drug that is useful in treating or preventing various symptoms associated with an allergic reaction. Individual components in such combination can be administered in divided preparations or in a single preparation separately at different times or at the same time, during the period of the treatment or prevention. Therefore, it should be understood that the present invention includes both administration at the same time or administrations at different times, and the administration in the present invention should be understood in such a way. The range of the combination of the pharmaceutical composition of the present invention with another drug that is useful in treating or preventing the various symptoms associated with an allergic reaction includes, in principle, a combination with a certain pharmaceutical preparation that is useful in treating or preventing the various symptoms associated with an allergic reaction.

Various forms can be selected for each preparation in the combined preparation according to the present invention, and each preparation can be produced in the same manner as the above-described preparations. Furthermore, a drug combination which includes the pharmaceutical composition of the present invention and another drug for treating or preventing various symptoms associated with an allergic reaction can also be easily produced by those skilled in the art according to a conventional method or a conventional art.

The combination includes not only a combination of the pharmaceutical composition of the present invention with one other active substance, but also a combination of the pharmaceutical composition of the present invention with two or more other active substances. There are many examples of the combination of the pharmaceutical composition of the present invention with one or two or more active substances selected from the drugs for treating or preventing the various symptoms associated with an allergic reaction.

Examples of the drug that is combined with the pharmaceutical composition of the present invention include a steroid, a β2 agonist, muscarinic receptor antagonist, an antihistamine, an antiallergic drug, a bronchodilator, a leukotriene synthesis inhibitor, prostaglandins, a leukotriene receptor antagonist, an antipruritic agent, and other antitussive drugs and expectorants. Among these drugs, a combination with an antihistamine or an antiallergic drug is preferred. It is also possible to combine the pharmaceutical composition of the present invention with a Chinese herbal medicine.

Examples of the steroid include a topical agent such as clobetasol propionate, diflorasone diacetate, fluocinonide, mometasone furoate, betamethasone dipropionate, betamethasone butyrate propionate, betamethasone valerate, difluprednate, pudesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone dipropionate, triamcinolone acetonide, flumethasone pivalate, alclometasone dipropionate, clobetasone butyrate, prednisolone, peclomethasone dipropionate, or fludroxycortide; an orally administered drug or an injection such as cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone diacetate, triamcinolone acetonide, dexamethasone, dexamethasone acetate, dexamethasone sodium phosphate, dexamethasone palmitate, paramethasone acetate, or betamethasone; and an inhalation such as beclomethasone dipropionate, fluticasone propionate, budesonide, flunisolide, triamcinolone, ST-126P, ciclesonide, dexamethasone palomitionate, mometasone furancarbonate, prasterone sulfonate, deflazacort, methylprednisolone suleptanate, or methylprednisolone sodium succinate.

Examples of the β2 agonist include formoterol, salmeterol, carmoterol, indacaterol, vilanterol, arformoterol, bambuterol, isoproterenol, milveterol, clenbuterol, olodaterol, fenoterol, salbutamol, levalbuterol, procaterol, terbutaline, pirbuterol, procaterol, metaproterenol, bitolterol, ritodrine, and albuterol.

Examples of the muscarinic receptor antagonist include tiotropium, ipratropium, flutropium, oxitropium, aclidinium, darotropium, glycopyrrolate, and umeclidinium.

Examples of the antihistamine include diphenhydramine, diphenylpyraline hydrochloride, diphenylpyraline teoclate, clemastine fumarate, dimenhydrinate, dl-chlorpheniramine maleate, d-chlorpheniramine maleate, triprolidine hydrochloride, promethazine hydrochloride, alimemazine tartrate, isothipendyl hydrochloride, homochlorcyclizine hydrochloride, hydroxyzine, cyproheptadine hydrochloride, levocabastine hydrochloride, astemizole, bepotastine, desloratadine, TAK-427, ZCR-2060, NIP-530, mometasone furoate, mizolastine, BP-294, andolast, auranofin, and acrivastine.

Examples of the antiallergic drug include a chemical mediator release inhibitor such as sodium cromoglicate, tranilast, amlexanox, repirinast, ibudilast, pemirolast potassium, dazanolast, nedocromil, cromoglicate, or israpafant; a histamine antagonist such as ketotifen fumarate, azelastine hydrochloride, oxatomide, mequitazine, terfenadine, emedastine difumarate, epinastine hydrochloride, ebastine, cetirizine hydrochloride, olopatadine hydrochloride, loratadin, or fexofenadine; a thromboxane synthase inhibitor such as ozagrel hydrochloride or imitrodast sodium; a thromboxane antagonist such as seratrodast, ramatroban, domitroban calcium hydrate, or KT-2-962; and a Th2 cytokine inhibitor such as suplatast tosilate.

Examples of the bronchodilator include a xanthine derivative such as aminophylline, theophylline, doxofylline, cipamfylline, diprophylline, proxyphylline, or choline theophylline; a sympathomimetic agent such as epinephrine, ephedrine hydrochloride, dl-methylephedrine hydrochloride, methoxyphenamine hydrochloride, isoproterenol sulfate, isoproterenol hydrochloride, orciprenaline sulfate, clorprenaline hydrochloride, trimetoquinol hydrochloride, salbutamol sulfate, terbutaline sulfate, hexoprenaline sulfate, tulobuterol hydrochloride, procaterol hydrochloride, fenoterol hydrobromide, formoterol fumarate, clenbuterol hydrochloride, mabuterol hydrochloride, salmeterol xinafoate, R,R-formoterol, tulobuterol, pirbuterol hydrochloride, ritodrine hydrochloride, bambuterol, dopexamine hydrochloride, meluadrine tartrate, AR-C68397, levosalbutamol, KUR-1246, KUL-7211, AR-C89855, or S-1319; and a parasympatholytic drug such as ipratropium bromide, flutropium bromide, oxitropium bromide, cimetropium bromide, temiverine, tiotropium bromide, or revatropate.

Examples of the leukotriene synthesis inhibitor include auranofin, proglumetacin maleate, L-674636, A-81834, UPA-780, A-93178, MK-886, REV-5901A, SCH-40120, MK-591, Bay-x-1005, Bay-y-1015, DTI-0026, amlexanox, and E-6700.

Examples of the prostaglandins include a PGE2 EP1 receptor, PGE2 EP2 receptor, PGE2 EP3 receptor, or PGE2 EP4 receptor agonist or antagonist; a PGD2 receptor or CRTH2 receptor agonist or antagonist; a PGF FP receptor agonist or antagonist; a PGI IP receptor agonist or antagonist; and a TX receptor agonist or antagonist.

Examples of the leukotriene receptor antagonist include pranlukast hydrate, montelukast, zafirlukast, seratrodast, MCC-847, KCA-757, CS-615, YM-158, L-740515, CP-195494, LM-1484, RS-635, A-93178, S-36496, BIIL-284, and ONO-4057.

Examples of other antitussive drugs include codeine phosphate, dihydrocodeine phosphate, oxymethebanol, dextromethorphan hydrobromide, pentoxyverine citrate, dimemorfan phosphate, oxeladin citrate, cloperastine, benproperine phosphate, clofedanol hydrochloride, fominoben hydrochloride, noscapine, tipemidine hibenzate, eprazinone hydrochloride, and a *Plantago* herb extract.

Examples of the expectorant include foeniculated ammonia spirit, sodium bicarbonate, potassium iodide, bromhexine hydrochloride, a cherry bark extract, carbocysteine, fudosteine, ambroxol hydrochloride, an ambroxol hydrochloride sustained release preparation, methylcysteine hydrochloride, acetylcysteine, ethyl L-cysteine hydrochloride, and tyloxapol.

Examples of the antipruritic agent include diphenhydramine hydrochloride, crotamiton, and lidocaine.

The present invention has the following aspects.

<1a> A method of preventing, suppressing, or treating a symptom associated with an allergic reaction, the method including administering a compound having a P2X4 receptor antagonizing action (for example, the compounds represented by the general formulas (A) to (BII)) or a pharmaceutically acceptable salt thereof to a subject in need of the method (for example, mammals including human) at a dose effective for preventing, suppressing, or treating the symptom associated with the allergic reaction;

<2a> the method according to <1a>, in which the symptom associated with the allergic reaction is an allergic disease;

<3a> the method according to <1a> or <2a>, in which the symptom associated with the allergic reaction is a symptom associated with a type I allergic reaction;

<4a> the method according to any one of <1a> to <3a>, in which the symptom associated with the allergic reaction is an anaphylactic shock;

<5a> the method according to any one of <1a> to <3a>, in which the symptom associated with the allergic reaction is allergic rhinitis;

<6a> the method according to any one of <1a> to <3a>, in which the symptom associated with the allergic reaction is bronchial asthma;

<7a> the method according to any one of <1a> to <3a>, in which the symptom associated with the allergic reaction is allergic dermatitis;

<8a> the method according to any one of <1a> to <3a>, in which the symptom associated with the allergic reaction is pollinosis;

<9a> the method according to any one of <1a> to <3a>, in which the symptom associated with the allergic reaction is urticaria;

<10a> the method according to any one of <1a> to <3a>, in which the symptom associated with the allergic reaction is atopic dermatitis;

<11a> the method according to <1a>, in which the allergic reaction is an allergic reaction accompanied by inflammation; and <12a> the method according to <1a>, in which the allergic reaction is an allergic reaction accompanied by release of secretory granules within mast cells to the outside of the cells.

The present invention has the following other aspects.

<1b> A compound having a P2X4 receptor antagonizing action (for example, the compounds represented by the general formulas (A) to (BII)) or a pharmaceutically acceptable salt thereof, which is for use in prevention, suppression, or treatment of a symptom associated with an allergic reaction;

<2b> the compound or a pharmaceutically acceptable salt thereof for the use according to <1b>, in which the symptom associated with the allergic reaction is an allergic disease;

<3b> the compound or a pharmaceutically acceptable salt thereof for the use according to <1b> or <2b>, in which the symptom associated with the allergic reaction is a symptom associated with a type I allergic reaction;

<4b> the compound or a pharmaceutically acceptable salt thereof for the use according to any one of <1b> to <3b>, in which the symptom associated with the allergic reaction is an anaphylactic shock;

<5b> the compound or a pharmaceutically acceptable salt thereof for the use according to any one of <1b> to <3b>, in which the symptom associated with the allergic reaction is allergic rhinitis;

<6b> the compound or a pharmaceutically acceptable salt thereof for the use according to any one of <1b> to <3b>, in which the symptom associated with the allergic reaction is bronchial asthma;

<7b> the compound or a pharmaceutically acceptable salt thereof for the use according to any one of <1b> to <3b>, in which the symptom associated with the allergic reaction is allergic dermatitis;

<8b> the compound or a pharmaceutically acceptable salt thereof for the use according to any one of <1b> to <3b>, in which the symptom associated with the allergic reaction is pollinosis;

<9b> the compound or a pharmaceutically acceptable salt thereof for the use according to any one of <1b> to <3b>, in which the symptom associated with the allergic reaction is urticaria;

<10b> the compound or a pharmaceutically acceptable salt thereof for the use according to any one of <1b> to <3b>, in which the symptom associated with the allergic reaction is atopic dermatitis;

<11b> the compound or a pharmaceutically acceptable salt thereof for the use according to <1b>, in which the allergic reaction is an allergic reaction accompanied by inflammation; and <12b> the compound or a pharmaceutically acceptable salt thereof for the use according to <1b>, in which the allergic reaction is an allergic reaction accompanied by release of secretory granules within mast cells to the outside of the cells.

The present invention further has the following other aspects.

<1c> Use of a compound having a P2X4 receptor antagonizing action (for example, the compounds represented by the general formulas (A) to (BII)) or a pharmaceutically acceptable salt thereof for producing a pharmaceutical composition for preventing, suppressing, or treating a symptom associated with an allergic reaction;

<2c> the use according to <1c>, in which the symptom associated with the allergic reaction is an allergic disease;

<3c> the use according to <1c> or <2c>, in which the symptom associated with the allergic reaction is a symptom associated with a type I allergic reaction;

<4c> the use according to any one of <1c> to <3c>, in which the symptom associated with the allergic reaction is an anaphylactic shock;

<5c> the use according to any one of <1c> to <3c>, in which the symptom associated with the allergic reaction is allergic rhinitis;

<6c> the use according to any one of <1c> to <3c>, in which the symptom associated with the allergic reaction is bronchial asthma;

<7c> the method according to any one of <1c> to <3c>, in which the symptom associated with the allergic reaction is allergic dermatitis;

<8c> the use according to any one of <1c> to <3c>, in which the symptom associated with the allergic reaction is pollinosis;

<9c> the use according to any one of <1c> to <3c>, in which the symptom associated with the allergic reaction is urticaria;

<10c> the use according to any one of <1c> to <3c>, in which the symptom associated with the allergic reaction is atopic dermatitis;

<11c> the use according to <1c>, in which the allergic reaction is an allergic reaction accompanied by inflammation; and <12c> the use according to <1c>, in which the allergic reaction is an allergic reaction accompanied by release of secretory granules within mast cells to the outside of the cells.

EXAMPLES

Hereinafter, the present invention is more specifically described with Examples, however, the scope of the present invention is not limited to the following Examples.

In the following Examples, as a P2X4 receptor antagonist, a 5-[3-(5-thioxo-4H-[1,2,4]oxadiazol-3-yl)phenyl]-1H-naphtho[1,2-b][1,4]diazepine-2,4(3H,5H)-dione sodium salt (a salt in Example 14 of WO 2010/093061 A: hereinafter, referred to as "Compound A" for convenience), 5-[4-(2-iodobenzoylamino)phenyl]-1H-naphtho[1,2-b][1,4]diazepine-2,4(3H,5H)-dione (a compound in Example 48 of WO 2013/105608 A: hereinafter, referred to as "Compound B"), and other compounds shown below were used:

a 5-[3-(1H-tetrazol-5-yl)phenyl]-1H-naphtho[1,2-b][1,4]diazepine-2,4(3H,5H)-dione sodium salt; 5-[4-[2-(trifluoromethyl)benzoyl]aminophenyl]-1H-naphtho[1,2-b][1,4]diazepine-2,4(3H,5H)-dione; 5-[4-[(2-chlorophenylacetyl)amino]phenyl]-1H-naphtho[1,2-b][1,4]diazepine-2,4(3H,5H)-dione; 1-[4-(2,4-dioxo-1,2,3,4-tetrahydronaphtho[1,2-b][1,4]diazepin-5-yl)phenyl]-3-phenylurea; 5-[4-[(2-ethylbenzoyl)amino]phenyl]-1H-naphtho[1,2-b][1,4]diazepine-2,4(3H,5H)-dione; 5-[4-(2-tert-butylbenzoylamino)phenyl]-1H-naphtho[1,2-b][1,4]diazepine-2,4(3H,5H)-dione; 5-[4-(2-iodobenzoyl)aminophenyl]-1,2,3,4,8,9,10,11-octahydronaphtho[1,2-b][1,4]diazepine-2,4(3H,5H)-dione; 5-[4-(6-chloro-2-hydroxybenzoylamino)phenyl]-1H-naphtho[1,2-b][1,4]diazepine-2,4(3H,5H)-dione; N-[4-(2,4-dioxo-1,2,3,4-tetrahydronaphtho[1,2-b][1,4]diazepin-5-yl)phenyl]benzenesulfonamide; 1-(2-chlorophenyl)-N-[4-(2,4-dioxo-1,2,3,4-tetrahydronaphtho[1,2-b][1,4]diazepin-5-yl)phenyl]methanesulfonamide; 1-(2-chlorophenyl)-N-[4-(2,4-dioxo-1,2,3,4,8,9,10,11-octahydronaphtho[1,2-b][1,4]diazepin-5-yl)phenyl]methanesulfonamide; 1-(2-bromophenyl)-N-[4-(2,4-dioxo-1,2,3,4-tetrahydronaphtho[1,2-b][1,4]diazepin-5-yl)phenyl]methanesulfonamide; N-[4-(2,4-dioxo-1,2,3,4-tetrahydronaphtho[1,2-b][1,4]diazepin-5-yl)phenyl]-1-(2-methylphenyl)methanesulfonamide; N-[4-(2,4-dioxo-1,2,3,4-tetrahydronaphtho[1,2-b][1,4]diazepin-5-yl)phenyl]-2-phenylethanesulfonamide; 1-(2-chlorophenyl)-N-[4-(2,4-dioxo-1,2,3,4,8,9,10,11-octahydronaphtho[1,2-b][1,4]diazepin-5-yl)phenyl]-N-methylmethanesulfonamide; 1-(2-chlorophenyl)-N-[4-(2-oxo-2,3-dihydro-1H-naphtho[1,2-e][1,4]diazepin-5-yl)phenyl]methanesulfonamide; 5-[4-[(2-methylpyridin-3-yl)carbonylamino]phenyl]-1H-naphtho[1,2-b][1,4]diazepine-2,4(3H,5H)-dione hydrochloride; 5-[4-[(2-chloropyridin-3-yl)carbonylamino]phenyl]-1H-naphtho[1,2-b][1,4]diazepine-2,4(3H,5H)-dione; 5-[4-[2-[(pyridin-2-yl)oxy]acetylamino]phenyl]-1H-naphtho[1,2-b][1,4]diazepine-2,4(3H,5H)-dione; and 5-[4-[(2-isopropylbenzoyl)amino]phenyl]-1H-naphtho[1,2-b][1,4]diazepine-2,4(3H,5H)-dione.

Example 1: Measurement of P2X4 Receptor Antagonistic Action of Compound Which Is Active Ingredient of Present Invention (Test Method)

A P2X4 receptor antagonistic action of a compound which is the active ingredient of the present invention was measured. 1321N1 cells into which ATP receptors (human P2X4) were introduced were used as a P2X4 receptor stable expression system. The P2X4-receptor-expressing cells were seeded into a 96-well plate and cultured for 24 hours under a condition of 37° C. and 5% CO2 to be used for calcium measurement. Fura-2AM, which is a calcium fluorescent indicator, was dissolved in an extracellular fluid for calcium imaging, and the seeded cells were treated therewith and left to stand at room temperature for 45 minutes, thereby incorporating Fura-2AM into the cells. EnVision (PerkinElmer) which is a microplate reader was used for the measurement. 510 nm fluorescences F340 and F380 that are emitted when the cells are irradiated with light radiating from a xenon lamp and transmitted through 340 nm and 380 nm filters, respectively, were observed, and change in a ratio value F340/F380 was used as an index of intracellular calcium change. Measurement was performed by adding ATP to each well such that the final concentration of ATP becomes 1 μM and observing an ATP-induced intracellular calcium response over time. Inhibitory activity of a test substance was measured by performing pretreatment on the test substance for 15 minutes by adding ATP thereto, and the inhibitory activity was calculated by comparison with a case of absence of the test substance. The results are shown in the following Table 29.

(Test Result)

TABLE 29

| Test compound | $IC_{50}$ (μM) |
|---|---|
| CompoundA2 | 0.53 |
| Compound A17(Compound A) | 0.27 |
| Compound B2 | 0.75 |
| Compound B13 | 0.54 |
| Compound B20 | 1.2 |
| Compound B48(Compound B) | 0.30 |
| Compound B57 | 0.72 |
| Compound B71 | 0.4 |
| Compound B106 | 1.8 |
| Compound B118 | 1.10 |
| Compound B146 | 0.67 |
| Compound B173 | 0.064 |
| Compound B177 | 0.056 |
| Compound B180 | 0.05 |
| Compound B181 | 0.068 |
| Compound B183 | 0.42 |
| Compound B196 | 0.97 |
| Compound B197 | 0.44 |
| Compound B208 | 1.3 |

TABLE 29-continued

| Test compound | $IC_{50}$ (μM) |
|---|---|
| Compound B209 | 0.94 |
| Compound B210 | 1.4 |
| Compound B214 | 0.62 |

Example 2: Effects on Degranulation Reaction of BMMCs

A suppressive effect of Compound A or B having a P2X4 receptor antagonizing action on a degranulation reaction caused by costimulation of IgE-sensitized bone marrow-derived mast cells (referred to as BMMCs in the present specification) with dinitrophenyl-conjugated human serum albumin (2,4-Dinitrophenyl-Human Serum Albumin, referred to as DNP-HSA in the present specification) (10 ng/mL) and ATP (0.1 mM) was observed. The degranulation reaction was performed by obtaining a degranulation rate using a β-hexosaminidase release rate as an index. The β-hexosaminidase release rate was measured as in the section (Degranulation Experiment) below.

(Setting Up of BMMCs)

Bone marrow was collected from femora of male C57BL/6J mice (7 to 8 weeks old, produced by Japan SLC, Inc). Red blood cells were hemolyzed, and culture was performed in a medium containing 10% fetal bovine serum (FBS), penicillin (100 unit/ml), streptomycin (100 μg/ml), and recombinant mouse IL-3 (10 ng/ml, manufactured by PeproTech, Inc.) for 14 days. Stem cell factor (SCF) (10 ng/ml) was added to the medium from Day 15, and the culture was performed for 35 to 42 days to be used for the experiment. Whether the cells were differentiated into mast cells was confirmed by the degrees the of c-KIT and FcεRI expressions. The confirmation was performed by using FACSCant II (manufactured by BD Biosciences).

(Degranulation Experiment)

Anti-DNP-IgE antibody (clone: SPE-7, manufactured by Sigma-Aldrich, Inc.) was added to the BMMC culture solution so that the concentration reached 50 ng/ml, and the BMMCs were sensitized overnight. To be used in the experiment, the BMMCs were washed with PBS(−) and suspended in Krebs Ringer-HEPES Buffer (NaCl 130 mM, KCl 4.7 mM, $NaHCO_3$4.0 mM, $KH_2P_4$ 1.2 mM, Glucose 11.5 mM, HEPES 10 mM, and $CaCl_2 \cdot H_2O$ 1.8 mM) so that the concentration reached $1\times10^6$ cell/ml.

Next, Compound A (1 μM, 3 μM, or 10 μM), Compound B (1 μM, 3 μM, or 10 μM), or 0.1% DMSO as a control was added to the BMMCs sensitized with IgE, and the cells were subjected to preincubation at room temperature for 10 minutes.

Then, the BMMCs were each set up into the following 4 groups.

(1) A group in which nothing was added to the BMMCs, (2) a group in which only ATP was added to the BMMCs, (3) a group in which only DNP-HSA (10 ng/ml) was added to the BMMCs as an antigen, and (4) a group in which a mixed solution of ATP and DNP-HSA (10 ng/ml) was added to the BMMCs at once.

Each of the 4 groups was stimulated at 37° C. for 5 minutes and rapidly cooled on ice, and then centrifugation was performed to stop the reaction. After collecting the supernatant, precipitated cells were lysed with 0.1% triton X-100. The supernatant and the cell lysis solution (50 μL) were mixed with 10 mM 4-Nitrophenyl N-acetyl-p-D-glucosaminide (manufactured by Sigma-Aldrich, Inc.) which was a β-hexosaminidase substrate/50 mM citrate buffer (pH 4.5, 50 μL), and the mixture was incubated at 37° C. for 30 minutes. 50 mM carbonate buffer (pH 10.0, 100 μL) was added to stop the reaction, and absorbance was measured at 405/655 using an absorbance microplate reader Sunrise (manufactured by Tecan Trading AG). The β-hexosaminidase release rate was obtained from the following formula.

β-hexosaminidase release rate=Absorbance of supernatant/(Absorbance of supernatant+absorbance of cell lysis station)×100

Figure 2:
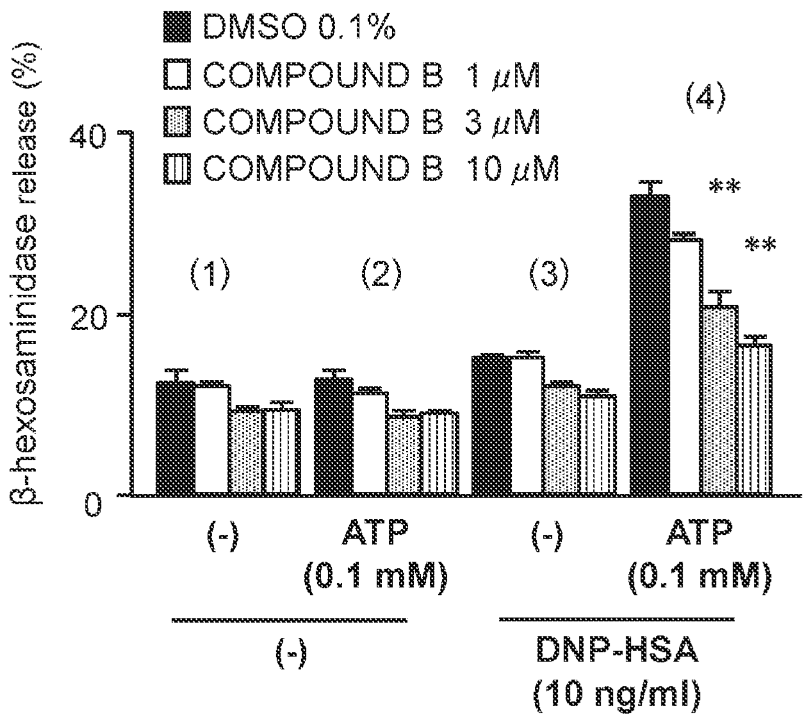
FIG. 2 is a diagram obtained by observing a suppressive effect of Compound B on a degranulation reaction caused by costimulation of IgE-sensitized BMMCs with DNP-HSA and ATP.

Note that, in the present Example, the numbers of specimens were all n=3, and the significant differences in the present Example are indicated with "*" or "" in FIGS. 1 and 2**, "*" indicating P<0.05, and "**" P<0.01. In addition, "*" or "" in FIGS. 1 and 2** each indicate that there was a significant difference as a result of comparison with the control in the same group.

(Test Result)

Regarding Compound A

In the groups of (1) to (3) that were not subjected to the costimulation with ATP and DNP-HSA (10 ng/ml), the β-hexosaminidase release rates of the BMMCs administered with Compound A and the control BMMCs were all lower than 10% ((1) to (3) in FIG. 1). On the other hand, in the group of (4) that was subjected to the costimulation with ATP and DNP-HSA (10 ng/ml), the β-hexosaminidase release rate of the control BMMCs was approximately 25% ((4) in FIG. 1). However, the β-hexosaminidase release rates of the BMMCs in the same group which were preincubated with Compound A decreased in a dose-dependent manner of Compound A compared to the control BMMCs, and the release rates significantly decreased at all concentrations of 1 μM, 3 μM, and 10 μM ((4) in FIG. 1).

Regarding Compound B

In the groups of (1) to (3) that were not subjected to the costimulation with ATP and DNP-HSA (10 ng/ml), the β-hexosaminidase release rates of the BMMCs administered with Compound B and the control BMMCs were all from approximately 10% to approximately 15% ((1) to (3) in FIG. 2). On the other hand, in the group of (4) that was subjected to the costimulation with ATP and DNP-HSA (10 ng/ml), the β-hexosaminidase release rate of the control BMMCs was higher than 30% ((4) in FIG. 2). However, the β-hexosaminidase release rates of the BMMCs in the same group which were preincubated with Compound B decreased in a dose-dependent manner of Compound B compared to the control BMMCs, and the release rates significantly decreased in BMMCs preincubated with Compound B at the concentrations of 3 μM and 10 μM ((4) in FIG. 2).

Example 3: Effects on Passive Cutaneous Anaphylaxis

The suppressive effects of Compound A and Compound B having a P2X4 receptor antagonizing action on passive cutaneous anaphylaxis (in the present specification, referred to as PCA) were measured by sensitizing mice with IgE in advance, preparing a group of the mice administered with Compound A or Compound B and a group of the mice not administered with Compound A or Compound B, and inducing PCA in the mice of each group.

(Preparation of IgE-Sensitized Mice)

The mice were sensitized by subcutaneously administering 100 ng/20 μL IgE into the right ears under anesthesia. Only physiological saline was administered into the left ears.

Male C57BL/6J mice (10 to 11 weeks old, produced by Japan SLC, Inc) were used as the mice.

(Administration of Drugs)

The IgE-sensitized mice were intraperitoneally administered with Compound A (10 mg/kg) contained in physiological saline 30 minutes before the DNP-HSA administration. Note that the DNP-HSA administration was performed by tail vein administration and was arranged to be performed 24 hours after the preparation of the IgE-sensitized mice.

Furthermore, among the rest of the IgE-sensitized mice, some were intraperitoneally administered with Compound B (10 mg/kg) contained in a solvent in which DMSO: 65% Kolliphor EL (manufactured by BASF SE):sterile water for injection was adjusted to 1:1:8 (hereinafter, referred to as a solvent B) 1 hour before the DNP-HSA administration. Note that the concentration of 65% Kolliphor EL was prepared using ethanol and a small amount of sterile water for injection (or water). In addition, the DNP-HSA administration was arranged to be performed 24 hours after the preparation of the IgE-sensitized mice.

Moreover, with the rest of the IgE-sensitized mice, a group administered with physiological saline as a control for Compound A (vehicle group) and a group administered with the solvent B as a control for Compound B (vehicle group) were prepared.

(Preparation of PCA Model Mice)

Anaphylaxis was induced by tail vein administration of 100 ng/200 μL (physiological saline) DNP-HSA containing 0.5% Evans blue 24 hours after the preparation of the IgE-sensitized mice, thereby preparing PCA model mice.

(Measurement of Suppressive Effect)

Since the body fluid containing Evans Blue in the PCA model mice moved from the inside of a blood vessel to the auricle due to edema, the effect of Compound A or B on PCA was measured by measuring a change in the amount of Evans Blue in the auricle in the case where the tail vein administration of DNP-HSA was performed.

The PCA model mice were euthanized 30 minutes after the DNP-HSA administration, the auricles were collected, and the weights of the auricles were measured. The collected auricles were chopped into small pieces, and Evans blue was extracted by heating (65° C.) the chopped auricles in formamide (1 mL) overnight. Absorbance (620 nm) of the extracted Evans blue and the calibration curve was measured using the absorbance microplate reader Sunrise (Tecan Trading AG), and the concentrations were calculated.

Figure 3:
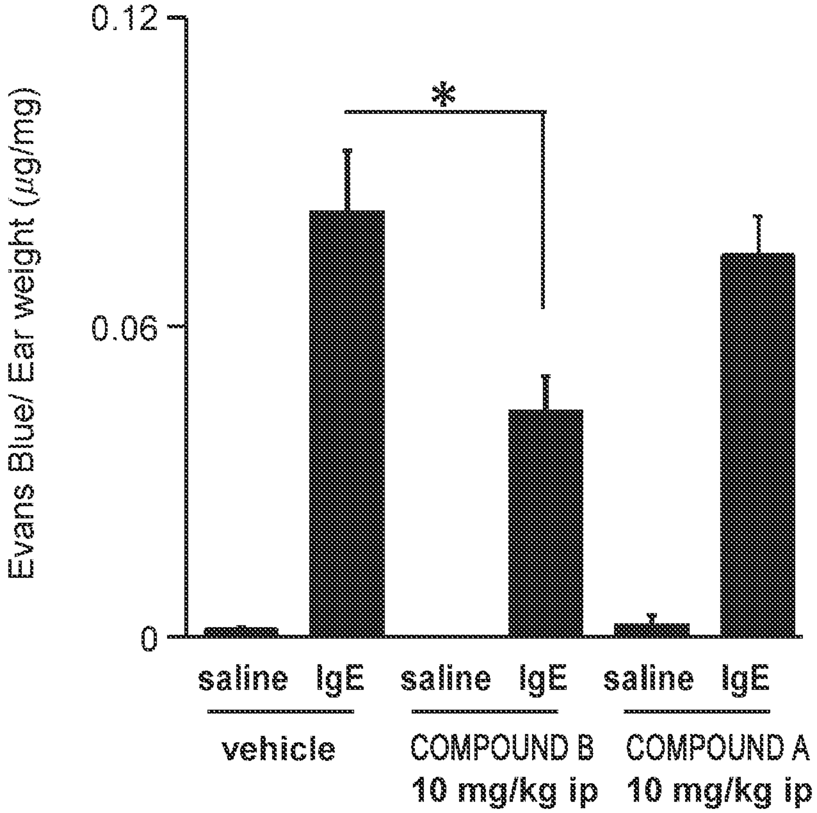
FIG. 3 is a diagram obtained by measuring the suppressive effects of Compound A and Compound B on passive cutaneous anaphylaxis (PCA) by sensitizing mice with IgE in advance, preparing a group of the mice administered with Compound A or Compound B and a group of the mice not administered with Compound A or Compound B, and inducing PCA in the mice of each group.

Note that, in the present Example, the numbers of specimens were all n=5, and the significant differences in the present Example are indicated with "*" in FIG. 3, which indicates that P<0.05. In addition, "*" in FIG. 3 indicates that there was a significant difference as a result of comparing the group administered with each compound with the group not administered with the compound (vehicle group).

(Test Result)

The increase in Evans Blue per auricle weight was significantly suppressed when the tail vein administration of DNP-HSA was performed after pretreatment with Compound B (10 mg/kg).

Furthermore, as in the case of intraperitoneal administration, the pretreatment with Compound B (10 mg/kg) significantly suppressed the increase in Evans Blue per auricle weight even in a case where Compound B was orally administered (not shown in the drawing).

Example 4: Effects on Passive Systemic Anaphylaxis

The suppressive effects of Compound A and Compound B having a P2X4 receptor antagonizing action on passive systemic anaphylaxis (in the present specification, referred to as PSA) were measured by sensitizing mice with IgE in advance, preparing a group of the mice administered with Compound A or Compound B and a group of the mice not administered with Compound A or Compound B, and inducing PSA in the mice of each group.

(Preparation of IgE-Sensitized Mice)

The mice were sensitized by tail vein administration of 10 μg/200 μL IgE (physiological saline) under anesthesia.

Male C57BL/6J mice (7 to 8 or 10 to 11 weeks old, produced by Japan SLC, Inc) were used as the mice.

(Administration of Drugs)

The IgE-sensitized mice were intraperitoneally administered with Compound A (10 mg/kg) contained in physiological saline 30 minutes before the DNP-HSA administration. The DNP-HSA administration was arranged to be performed 24 hours after the preparation of the IgE-sensitized mice.

In addition, among the rest of the IgE-sensitized mice, some were intraperitoneally administered with Compound B (10 mg/kg) contained in the solvent B 1 hour before the DNP-HAS administration. The DNP-HSA administration was arranged to be performed 24 hours after the preparation of the IgE-sensitized mice.

Moreover, with the rest of the IgE-sensitized mice, a group administered with physiological saline as a control for Compound A (vehicle group) and a group administered with the solvent B as a control for Compound B (vehicle group) were prepared.

(Preparation of PSA Model Mice)

PSA model mice were prepared, and anaphylaxis was induced by tail vein administration of 100 ng/200 μL (physiological saline) DNP-HSA to unanesthetized mice 24 hours after the preparation of the IgE-sensitized mice.

(Measurement of Suppressive Effect)

Inducing systemic anaphylaxis causes a rapid decrease in the body temperatures of the PSA model mice. Therefore, the effect of Compound A or B on passive systemic anaphylaxis was measured by measuring a change in the body temperature in the case where the tail vein administration of DNP-HSA was performed.

The measurement of the body temperature change was performed by measuring, with BAT-7001H Thermometer (Physitemp Instruments, LLC.), the rectal temperatures every 5 minutes from 0 minutes to 60 minutes after the administration, the 0 minutes being defined as the time of the DNP-HSA administration.

Figure 4:
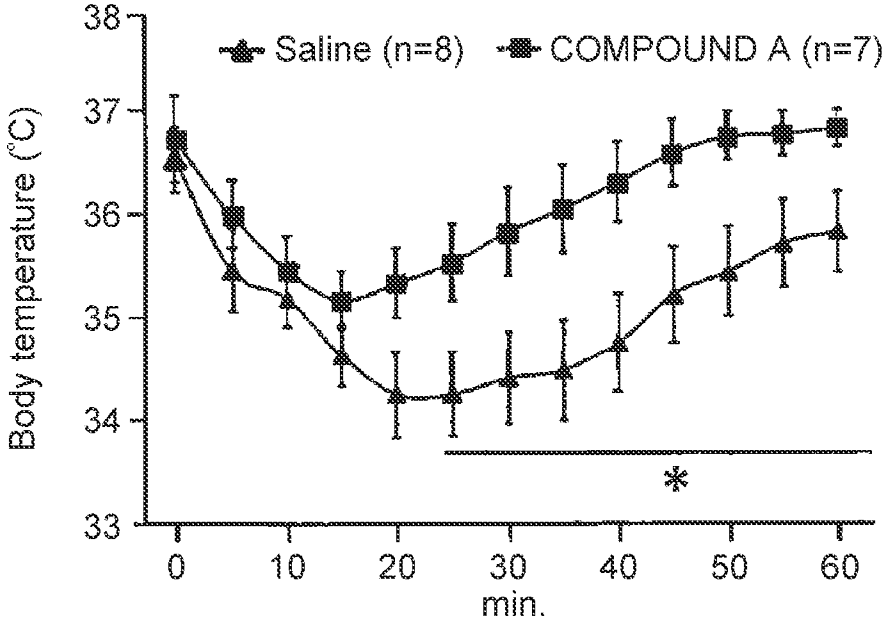
FIG. 4 is a diagram obtained by measuring a suppressive effect of Compound A on passive systemic anaphylaxis (PSA) by sensitizing mice with IgE in advance, preparing a group of the mice administered with Compound A and a group of the mice not administered with Compound A, and inducing PSA in the mice of each group.
Figure 5:
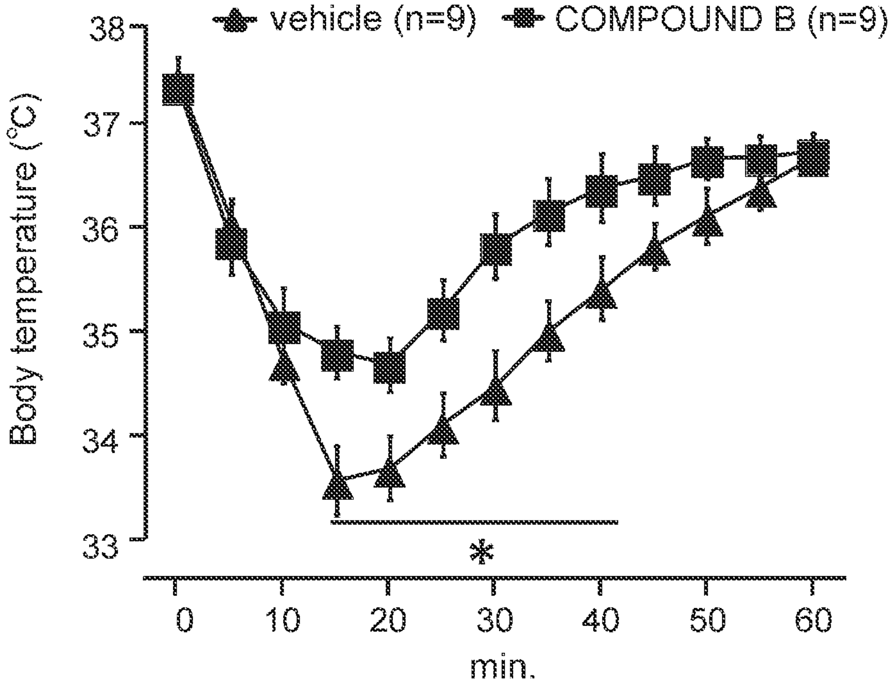
FIG. 5 is a diagram obtained by measuring a suppressive effect of Compound B on passive systemic anaphylaxis (PSA) by sensitizing mice with IgE in advance, preparing a group of the mice administered with Compound B and a group of the mice not administered with Compound B, and inducing PSA in the mice of each group.

Note that, in the present Example, the numbers of specimens were n=7 in the Compound A group, n=8 in the control group for Compound A, and n=9 in the Compound B group and the control group therefor, and the significant differences in the present Example are indicated with "*" in FIGS. 4 and 5, which indicates that P<0.05. In addition, "*" in FIGS. 4 and 5 indicates that there was a significant difference as a result of comparing the group administered with each compound with the control group for each compound (vehicle group).

(Test Result)

When the tail vein administration of DNP-HSA was performed after pretreating the IgE-sensitized mice with Compound A or B, a significant body temperature decrease-suppressing effect was observed in both cases. Moreover, there was a significant difference in the body temperature decrease-suppressing effect of Compound A over at least 35 minutes, and the effect persisted even after 60 minutes.

Example 5: Effects on Degranulation Reaction of BMMCs

A suppressive effect of Compound A on each of a degranulation reaction caused by costimulation of the IgE-sensitized BMMCs with DNP-HSA (10 ng/mL) and ATP (0.1 mM) and a degranulation reaction caused by costimulation of the IgE-sensitized BMMCs with Prostaglandin E2 (in the present specification, referred to as PGE2) (1 μg/mL) and ATP (0.1 mM) was observed.

The degranulation reaction was performed by obtaining a degranulation rate using a β-hexosaminidase release rate as an index. The β-hexosaminidase release rate was measured as in the section (Degranulation Experiment) below.

(Setting Up of BMMCs)

Setting up of BMMCs was performed according to the method described in Example 2.

(Degranulation Experiment)

Anti-DNP-IgE antibody (clone: SPE-7, manufactured by Sigma-Aldrich, Inc.) was added to the BMMC culture solution so that the concentration reached 50 ng/ml, and the BMMCs were sensitized overnight. To be used in the experiment, the BMMCs were washed with PBS(−) and suspended in Krebs Ringer-HEPES Buffer (NaCl 130 mM, KCl 4.7 mM, $NaHCO_3$ 4.0 mM, $KH_2P_4$ 1.2 mM, Glucose 11.5 mM, HEPES 10 mM, and $CaCl_2 \cdot H_2O$ 1.8 mM) so that the concentration reached $1\times10^6$ cell/ml.

Next, Compound A (1 μM, 3 μM, or 10 μM) or 0.1% DMSO as a control was added to the BMMCs sensitized with IgE, and the cells were subjected to preincubation at room temperature for 10 minutes.

Then, the BMMCs were each set up into the following 6 groups. Note that the numbers in the parentheses below match the numbers in parentheses in FIG. 6.

(1) A group in which nothing was added to the BMMCs, (2) a group in which only ATP was added to the BMMCs, (3) a group in which only $PGE_2$ (1 μM) was added to the BMMCs, (4) a group in which a mixed solution of ATP and $PGE_2$ (1 μM) was added to the BMMCs at once, (5) a group in which only DNP-HSA (10 ng/ml) was added to the BMMCs as an antigen, and (6) a group in which a mixed solution of ATP and DNP-HSA (10 ng/ml) was added to the BMMCs at once.

Each of the 6 groups was stimulated at 37° C. for 5 minutes and rapidly cooled on ice, and then centrifugation was performed to stop the reaction. After collecting the supernatant, precipitated cells were lysed with 0.1% triton X-100. The supernatant and the cell lysis solution (50 μL) were mixed with 10 mM 4-Nitrophenyl N-acetyl-β-D-glucosaminide (manufactured by Sigma-Aldrich, Inc.) which was a β-hexosaminidase substrate/50 mM citrate buffer (pH 4.5, 50 μL), and the mixture was incubated at 37° C. for 30 minutes. 50 mM carbonate buffer (pH 10.0, 100 μL) was added to stop the reaction, and absorbance was measured at 405/655 using an absorbance microplate reader Sunrise (manufactured by Tecan Trading AG). The β-hexosaminidase release rate was obtained from the following formula.

β-hexosaminidase release rate=Absorbance of supernatant/(Absorbance of supernatant+absorbance of cell lysis station)×100

(Test Result)

Figure 6:
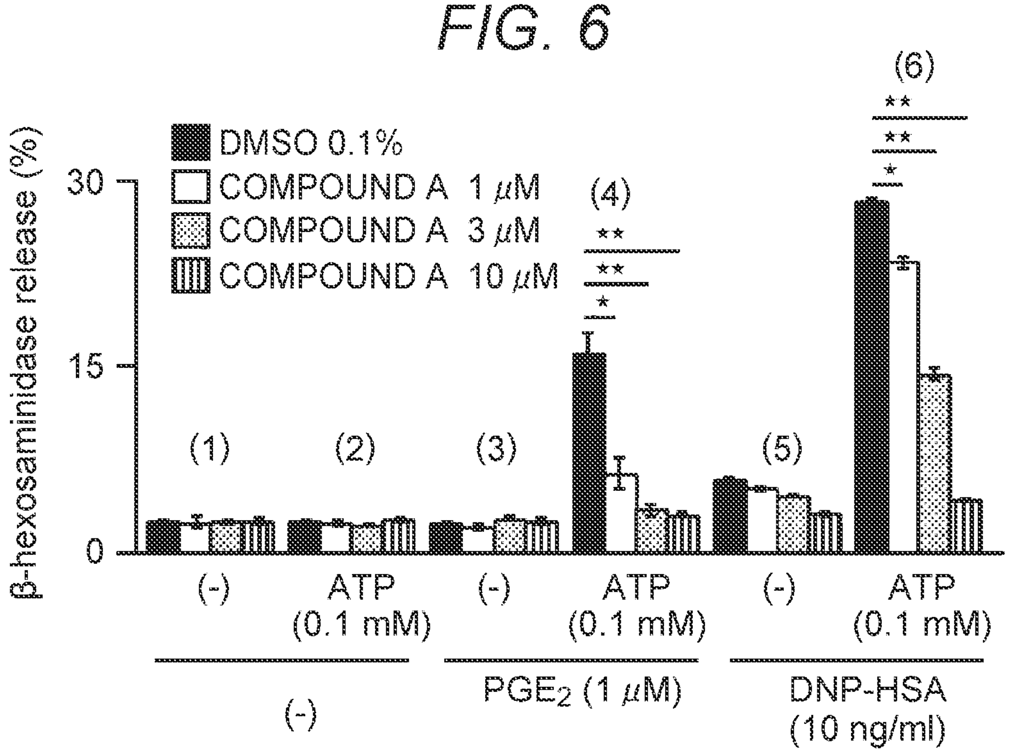
FIG. 6 is a diagram obtained by observing a suppressive effect of Compound A on a degranulation reaction caused by costimulation of IgE-sensitized BMMCs with $PGE_2$ and ATP.

In the groups of (1) to (3) that were not subjected to the costimulation with ATP (0.1 mM) and $PGE_2$ μM), the β-hexosaminidase release rates of the BMMCs administered with Compound A and the control BMMCs were all lower than 5% ((1) to (3) in FIG. 6). On the other hand, in the group of (4) that was subjected to the costimulation with ATP (0.1 mM) and PGE2 (1 μM), the β-hexosaminidase release rate of the control BMMCs was approximately 15% ((4) in FIG. 6). However, the β-hexosaminidase release rates of the BMMCs in the same group which were preincubated with Compound A decreased in a dose-dependent manner of Compound A compared to the control BMMCs, and the release rates significantly decreased at all concentrations of 1 μM, 3 μM, and 10 μM ((4) in FIG. 6).

Note that, in the present Example, the numbers of specimens were all n=3, and the significant differences in the present Example are indicated with "*" or "" in FIG. 6**, indicating $P<0.05$ and $P<0.01$ (Dunnett), respectively. In addition, "*" or "" in FIG. 6** each indicate that there was a significant difference as a result of comparison with the control in the same group.

Example 6: Action of P2X4 Receptor Inhibitor on IL-6, IL-13, and TNF-α Release by BMMCs (Test Method)

BMMCs were washed with a fresh culture solution and subjected to reactions in the presence and absence of a stimulating agent (100 μM ATP, 1 μM PGE2, 100 μM ATP+1 μM PGE2) for 3 hours.

The grouping is as shown below and matches the numbers in parentheses indicated in FIGS. 7 to 9.

(1) A group in which nothing was added to the BMMCs, (2) a group in which only ATP was added to the BMMCs, (3) a group in which only $PGE_2$ was added to the BMMCs, and (4) a group in which a mixed solution of ATP and PGE2 was added to the BMMCs at once.

The action of Compound A was observed by performing pretreatment with Compound A at a concentration of 10 μM for 5 minutes. Cytokines released into the reaction solution (interleukin (IL)-6, IL-13, and TNF-α) were measured using ELISA kits (Invitrogen Corporation).

Figure 7:
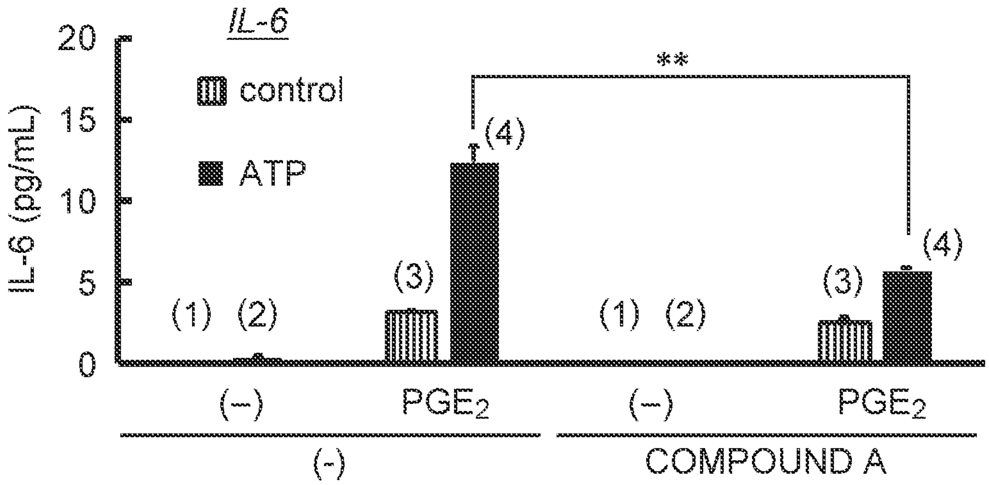
FIG. 7 is a diagram obtained by observing a suppressive effect of Compound A on IL-6 release caused by stimulation of BMMCs.
Figure 8:
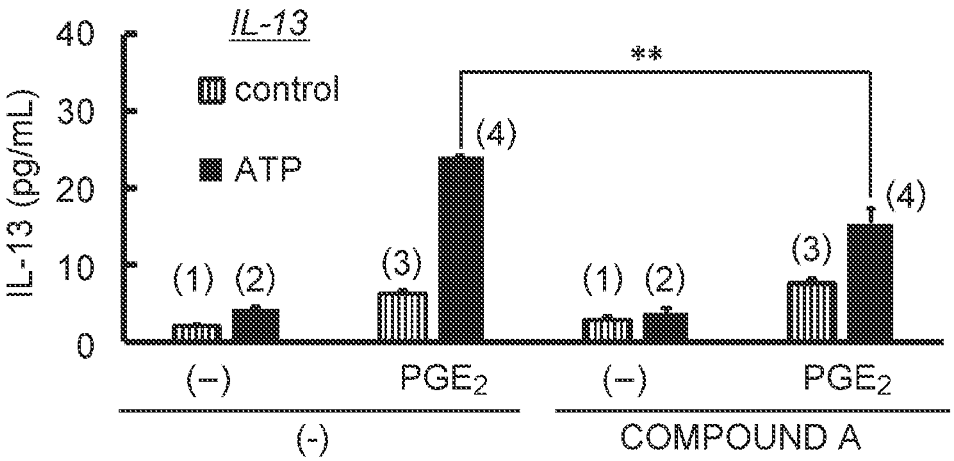
FIG. 8 is a diagram obtained by observing a suppressive effect of Compound A on IL-13 release caused by stimulation of BMMCs.
Figure 9:
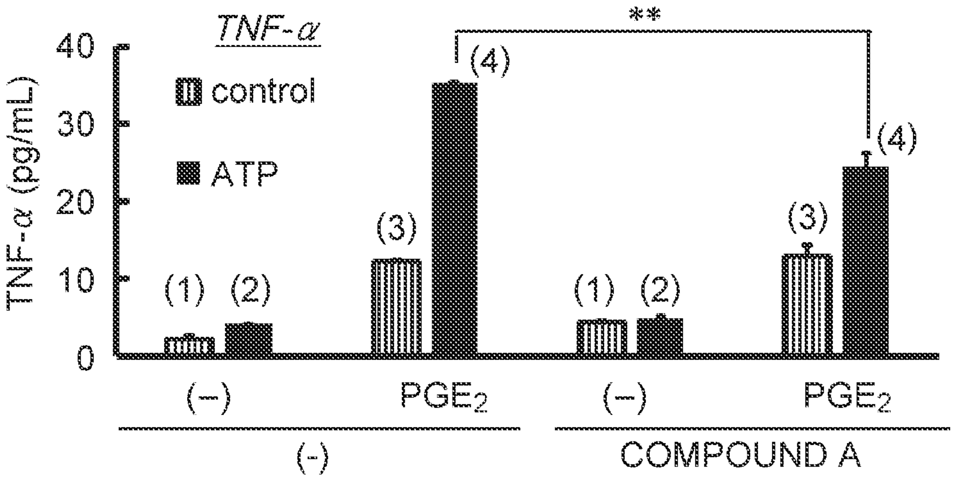
FIG. 9 is a diagram obtained by observing a suppressive effect of Compound A on TNF-α release caused by stimulation of BMMCs.

Note that, in the present Example, the numbers of specimens were all n=3, and the significant differences in the present Example are indicated with "" in FIGS. 7 to 9, indicating that $P<0.01$. In addition, the significant differences in FIGS. 7 to 9** indicate the results of comparison with the group not administered with Compound A.

(Test Result)

The results are shown in FIGS. 7 to 9.

The ATP-induced increases in the IL-6, IL-13, and TNF-α release were shown to be suppressed by Compound A. The results suggest that the compound of the present application is effective for allergic dermatitis, allergic bronchial asthma, or the like.

INDUSTRIAL APPLICABILITY

The pharmaceutical composition of the present invention is useful as a pharmaceutical composition useful in preventing, suppressing, or treating a symptom associated with an allergic reaction, and furthermore, is useful as a pharmaceutical composition useful in preventing, suppressing, or treating an allergic disease, particularly useful as a pharmaceutical composition useful in preventing, suppressing, or treating a symptom associated with a type I allergic reaction, and more particularly useful as a pharmaceutical composition useful in preventing or treating an anaphylactic shock, allergic rhinitis, bronchial asthma, or allergic dermatitis, a pharmaceutical composition useful in suppressing an anaphylactic shock, or a pharmaceutical composition useful in preventing or treating pollinosis, urticaria, or atopic dermatitis, each of which is expected to be highly effective.

The invention claimed is:

1. A method of suppressing or treating a symptom associated with an allergic reaction selected from the group consisting of a symptom associated with a type I allergic reaction, an anaphylactic shock, allergic rhinitis, allergic dermatitis, pollinosis, urticaria, and atopic dermatitis, the method comprising administering a compound having a P2X4 receptor antagonizing action or a pharmaceutically acceptable salt thereof to a subject in need of the method at a dose effective for suppressing or treating the symptom associated with the allergic reaction, wherein the compound is a compound represented by the following formula (A) or the following formula (BI):

(A)

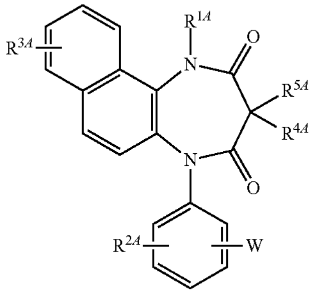

in the formula (A), $R^{1A}$ represents a hydrogen atom;

$R^{2A}$ and $R^{3A}$ represent a hydrogen atom;

$R^{4A}$ and $R^{5A}$ represent a hydrogen atom; and

W represents tetrazole or 1, 2, 4-oxadiazole which may have a substituent; or (BI)

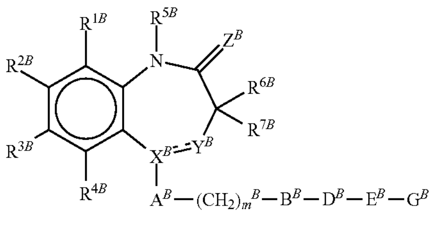

in the formula (BI), $R^{1B}$ and $R^{2B}$ bind together to form a condensed ring selected from the group consisting of a naphthalene ring and a tetrahydronaphthalene ring together with a benzene ring to which they bind;

$R^{3B}$ and $R^{4B}$ represent a hydrogen atom;

$R^{5B}$ represents a hydrogen atom;

$R^{6B}$ and $R^{7B}$ represent a hydrogen atom;

$X^B$ represents C or N;

$Y^B$ represents N or C(=O);

provided that when $X^B$ is N, $Y^B$ is not N; and when $X^B$ is C, $Y^B$ is not C(=O);

the double line consisting of the solid line and the broken line represents a single bond or a double bond;

$Z^B$ represents an oxygen atom;

$A^B$ represents a benzene ring;

$B^B$ represents $N(R^{8B})C(=O)$, NHCONH, or $N(R^{10B})SO_2$, wherein $R^{8B}$ and $R^{10B}$ represent a hydrogen atom;

$D^B$ represents an alkylene chain having 1 to 6 carbon atoms, or represents an atomic bond, $E^B$ represents O or an atomic bond;

$G^B$ represents benzene or pyridine, which may have 1 to 4 of the same or different substituents selected from the group consisting of an alkyl group having 1 to 8 carbon atoms, an alkyl group having 1 to 8 carbon atoms and substituted with 1 to 3 halogen atoms, a halogen atom, and a hydroxyl group; and $m^B$ represents 0.

2. A method of suppressing or treating a symptom associated with an allergic reaction selected from the group consisting of a symptom associated with a type I allergic reaction, an anaphylactic shock, allergic rhinitis, allergic dermatitis, pollinosis, urticaria and atopic dermatitis, the method comprising administering a compound having a P2X4 receptor antagonizing action or a pharmaceutically acceptable salt thereof to a subject in need of the method at a dose effective for suppressing or treating the symptom associated with the allergic reaction wherein the compound is selected from the group consisting of the following (A2), (A17) and (B208) or the compound is a compound or a pharmaceutically acceptable salt thereof selected from the group consisting of the following (B2), (B13), (B20), (B48), (B57), (B71), (B106), (B118), (B146), (B173), (B177), (B180), (B181), (B183), (B196), (B197), (B209), (B210) and (B214):

(A2) 5-[3-(1H-tetrazol-5-yl)phenyl]-1H-naphtho[1,2-b][1,4]diazepine-2,4 (3H,5H)-dione sodium salt;

(A17) 5-[3-(5-thioxo-4H-[1,2,4] oxadiazol-3-yl)phenyl]-1H-naphtho[1,2-b][1,4]diazepine-2,4 (3H,5H)-dione sodium salt;

(B2) 5-[4-[2-(trifluoromethyl)benzoyl]aminophenyl]-1H-naphtho[1,2-b][1,4]diazepine-2,4 (3H,5H)-dione;

(B13) 5-[4-[(2-chlorophenylacetyl)amino]phenyl]-1H-naphtho[1,2-b][1,4]diazepine-2,4 (3H,5H)-dione;

(B20) 1-[4-(2,4-dioxo-1,2,3,4-tetrahydronaphtho[1,2-b][1,4]diazepin-5-yl)phenyl]-3-phenylurea;

(B48) 5-[4-(2-iodobenzoylamino)phenyl]-1H-naphtho[1,2-b][1,4]diazepine-2,4 (3H,5H)-dione;

(B57) 5-[4-[(2-ethylbenzoyl)amino]phenyl]-1H-naphtho[1,2-b][1,4]diazepine-2,4 (3H,5H)-dione;

(B71) 5-[4-(2-tert-butylbenzoylamino)phenyl]-1H-naphtho[1,2-b][1,4]diazepine-2,4 (3H,5H)-dione;

(B106) 5-[4-(2-iodobenzoyl)aminophenyl]-1,2,3,4,8,9,10,11-octahydronaphtho[1,2-b][1,4]diazepine-2,4 (3H,5H)-dione;

(B118) 5-[4-(6-chloro-2-hydroxybenzoylamino)phenyl]-1H-naphtho[1,2-b][1,4]diazepine-2,4 (3H,5H)-dione;

(B146)N-[4-(2,4-dioxo-1,2,3,4-tetrahydronaphtho[1,2-b][1,4]diazepin-5-yl)phenyl]benzenesulfonamide;

(B173) 1-(2-chlorophenyl)-N-[4-(2,4-dioxo-1,2,3,4-tetrahydronaphtho[1,2-b][1,4]diazepin-5-yl)phenyl]methanesulfonamide;

(B177) 1-(2-chlorophenyl)-N-[4-(2,4-dioxo-1,2,3,4,8,9,10,11-octahydronaphtho[1,2-b][1,4]diazepin-5-yl)phenyl]methanesulfonamide;

(B180) 1-(2-bromophenyl)-N-[4-(2,4-dioxo-1,2,3,4-tetrahydronaphtho[1,2-b][1,4]diazepin-5-yl)phenyl]methanesulfonamide;

(B181)N-[4-(2,4-dioxo-1,2,3,4-tetrahydronaphtho[1,2-b][1,4]diazepin-5-yl)phenyl]-1-(2-methylphenyl)methanesulfonamide;

(B183)N-[4-(2,4-dioxo-1,2,3,4-tetrahydronaphtho[1,2-b][1,4]diazepin-5-yl)phenyl]-2-phenylethanesulfonamide;

(B196) 1-(2-chlorophenyl)-N-[4-(2,4-dioxo-1,2,3,4,8,9,10,11-octahydronaphtho[1,2-b][1,4]diazepin-5-yl)phenyl]-N-methylmethanesulfonamide;

(B197) 1-(2-chlorophenyl)-N-[4-(2-oxo-2,3-dihydro-1H-naphtho[1,2-e][1,4]diazepin-5-yl)phenyl]methanesulfonamide;

(B208) 5-[4-[(2-methylpyridin-3-yl)carbonylamino]phenyl]-1H-naphtho[1,2-b][1,4]diazepine-2,4(3H,5H)-dione hydrochloride;

(B209) 5-[4-[(2-chloropyridin-3-yl)carbonylamino]phenyl]-1H-naphtho[1,2-b][1,4]diazepine-2,4(3H,5H)-dione;

(B210) 5-[4-[2-[(pyridin-2-yl)oxy]acetylamino]phenyl]-1H-naphtho[1,2-b][1,4]diazepine-2,4(3H,5H)-dione;

(B214) 5-[4-[(2-isopropylbenzoyl)amino]phenyl]-1H-naphtho[1,2-b][1,4]diazepine-2,4(3H,5H)-dione.

3. A method of suppressing or treating a symptom associated with an allergic reaction selected from the group consisting of a symptom associated with a type I allergic reaction, an anaphylactic shock, allergic rhinitis, allergic dermatitis, pollinosis, urticaria and atopic dermatitis, the method comprising administering a compound having a P2X4 receptor antagonizing action or a pharmaceutically acceptable salt thereof to a subject in need of the method at a dose effective for suppressing or treating the symptom associated with the allergic reaction, wherein the compound having the P2X4 receptor antagonizing action is the following compound (B48) or a pharmaceutically acceptable salt thereof:

(B48) 5-[4-(2-iodobenzoylamino)phenyl]-1H-naphtho[1,2-b][1,4]diazepine-2,4(3H,5H)-dione.

4. The method according to claim 1, wherein the symptom associated with the allergic reaction is the type I allergic reaction.

5. The method according to claim 1, wherein the symptom associated with the allergic reaction is anaphylactic shock.

6. The method according to claim 1, wherein the symptom associated with the allergic reaction is allergic rhinitis.

7. The method according to claim 1, wherein the symptom associated with the allergic reaction is allergic dermatitis.

8. The method according to claim 1, wherein the symptom associated with the allergic reaction is pollinosis.

9. The method according to claim 1, wherein the symptom associated with the allergic reaction is urticaria.

10. The method according to claim 1, wherein the symptom associated with the allergic reaction is atopic dermatitis.

11. The method according to claim 2, wherein the symptom associated with the allergic reaction is the type I allergic reaction.

12. The method according to claim 2, wherein the symptom associated with the allergic reaction is anaphylactic shock.

13. The method according to claim 2, wherein the symptom associated with the allergic reaction is allergic rhinitis.

14. The method according to claim 2, wherein the symptom associated with the allergic reaction is allergic dermatitis.

15. The method according to claim 2, wherein the symptom associated with the allergic reaction is pollinosis.

16. The method according to claim 2, wherein the symptom associated with the allergic reaction is urticaria.

17. The method according to claim 2, wherein the symptom associated with the allergic reaction is atopic dermatitis.

18. The method according to claim 3, wherein the symptom associated with the allergic reaction is the type I allergic reaction.

19. The method according to claim 3, wherein the symptom associated with the allergic reaction is anaphylactic shock.

20. The method according to claim 3, wherein the symptom associated with the allergic reaction is allergic rhinitis.

21. The method according to claim 3, wherein the symptom associated with the allergic reaction is allergic dermatitis.

22. The method according to claim 3, wherein the symptom associated with the allergic reaction is pollinosis.

23. The method according to claim 3, wherein the symptom associated with the allergic reaction is urticaria.

24. The method according to claim 3, wherein the symptom associated with the allergic reaction is atopic dermatitis.

* * * * *